United States Patent
Scholz et al.

(10) Patent No.: US 11,760,809 B2
(45) Date of Patent: Sep. 19, 2023

(54) HUMAN MONOCLONAL ANTIBODIES TO GANGLIOSIDE GD2

(71) Applicant: BioNTech SE, Mainz (DE)

(72) Inventors: Wolfgang Scholz, San Diego, CA (US); Ritsuko Sawada, San Diego, CA (US)

(73) Assignee: BioNTech SE, Mainz (DE)

( * ) Notice: Subject to any disclaimer, the term of this patent is extended or adjusted under 35 U.S.C. 154(b) by 311 days.

(21) Appl. No.: 17/131,713

(22) Filed: Dec. 22, 2020

(65) Prior Publication Data

US 2021/0189000 A1    Jun. 24, 2021

Related U.S. Application Data

(62) Division of application No. 15/839,391, filed on Dec. 12, 2017, now Pat. No. 10,906,988, which is a division of application No. 14/730,036, filed on Jun. 3, 2015, now Pat. No. 9,856,324.

(60) Provisional application No. 62/007,874, filed on Jun. 4, 2014.

(51) Int. Cl.
| | |
|---|---|
| *C07K 16/00* | (2006.01) |
| *C07K 16/30* | (2006.01) |
| *A61K 39/395* | (2006.01) |
| *A61K 45/06* | (2006.01) |
| *G01N 33/574* | (2006.01) |
| *A61K 39/00* | (2006.01) |

(52) U.S. Cl.
CPC .... *C07K 16/3084* (2013.01); *A61K 39/39558* (2013.01); *A61K 45/06* (2013.01); *G01N 33/57492* (2013.01); *A61K 2039/505* (2013.01); *C07K 2317/21* (2013.01); *C07K 2317/33* (2013.01); *C07K 2317/56* (2013.01); *C07K 2317/565* (2013.01); *C07K 2317/73* (2013.01); *C07K 2317/732* (2013.01); *C07K 2317/734* (2013.01); *C07K 2317/77* (2013.01); *C07K 2317/92* (2013.01); *G01N 2405/10* (2013.01)

(58) Field of Classification Search
CPC .............. A61K 39/39558; A61K 45/06; A61K 2039/505; C07K 2317/21; C07K 2317/33; C07K 2317/56; C07K 2317/565
See application file for complete search history.

(56) References Cited

U.S. PATENT DOCUMENTS

| | | |
|---|---|---|
| 5,057,313 A | 10/1991 | Shih et al. |
| 5,112,946 A | 5/1992 | Maione et al. |
| 5,122,464 A | 6/1992 | Wilson et al. |
| 5,223,409 A | 6/1993 | Ladner et al. |
| 5,336,603 A | 8/1994 | Capon et al. |
| 5,349,053 A | 9/1994 | Landolfi et al. |
| 5,359,046 A | 10/1994 | Capon et al. |
| 5,403,484 A | 4/1995 | Ladner et al. |
| 5,427,908 A | 6/1995 | Dower et al. |
| 5,443,953 A | 8/1995 | Hansen et al. |
| 5,447,851 A | 9/1995 | Beutler et al. |
| 5,516,637 A | 5/1996 | Huang et al. |
| 5,571,698 A | 11/1996 | Ladner et al. |
| 5,580,717 A | 12/1996 | Dower et al. |
| 5,622,929 A | 4/1997 | Willner et al. |
| 5,658,727 A | 8/1997 | Barbas et al. |
| 5,698,426 A | 12/1997 | Huse et al. |
| 5,723,125 A | 3/1998 | Chang et al. |
| 5,733,743 A | 3/1998 | Johnson et al. |
| 5,750,753 A | 5/1998 | Kimae et al. |
| 5,780,225 A | 7/1998 | Wigler et al. |
| 5,783,181 A | 7/1998 | Browne et al. |
| 5,795,737 A | 8/1998 | Seed et al. |
| 5,821,047 A | 10/1998 | Garrard et al. |
| 5,844,095 A | 12/1998 | Linsley et al. |
| 5,908,626 A | 6/1999 | Chang et al. |
| 5,969,108 A | 10/1999 | McCafferty et al. |
| 6,254,868 B1 | 7/2001 | Leung et al. |
| 7,981,695 B2 | 7/2011 | Schultz et al. |

(Continued)

FOREIGN PATENT DOCUMENTS

| | | |
|---|---|---|
| DE | 10059930 A1 | 5/2002 |
| EP | 307434 A1 | 3/1989 |

(Continued)

OTHER PUBLICATIONS

"Analysis, Results, and Future Prospective of the Therapeutic Use of Radiolabeled Antibody in Cancer Therapy", in Monoclonal Antibodies for Cancer Detection and Therapy, Baldwin et al. (eds.), pp. 303-316 (Academic Press 1985).

(Continued)

*Primary Examiner* — Lei Yao

(74) *Attorney, Agent, or Firm* — Choate, Hall & Stewart LLP; Brenda Herschbach Jarrell; Rolando Medina

(57) ABSTRACT

The present invention provides compositions for the production of an antibody or functional fragment thereof directed against disialoganglioside-GD2. The compositions of the invention include polynucleotides encoding a heavy chain and/or a light chain variable domain that binds to GD2. The invention also provides an isolated antibody or functional fragment thereof and methods of treating or preventing a disease, such as cancer or tumor formation, wherein the antibody or functional fragment includes a variable heavy chain domain and a variable light chain domain that has an amino acid sequence provided herein. The invention further provides a conjugate of an antibody or functional fragment thereof conjugated or recombinantly fused to a diagnostic agent, detectable agent or therapeutic agent, and methods of treating, preventing or diagnosing a disease in a subject in need thereof.

10 Claims, 30 Drawing Sheets

Specification includes a Sequence Listing.

(56) References Cited

U.S. PATENT DOCUMENTS

| | | | |
|---|---|---|---|
| 8,039,273 | B2 | 10/2011 | Jeffrey et al. |
| 8,142,784 | B2 | 3/2012 | Ebens et al. |
| 8,216,581 | B2 | 7/2012 | Siegel |
| 9,856,324 | B2 | 1/2018 | Scholz et al. |
| 10,906,988 | B2 | 2/2021 | Scholz et al. |
| 2008/0076161 | A1 | 3/2008 | Angov et al. |
| 2009/0202536 | A1 | 8/2009 | Ebens et al. |
| 2010/0034837 | A1 | 2/2010 | Beria et al. |
| 2011/0076284 | A1 | 3/2011 | Corbin et al. |
| 2011/0137017 | A1 | 6/2011 | Eigenbrot et al. |
| 2011/0280891 | A1 | 11/2011 | Liu et al. |
| 2012/0003247 | A1 | 1/2012 | Doronina et al. |
| 2013/0216528 | A1 | 8/2013 | Cheung et al. |
| 2015/0353645 | A1 | 12/2015 | Scholz et al. |
| 2018/0346597 | A1 | 12/2018 | Scholz et al. |

FOREIGN PATENT DOCUMENTS

| | | | |
|---|---|---|---|
| EP | | 367166 A1 | 5/1990 |
| EP | | 394827 A1 | 10/1990 |
| WO | WO-8605807 A1 | | 10/1986 |
| WO | WO-8901036 A1 | | 2/1989 |
| WO | WO-90/02809 A1 | | 3/1990 |
| WO | WO-91/06570 A1 | | 5/1991 |
| WO | WO-91/10737 A1 | | 7/1991 |
| WO | WO-92/01047 A1 | | 1/1992 |
| WO | WO-92/18619 A1 | | 10/1992 |
| WO | WO-92/22324 A1 | | 12/1992 |
| WO | WO-93/11236 A1 | | 6/1993 |
| WO | WO-95/15982 A2 | | 6/1995 |
| WO | WO-95/20401 A1 | | 8/1995 |
| WO | WO-96/04388 A1 | | 2/1996 |
| WO | WO-96/22024 A1 | | 7/1996 |
| WO | WO-97/13844 A1 | | 4/1997 |
| WO | WO-97/34631 A1 | | 9/1997 |
| WO | WO-99/04813 A1 | | 2/1999 |
| WO | WO-02/087611 A2 | | 11/2002 |
| WO | WO-2008/000632 A1 | | 1/2008 |
| WO | WO-2010/122460 A1 | | 10/2010 |
| WO | WO-2015/187811 A2 | | 12/2015 |

OTHER PUBLICATIONS

Al-Lazikani et al., "Standard conformations for the canonical structures of immunoglobulins," J. Mol. Biol. 273:927-948 (1997).
Ames et al., "Conversion of murine Fabs isolated from a combinatorial phage display library to full length immunoglobulins," J. Immunol. Methods 184:177-186 (1995).
Ashkenazi et al., "Protection against endotoxic shock by a tumor necrosis factor receptor immunoadhesin," Proc. Natl. Acad. Sci. USA, 88: 10535-10539 (1991).
Battulal VL et al., "Ganglioside GD2 identifies breast cancer stem cells and promotes tumorigenesis," J Clin Invest.122(6):2066-2078 (2012).
Bebbington et al., "High-level expression of a recombinant antibody from myeloma cells using a glutamine synthetase gene as an amplifiable selectable marker," Biotechnology 10:169 (1992).
Better et al., "*Escherichia coli* secretion of an active chimeric antibody fragment," Science 240:1041-1043 (1988).
Bird et al., "Single-chain antigen-binding proteins," Science 242:423-26 (1988).
Bittner et al., "Expression and Secretion Vectors for Yeast," Methods in Enzymol., 153:516-544 (1987).
Brinkman et al., "Phage display of disulfide-stabilized Fv fragments," J. Immunol. Methods 182:41-50 (1995).
Brochet et al., "IMGT/V-QUEST: the highly customized and integrated system for IG and TR standardized V-J and V-D-J sequence analysis," Nucleic Acids Res, 36:W503-8. (2008).
Burton et al., "Human antibodies from combinatorial libraries," Advances in Immunology 57:191-280 (1994).
Caldas et al. (Mol. Immunol. May 2003; 39 (15): 941-952).
Casset, F. et al. A peptide mimetic of an anti-CD4 monoclonal antibody by rational design, Biochem. Biophys. Res. Commun., 307(1):198-205 (2003).
Catera et al., "Chronic Lymphocytic Leukemia Cells Recognize Conserved Epitopes Associated with Apoptosis and Oxidation," Mol. Med., 14(11-12):665-675 (2008).
Chien et al. (Proc. Natl. Acad. Sci. USA. Jul. 1989; 86 (14): 5532-5536).
Chothia and Lesk, "Canonical structures for the hypervariable regions of immunoglobulins," J. Mol. Biol. 196:901-917 (1987).
Cockett et al., "High level expression of tissue inhibitor of metalloproteinases in Chinese hamster ovary cells using glutamine synthetase gene amplification," 8: 662-667 (1990).
Crouse et al., "Expression and amplification of engineered mouse dihydrofolate reductase minigenes," Mol. Cell. Biol. 3:257 (1983).
De Pascalis, R. et al., Grafting of "Abbreviated" Complementarity-Determining Regions Containing Specificity-Determine Residues Essential for Ligand Contact to Engineer a Less Immunogenic Humanized Monoclonal Antibody, The Journal of Immunology, 169(6): 3076-3084 (2002)).
DeNardo et al., "Comparison of 1,4,7,10-tetraazacyclododecane-N,N',N",N"'-tetraaceticacid (DOTA)-peptide-ChL6, a novel immunoconjugate with catabolizable linker, to 2-iminothiolane-2-[p-(bromoacetamido)benzyl]-DOTA-ChL6 in breast cancerxenografts," Clin Cancer Res. 4(10):2483-2490 (1998).
Foecking et al., "Powerful and versatile enhancer—promoter unit for mammalian expression vectors," Gene 45:101-105 (1986).
Giusti et al. (Proc. Natl. Acad. Sci. USA. May 1987; 84 (9): 2926-2930).
Gottfried and Weinhold, "Sequence-specific covalent labelling of DNA," Biochem. Soc. Trans., 39(2):523-528 (2011).
Gussow et al. (Methods in Enzymology. 1991; 203: 99-121).
Holliger et al., ""Diabodies": small bivalent and bispecific antibody fragments," Proc. Natl. Acad. Sci. USA 90:6444-48 (1993).
Holm et al. (Mol. Immunol. Feb. 2007; 44 (6): 1075-1084).
Huston et al., "Antigen recognition and targeted delivery by the single-chain Fv," Cell Biophysics, 22:189-224 (1993).
Huston et al., "Protein engineering of antibody binding sites: recovery of specific activity in an anti-digoxin single-chain Fv analogue produced in *Escherichia coli*," Proc. Natl. Acad. Sci. USA 85:5879-5883 (1988).
Inouye & Inouye, "Up-promoter mutations in the Ipp gene of *Escherichia coli*," Nucleic Acids Res. 13:3101-3109 (1985).
International Search Report for PCT/US15/33954, (Human Monoclonal Antibodies to Ganglioside GD2, filed Jun. 3, 2015), received by ISA/US, 5 pages (dated Nov. 19, 2015).
Irie, R. and Morton, D., Regression of cutaneous metastatic melanoma by intralesional injection with human monoclonal antibody to ganglioside GD2, Proc. Natl. Acad. Sci. USA, 83:8694-8698 (1986).
Jalkanen et al., "Cell surface proteoglycan of mouse mammary epithelial cells is shed by cleavage of its matrix-binding ectodomain from its membrane-associated domain," J. Cell. Biol. 105:3087-3096 (1987).
Jalkanen et al., "Heparan sulfate proteoglycans from mouse mammary epithelial cells: localization on the cell surface with a monoclonal antibody," J. Cell. Biol. 101:976-985 (1985).
Kabat et al., "Unusual distributions of amino acids in complementarity-determining (hypervariable) segments of heavy and light chains of immunoglobulins and their possible roles in specificity of antibody-combining sites," J. Biol. Chem.252:6609-6616 (1977).
Kabat, "The structural basis of antibody complementarity," Adv. Prot. Chem. 32:1-75 (1978).
Kanaya et al., "Studies of codon usage and tRNA genes of 18 unicellular organisms and quantification of Bacillus subtilis tRNAs: gene expression level and species-specific diversity of codon usage based on multivariate analysis," Gene, 238:143-155(1999).
Kettleborough et al., "Isolation of tumor cell-specific single-chain Fv from immunized mice using phage-antibody libraries and the re-construction of whole antibodies from these antibody fragments," Eur. J. Immunol. 24:952-958 (1994).
Kohler, "Immunoglobulin chain loss in hybridoma lines," Proc. Natl. Acad. Sci. USA 77:2197-2199 (1980).

(56) References Cited

OTHER PUBLICATIONS

Kutmeier et al., "Assembly of humanized antibody genes from synthetic oligonucleotides using a single-round PCR," BioTechniques 17:242 (1994).
Leung et al., "Engineering a unique glycosylation site for site-specific conjugation of haptens to antibody fragments," J. Immunol., 154: 5919-5926 (1995).
Logan & Shenk, "Adenovirus tripartite leader sequence enhances translation of mRNAs late after infection," Proc. Natl. Acad. Sci. USA 8 1:355-359 (1984).
Lowy et al., "Isolation of transforming DNA: cloning the hamster aprt gene", Cell 22:8-17 (1980).
MacCallum et al. (J. Mol. Biol. Oct. 11, 1996; 262 (5): 732-745).
Mariuzza et al. (Annu. Rev. Biophys. Biophys. Chem. 1987; 16:139-159).
Morea et al., "Antibody modeling: implications for engineering and design," Methods 20:267-279 (2000).
Morgan and Anderson, "Human gene therapy," Ann. Rev. Biochem. 62:191-217 (1993).
Mulligan & Berg, "Selection for animal cells that express the *Escherichia coli* gene coding for xanthine-guanine phosphoribosyltransferase," Proc. Natl. Acad. Sci. USA 78:2072 (1981).
Mulligan, "The basic science of gene therapy," Science 260:926-932 (1993).
Mullinax et al., "Expression of a heterodimeric Fab antibody protein in one cloning step," BioTechniques 12(6):864-869 (1992).
Natsume et al., "Fucose removal from complex-type oligosaccharide enhances the antibody-dependent cellular cytotoxicity of single-gene-encoded antibody comprising a single-chain antibody linked the antibody constant region," J. Immunol. Methods.,306:93-103 (2005).
O'Hare et al., "Transformation of mouse fibroblasts to methotrexate resistance by a recombinant plasmid expressing a prokaryotic dihydrofolate reductase," Proc. Natl. Acad. Sci. USA 78:1527 (1981).
Okazaki et al., "Fucose depletion from human IgG1 oligosaccharide enhances binding enthalpy and association rate between IgG1 and FcgammaRIIIa," J Mol Biol., 336:1239-1249 (2004).
Paredes et al., "RNA labeling, conjugation and ligation," Methods, 54(2):251-259 (2011).
Paul, William E., Fundamental Immunology, Third Edition, pp. 292-295 (1993).
Peipp et al., "Antibody fucosylation differentially impacts cytotoxicity mediated by NK and PMN effector cells," Blood, 112(6):2390-2399 (2008).
Persic et al., "An integrated vector system for the eukaryotic expression of antibodies or their fragments after selection from phage display libraries," Gene 187:9-18 (1997).
Peterson et al., "Enzymatic cleavage of peptide-linked radiolabels from immunoconjugates," Bioconjug. Chem. 10(4):553-557 (1999).
Pluckthun and Skerra, "Expression of functional antibody Fv and Fab fragments in *Escherichia coli*," Meth. Enzymol., 178:497-515 (1989).
Poljak et al., "Production and structure of diabodies.," Structure 2:1121-23 (1994).
Proudfoot, "Transcriptional interference and termination between duplicated alpha-globin gene constructs suggests a novel mechanism for gene regulation." Nature 322:(6079): 562-565(1986).
Ru et al., "Molecular and Genetic Characterizations of Five Pathogenic and Two Nonpathogenic Monoclonal antiphospholipid Antibodies," Mol. Immunol., 39(5-6):299-311 (2002).
Rudikoff, S. et al. Single amino acid substitution altering antigen-binding specificity, Proc. Natl. Acad. Sci. USA., 79: 979-1983 (1982).
Ruther, et al., "Easy identification of cDNA clones," EMBO 2(10): 1791(1983).
Santerre et al., "Expression of prokaryotic genes for hygromycin B and G418 resistance as dominant-selection markers in mouse L cells," Gene 30:147 (1984).
Sawai et al., "Direct production of the Fab fragment derived from the sperm immobilizing antibody using polymerase chain reaction and cDNA expression vectors," AJRI 34:26-34 (1995).
Senter, "Potent antibody drug conjugates for cancer therapy," Current Opinion in Chemical Biology, 13:235-244 (2009).
Shields et al., "Lack of fucose on human IgG1 N-linked oligosaccharide improves binding to human Fcgamma RIII and antibody-dependent cellular toxicity," J. Biol. Chem., 277(30):26733-40 (2002).
Shih et al., "A fluorouridine-anti-CEA immunoconjugate is therapeutically effective in a human colonic cancer xenograft model," Int. J. Cancer. 46:1101-1106 (1990).
Shih et al., "Site-specific linkage of methotrexate to monoclonal antibodies using an intermediate carrier," Int. J. Cancer. 41:832-839 (1988).
Szybalska & Szybalski, "Genetics of human cell lines, IV. DNA-mediated heritable transformation of a biochemical trait." Proc. Natl. Acad. Sci. USA 48(12): 2026-2034 (1962).
Thorpe et al., "The preparation and cytotoxic properties of antibody-toxin conjugates," Immunol. Rev. 62:119-158 (1982).
Tolstoshev, "Gene therapy, concepts, current trials and future directions," Ann. Rev. Pharmacol. Toxicol. 32:573-596 (1993).
Traunecker et al., "Soluble CD4 molecules neutralize human immunodeficiency virus type 1," Nature, 331:84-86 (1988).
Tsao, C. et al., "Anti-proliferative and pro-apoptotic activity of GD2 ganglioside-specific monoclonal antibody 3F8 in human melanoma cells, OncoImmunology, 4(8):e1023975-1-e1023975-10 (2015).
Vajdos et al. (J. Mol. Biol. Jul. 5, 2002; 320 (2): 415-428).
Van Heeke & Schuster, "Expression of human asparagine synthetase in *Escherichia coli*," J. Biol. Chem. 24:5503-5509 (1989).
Vie et al., "Human fusion proteins between interleukin 2 and IgM heavy chain are cytotoxic for cells expressing the interleukin 2 receptor," Proc. Natl. Acad. Sci. USA, 89:11337-11341 (1992).
Wang et al., "Analysis of codon usage patterns of bacterial genomes using the self-organizing map," Mol. Biol. Evol., 18(5):792-800 (2001).
Ward et al., "Binding activities of a repertoire of single immunoglobulin variable domains secreted from *Escherichia coli*," Nature 341:544-546 (1989).
Wargalla, U. and Reisfeld, R., Rate of internalization of an immunotoxin correlates with cytotoxic activity against human tumor cells, Proc. Natl. Acad. Sci. USA, 86:5146-5150 (1989).
Wigler et al., "Transfer of purified herpes virus thymidine kinase gene to cultured mouse cells," Cell 11:223 (1977).
Wigler et al., "Transformation of mammalian cells with an amplifiable dominant-acting gene," Proc. Natl. Acad. Sci. USA. 77(6):3567-3570 (1980).
Winkler et al. (J. Immunol. Oct. 15, 2000; 165 (8): 4505-4514).
Written Opinion for PCT/US15/33954, (Human Monoclonal Antibodies to Ganglioside GD2, filed Jun. 3, 2015), received by ISA/US, 8 pages (dated Nov. 19, 2015).
Wu and Wu, "Delivery systems for gene therapy," Biotherapy 3:87-95 (1991).
Wu et al. (J. Mol. Biol. Nov. 19, 1999; 294 (1): 151-162).
Yamane-Ohnuki et al., "Production of therapeutic antibodies with controlled fucosylation," MAbs., 1(3):230-236 (2009).
Yu et al., "Peptide-antibody conjugates for tumour therapy: a MHC-class-II-restricted tetanus toxin peptide coupled to an anti-Ig light chain antibody can induce cytotoxic lysis of a human B-cell lymphoma by specific CD4 T cells," Int. J. Cancer 56:244 (1994).
Zheng et al., "Administration of noncytolytic IL-10/Fc in murine models of lipopolysaccharide-induced septic shock and allogeneic islet transplantation," J. Immunol., 154:5590-5600, 1995.
Zimmerman et al., "A triglycine linker improves tumor uptake and biodistributions of 67-Cu-labeled anti-neuroblastoma MAb chCE7 F(ab')2 fragments," Nucl. Med. Biol. 26(8):943-950 (1999).

```
        Q   V   Q   L   V   E   S   G   A   E   V   K   K   P   G   A   S   V   K   V
  1 CAAGTGCAGC TGGTGGAGTC TGGGGCTGAG GTGAAGAAGC CTGGGGCCTC AGTGAAGGTT
        S   C   K   A   S   G   Y   T   F   T   S   Y   A   I   H   W   V   R   Q   A
 61 TCCTGCAAGG CTTCTGGATA CACCTTCACT AGTTATGCTA TACATTGGGT GCGCCAGGCC
        P   G   Q   R   L   E   W   M   G   W   I   N   A   G   N   G   Y   R   K   Y
121 CCCGGACAAA GGCTTGAGTG GATGGGATGG ATCAACGCTG GAATGGTTA CAGAAAATAT
        S   Q   K   F   Q   G   R   V   T   V   T   R   D   T   S   A   S   T   A   Y
181 TCACAGAAGT TCCAGGGCAG AGTCACCGTT ACCAGGGACA CATCCGCGAG CACAGCCTAC
        M   E   L   S   S   L   R   S   E   D   T   A   V   Y   Y   C   A   R   F   E
241 ATGGAGCTGA GTAGTTTGAG ATCTGAAGAC ACGGCTGTGT ATTACTGTGC GAGATTCGAA
        G   G   M   V   T   A   M   D   F   W   G   Q   G   T   L   V   T   V   S   S
301 GGAGGGATGG TGACTGCCAT GGACTTCTGG GGCCAGGGAA CCCTGGTCAC CGTCTCCTCA

1 CAAGTGCAGC TGGTGGAGTC TGGGGCTGAG GTGAAGAAGC CTGGGGCCTC AGTGAAGGTT
 61 TCCTGCAAGG CTTCTGGATA CACCTTCACT AGTTATGCTA TACATTGGGT GCGCCAGGCC
121 CCCGGACAAA GGCTTGAGTG GATGGGATGG ATCAACGCTG GAATGGTTA CAGAAAATAT
181 TCACAGAAGT TCCAGGGCAG AGTCACCGTT ACCAGGGACA CATCCGCGAG CACAGCCTAC
241 ATGGAGCTGA GTAGTTTGAG ATCTGAAGAC ACGGCTGTGT ATTACTGTGC GAGATTCGAA
301 GGAGGGATGG TGACTGCCAT GGACTTCTGG GGCCAGGGAA CCCTGGTCAC CGTCTCCTCA

```
          D   V   V   M   T   Q   S   P   L   S   L   P   V   T   P   G   E   P   A   S
  1 GATGTTGTGA TGACCCAGTC TCCACTCTCC CTGCCCGTCA CCCCTGGAGA GCCGGCCTCC
      I   S   C   R   S   S   Q   S   L   L   H   R   N   G   Y   N   Y   L   D   W
 61 ATCTCCTGCA GGTCTAGTCA GAGCCTCCTG CATAGAAATG GATACAACTA CTTGGATTGG
      Y   L   Q   K   P   G   Q   S   P   Q   L   L   I   Y   L   G   S   N   R   A
121 TACCTGCAGA AGCCAGGGCA GTCTCCACAG CTCCTGATCT ATTTGGGTTC TAATCGGGCC
      S   G   V   P   D   R   F   S   G   S   G   S   G   T   D   F   T   L   K   I
181 TCCGGGGTCC CTGACAGGTT CAGTGGCAGT GGATCAGGCA CAGATTTTAC ACTGAAAATC
      S   R   V   E   A   E   D   V   G   V   Y   Y   C   M   Q   A   L   Q   T   P
241 AGCAGAGTGG AGGCTGAGGA TGTTGGGGTT TATTACTGCA TGCAAGCTCT ACAAACTCCC
      F   T   F   G   P   G   T   K   V   D   I   K
301 TTCACTTTCG GCCCTGGGAC CAAAGTGGAT ATCAAA
```

```
  1 GATGTTGTGA TGACCCAGTC TCCACTCTCC CTGCCCGTCA CCCCTGGAGA GCCGGCCTCC
 61 ATCTCCTGCA GGTCTAGTCA GAGCCTCCTG CATAGAAATG GATACAACTA CTTGGATTGG
121 TACCTGCAGA AGCCAGGGCA GTCTCCACAG CTCCTGATCT ATTTGGGTTC TAATCGGGCC
181 TCCGGGGTCC CTGACAGGTT CAGTGGCAGT GGATCAGGCA CAGATTTTAC ACTGAAAATC
241 AGCAGAGTGG AGGCTGAGGA TGTTGGGGTT TATTACTGCA TGCAAGCTCT ACAAACTCCC
301 TTCACTTTCG GCCCTGGGAC CAAAGTGGAT ATCAAA
```

```
        E   V   Q   L   L   E   S   G   A   E   V   K   K   P   G   A   S   V   K   V
    1 GAGGTGCAGC TGTTGGAGTC TGGGGCTGAG GTGAAGAAGC CTGGGGCCTC AGTGAAGGTT
        S   C   K   A   S   G   Y   T   F   T   S   Y   A   I   H   W   V   R   Q   A
   61 TCCTGCAAGG CTTCTGGATA CACCTTCACT AGCTATGCTA TACATTGGGT GCGCCAGGCC
        P   G   Q   R   L   E   W   M   G   W   I   N   A   G   N   G   Y   R   K   Y
  121 CCCGGACAAA GGCTTGAGTG GATGGGATGG ATCAACGCTG GAATGGTTA CAGAAAATAT
        S   Q   K   F   Q   G   R   V   T   V   T   R   D   T   S   A   S   T   A   Y
  181 TCACAGAAAT TCCAGGGCAG AGTCACCGTT ACCAGGGACA CATCCGCGAG CACAGCCTAC
        M   E   L   S   S   L   R   S   E   D   T   A   V   Y   Y   C   A   R   F   E
  241 ATGGAGTTGA GCAGCCTGAG ATCTGAAGAC ACGGCTGTGT ATTACTGTGC GAGATTCGAA
        G   G   M   V   T   A   M   D   Y   W   G   Q   G   T   L   V   T   V   S   S
  301 GGAGGGATGG TGACTGCCAT GGACTACTGG GGCCAGGGAA CCCTGGTCAC CGTCTCCTCA

1 GAGGTGCAGC TGTTGGAGTC TGGGGCTGAG GTGAAGAAGC CTGGGGCCTC AGTGAAGGTT
   61 TCCTGCAAGG CTTCTGGATA CACCTTCACT AGCTATGCTA TACATTGGGT GCGCCAGGCC
  121 CCCGGACAAA GGCTTGAGTG GATGGGATGG ATCAACGCTG GAATGGTTA CAGAAAATAT
  181 TCACAGAAAT TCCAGGGCAG AGTCACCGTT ACCAGGGACA CATCCGCGAG CACAGCCTAC
  241 ATGGAGTTGA GCAGCCTGAG ATCTGAAGAC ACGGCTGTGT ATTACTGTGC GAGATTCGAA
  301 GGAGGGATGG TGACTGCCAT GGACTACTGG GGCCAGGGAA CCCTGGTCAC CGTCTCCTCA

```
         D   I   Q   V   T   Q   S   P   L   S   L   P   V   T   P   G   E   P   A   S
  1 GACATCCAGG TGACCCAGTC TCCACTCTCC CTGCCCGTCA CCCCTGGAGA GCCGGCCTCC
         I   S   C   R   S   S   Q   S   L   L   H   S   N   G   Y   N   Y   L   D   W
 61 ATCTCCTGCA GGTCTAGTCA GAGCCTCCTG CATAGTAATG GATACAACTA TTTGGATTGG
         Y   L   Q   K   P   G   Q   S   P   Q   L   L   I   Y   L   G   S   N   R   A
121 TACCTGCAGA AGCCAGGGCA GTCTCCACAG CTCCTGATCT ATTTGGGTTC TAATCGGGCC
         S   G   V   P   D   R   F   S   G   S   G   S   G   T   D   F   T   L   K   I
181 TCCGGGGTCC CTGACAGGTT CAGTGGCAGT GGATCAGGCA CAGATTTTAC ACTGAAAATC
         S   R   V   E   A   E   D   V   G   V   Y   Y   C   M   Q   A   L   Q   T   P
241 AGCAGAGTGG AGGCTGAGGA TGTTGGGGTT TATTACTGCA TGCAAGCTCT ACAAACTCCC
         F   T   F   G   P   G   I   K   V   D   I   K
301 TTCACTTTCG GCCCTGGGAT CAAAGTGGAT ATCAAA

1 GACATCCAGG TGACCCAGTC TCCACTCTCC CTGCCCGTCA CCCCTGGAGA GCCGGCCTCC
 61 ATCTCCTGCA GGTCTAGTCA GAGCCTCCTG CATAGTAATG GATACAACTA TTTGGATTGG
121 TACCTGCAGA AGCCAGGGCA GTCTCCACAG CTCCTGATCT ATTTGGGTTC TAATCGGGCC
181 TCCGGGGTCC CTGACAGGTT CAGTGGCAGT GGATCAGGCA CAGATTTTAC ACTGAAAATC
241 AGCAGAGTGG AGGCTGAGGA TGTTGGGGTT TATTACTGCA TGCAAGCTCT ACAAACTCCC
301 TTCACTTTCG GCCCTGGGAT CAAAGTGGAT ATCAAA

```
         Q  V  Q  L  V  E  S  G  A  E  V  K  K  P  G  A  S  V  K  M
  1 CAAGTGCAGC TGGTGGAGTC TGGGGCTGAG GTGAAGAAGC CTGGGGCCTC AGTGAAGATG
         S  C  R  A  S  G  Y  T  F  T  R  Y  Y  M  H  W  V  R  Q  A
 61 TCCTGCAGGG CATCTGGATA CACCTTCACC AGGTACTATA TGCACTGGGT GCGACAGGCC
         P  G  Q  G  L  E  W  M  G  I  I  N  P  S  A  G  S  T  S  Y
121 CCTGGACAAG GGCTTGAGTG GATGGGAATA ATCAACCCTA GTGCTGGTAG CACAAGCTAC
         A  Q  K  F  Q  D  R  V  T  M  T  R  D  T  S  R  S  T  V  Y
181 GCACAGAAGT TCCAGGACAG AGTCACCATG ACCAGGGACA CGTCCAGGAG CACAGTCTAC
         M  E  L  S  S  L  R  S  E  D  T  A  V  Y  Y  C  A  R  R  V
241 ATGGAGCTGA GCAGCCTGAG ATCTGAGGAC ACGGCCGTGT ATTACTGTGC GAGAAGGGTG
         V  V  G  G  P  F  D  F  W  G  Q  G  T  L  V  T  V  S  S
301 GTAGTTGGGG GCCCGTTTGA CTTCTGGGGC CAGGGAACCC TGGTCACCGT CTCCTCA

1 CAAGTGCAGC TGGTGGAGTC TGGGGCTGAG GTGAAGAAGC CTGGGGCCTC AGTGAAGATG
 61 TCCTGCAGGG CATCTGGATA CACCTTCACC AGGTACTATA TGCACTGGGT GCGACAGGCC
121 CCTGGACAAG GGCTTGAGTG GATGGGAATA ATCAACCCTA GTGCTGGTAG CACAAGCTAC
181 GCACAGAAGT TCCAGGACAG AGTCACCATG ACCAGGGACA CGTCCAGGAG CACAGTCTAC
241 ATGGAGCTGA GCAGCCTGAG ATCTGAGGAC ACGGCCGTGT ATTACTGTGC GAGAAGGGTG
301 GTAGTTGGGG GCCCGTTTGA CTTCTGGGGC CAGGGAACCC TGGTCACCGT CTCCTCA

```
         D   I   Q   M   T   Q   S   P   D   S   L   A   V   S   L   G   E   R   A   T
  1 GACATCCAGA TGACCCAGTC TCCAGACTCC CTGGCTGTGT CTCTGGGCGA GAGGGCCACC
         I   N   C   K   S   S   Q   S   V   L   Y   S   P   N   K   K   N   Y   L   A
 61 ATCAACTGCA AGTCCAGCCA GAGTGTTTTA TACAGCCCCA ACAAAAAGAA CTACTTAGCT
         W   Y   Q   Q   K   P   G   Q   P   P   S   L   L   F   Y   W   A   S   T   R
121 TGGTACCAGC AGAAACCAGG ACAGCCTCCT AGTCTGCTCT TTTACTGGGC ATCTACCCGG
         E   S   G   V   P   D   R   F   S   G   S   G   S   G   T   D   F   T   L   T
181 GAATCCGGGG TCCCTGACCG ATTCAGTGGC AGCGGGTCTG GGACAGACTT CACTCTCACC
         I   S   S   L   Q   A   E   D   V   A   V   Y   Y   C   Q   Q   Y   Y   S   T
241 ATCAGCAGCC TGCAGGCTGA AGATGTGGCA GTTTATTACT GTCAGCAATA TTATAGTACT
         P   P   T   F   G   Q   G   T   K   V   E   I   K
301 CCTCCGACGT TCGGCCAAGG GACCAAGGTG GAAATCAAA
```

```
  1 GACATCCAGA TGACCCAGTC TCCAGACTCC CTGGCTGTGT CTCTGGGCGA GAGGGCCACC
 61 ATCAACTGCA AGTCCAGCCA GAGTGTTTTA TACAGCCCCA ACAAAAAGAA CTACTTAGCT
121 TGGTACCAGC AGAAACCAGG ACAGCCTCCT AGTCTGCTCT TTTACTGGGC ATCTACCCGG
181 GAATCCGGGG TCCCTGACCG ATTCAGTGGC AGCGGGTCTG GGACAGACTT CACTCTCACC
241 ATCAGCAGCC TGCAGGCTGA AGATGTGGCA GTTTATTACT GTCAGCAATA TTATAGTACT
301 CCTCCGACGT TCGGCCAAGG GACCAAGGTG GAAATCAAA
```

```
          Q   V   Q   L   V   E   S   G   A   E   V   K   K   P   G   A   S   V   R   V
  1 CAGGTGCAGC TGGTGGAATC TGGGGCTGAG GTGAAGAAGC CTGGGGCCTC AGTGAGGGTT
      S   C   K   A   S   G   Y   R   F   I   S   Y   Y   M   H   W   V   R   Q   A
 61 TCCTGCAAGG CATCTGGATA CAGGTTCATC AGCTACTATA TGCACTGGGT GCGACAGGCC
      P   G   Q   G   L   E   W   M   G   I   I   N   P   S   G   G   S   T   S   Y
121 CCTGGACAAG GGCTTGAGTG GATGGGAATA ATCAACCCTA GTGGTGGTAG CACAAGCTAC
      A   Q   K   F   Q   G   R   V   T   M   T   R   D   T   S   T   S   T   I   Y
181 GCACAGAAGT TCCAGGGCAG AGTCACCATG ACCAGGGACA CGTCCACGAG CACAATCTAC
      M   E   L   S   S   L   R   S   E   D   T   A   V   Y   Y   C   A   R   R   N
241 ATGGAGCTGA GCAGCCTGAG ATCTGAGGAC ACGGCCGTGT ATTACTGTGC GCGTCGCAAT
      I   V   T   G   P   F   D   Y   W   G   Q   G   T   L   V   T   V   S   S
301 ATTGTCACGG GTCCATTTGA CTATTGGGGC CAGGGAACCC TGGTCACCGT CTCCTCA

1 CAGGTGCAGC TGGTGGAATC TGGGGCTGAG GTGAAGAAGC CTGGGGCCTC AGTGAGGGTT
 61 TCCTGCAAGG CATCTGGATA CAGGTTCATC AGCTACTATA TGCACTGGGT GCGACAGGCC
121 CCTGGACAAG GGCTTGAGTG GATGGGAATA ATCAACCCTA GTGGTGGTAG CACAAGCTAC
181 GCACAGAAGT TCCAGGGCAG AGTCACCATG ACCAGGGACA CGTCCACGAG CACAATCTAC
241 ATGGAGCTGA GCAGCCTGAG ATCTGAGGAC ACGGCCGTGT ATTACTGTGC GCGTCGCAAT
301 ATTGTCACGG GTCCATTTGA CTATTGGGGC CAGGGAACCC TGGTCACCGT CTCCTCA

```
        D   V   V   M   T   Q   T    P   D   S    L   A   V   S    L   G   E   R   A   T
  1 GATGTTGTGA TGACTCAGAC TCCAGACTCC CTGGCTGTGT CTCTGGGCGA GAGGGCCACC
        I   N   C   K   S   S   Q    S   V   L    Y   I   S   N    N   K   N   Y   L   A
 61 ATCAACTGCA AGTCCAGCCA GAGTGTTTTA TACATCTCCA ACAATAAGAA CTACTTAGCT
        W   Y   Q   Q   K   P   G    Q   P   P    K   L   L   I    Y   W   A   S   T   R
121 TGGTACCAGC AGAAACCAGG ACAGCCTCCT AAGCTGCTCA TTTACTGGGC ATCTACCCGG
        E   S   G   V   P   D   R    F   S   G    S   G   S   G    T   D   F   T   L   T
181 GAATCCGGGG TCCCTGACCG ATTCAGTGGC AGCGGGTCTG GACAGATTT CACTCTCACC
        I   S   S   L   Q   A   E    D   V   A    V   Y   Y   C    Q   H   Y   Y   S   T
241 ATCAGCAGCC TGCAGGCTGA GGATGTGGCA GTTTATTACT GTCAGCACTA TTATAGTACT
        P   P   T   F   G   Q   G    T   K   L    E   I   K
301 CCTCCCACTT TTGGCCAGGG GACCAAGCTG GAGATCAAA
```

```
  1 GATGTTGTGA TGACTCAGAC TCCAGACTCC CTGGCTGTGT CTCTGGGCGA GAGGGCCACC
 61 ATCAACTGCA AGTCCAGCCA GAGTGTTTTA TACATCTCCA ACAATAAGAA CTACTTAGCT
121 TGGTACCAGC AGAAACCAGG ACAGCCTCCT AAGCTGCTCA TTTACTGGGC ATCTACCCGG
181 GAATCCGGGG TCCCTGACCG ATTCAGTGGC AGCGGGTCTG GACAGATTT CACTCTCACC
241 ATCAGCAGCC TGCAGGCTGA GGATGTGGCA GTTTATTACT GTCAGCACTA TTATAGTACT
301 CCTCCCACTT TTGGCCAGGG GACCAAGCTG GAGATCAAA
```

```
        Q   V   Q   L       V   E   S       G   A   E       V   K   K       P   G   A   S       V   K   V
  1 CAGGTGCAGC TGGTGGAATC TGGGGCTGAG GTGAAGAAGC CTGGGGCCTC AGTGAAGGTT
        S   C   K   A       S   G   Y       T   F   A       R   Y   Y       M   H   W   V       R   Q   A
 61 TCCTGCAAGG CATCTGGATA CACCTTCGCC AGGTACTATA TGCACTGGGT GCGACAGGCC
        P   G   Q   G       P   E   W       M   G   I       I   N   P       S   G   G   S       T   S   Y
121 CCTGGCCAAG GGCCTGAGTG GATGGGCATA ATCAACCCTA GTGGTGGAAG CACAAGTTAC
        A   Q   K   F       Q   G   R       V   T   V       T   R   D   T       S   T   S       T   V   Y
181 GCACAGAAGT TCCAGGGCAG AGTCACCGTG ACCAGGGACA CGTCCACGAG CACAGTCTAC
        M   E   L   S       S   L   R       S   E   D       T   A   V   Y       Y   C   A       R   R   V
241 ATGGAGCTGA GCAGCCTGAG ATCTGAGGAC ACGGCCGTGT ATTACTGTGC GAGGAGGGTG
        V   L   G   G       P   F   D       Y   W   G       Q   G   T       L   V   T   V       S   S
301 GTACTTGGGG GCCCGTTTGA CTACTGGGGC CAGGGAACCC TGGTCACCGT CTCCTCA
```

```
  1 CAGGTGCAGC TGGTGGAATC TGGGGCTGAG GTGAAGAAGC CTGGGGCCTC AGTGAAGGTT
 61 TCCTGCAAGG CATCTGGATA CACCTTCGCC AGGTACTATA TGCACTGGGT GCGACAGGCC
121 CCTGGCCAAG GGCCTGAGTG GATGGGCATA ATCAACCCTA GTGGTGGAAG CACAAGTTAC
181 GCACAGAAGT TCCAGGGCAG AGTCACCGTG ACCAGGGACA CGTCCACGAG CACAGTCTAC
241 ATGGAGCTGA GCAGCCTGAG ATCTGAGGAC ACGGCCGTGT ATTACTGTGC GAGGAGGGTG
301 GTACTTGGGG GCCCGTTTGA CTACTGGGGC CAGGGAACCC TGGTCACCGT CTCCTCA
```

```
            D   I   R   V   T   Q   S   P   D   S   L   A   V   S   L   G   E   R   A   T
  1 GACATCCGGG TGACCCAGTC TCCAGACTCC CTGGCTGTGT CTCTGGGCGA GAGGGCCACC
            I   N   C   K   S   S   Q   S   V   L   Y   S   S   N   N   K   N   Y   L   A
 61 ATCAACTGCA AGTCCAGCCA GAGTGTTTTA TACAGCTCCA ACAATAAGAA CTACTTAGCT
            W   Y   Q   Q   K   P   G   Q   P   P   K   L   L   I   Y   W   A   S   T   R
121 TGGTACCAGC AGAAACCAGG ACAGCCTCCT AAGCTGCTCA TTTACTGGGC ATCTACCCGG
            E   S   G   V   P   D   R   F   S   G   S   G   S   G   T   D   F   T   L   T
181 GAATCCGGGG TCCCTGACCG ATTCAGTGGC AGCGGGTCTG GACAGATTT CACTCTCACC
            I   S   S   L   Q   A   E   D   V   A   V   Y   Y   C   Q   Q   Y   Y   S   T
241 ATCAGCAGCC TGCAGGCTGA AGATGTGGCA GTTTATTACT GTCAGCAATA TTATAGTACT
            P   P   T   F   G   Q   G   T   K   V   E   I   K
301 CCTCCGACGT TCGGCCAAGG GACCAAGGTG GAAATCAAA
```

```
  1 GACATCCGGG TGACCCAGTC TCCAGACTCC CTGGCTGTGT CTCTGGGCGA GAGGGCCACC
 61 ATCAACTGCA AGTCCAGCCA GAGTGTTTTA TACAGCTCCA ACAATAAGAA CTACTTAGCT
121 TGGTACCAGC AGAAACCAGG ACAGCCTCCT AAGCTGCTCA TTTACTGGGC ATCTACCCGG
181 GAATCCGGGG TCCCTGACCG ATTCAGTGGC AGCGGGTCTG GACAGATTT CACTCTCACC
241 ATCAGCAGCC TGCAGGCTGA AGATGTGGCA GTTTATTACT GTCAGCAATA TTATAGTACT
301 CCTCCGACGT TCGGCCAAGG GACCAAGGTG GAAATCAAA
```

```
        E   V   Q   L       L   E   S       G   A   E       V   K   K       P   G   A   S       V   K   V
  1 GAAGTGCAGC TGTTGGAGTC TGGGGCTGAG GTGAAGAAGC CTGGGGCCTC AGTGAAGGTT
        S   C   K   A       S   G   Y       T   F   T       R   Y   Y       M   H   W   V       R   Q   A
 61 TCCTGCAAGG CATCTGGATA CACCTTCACC AGATACTATA TGCACTGGGT GCGACAGGCC
        P   G   Q   G       L   E   W       M   G   I       I   N   P       S   S   G   S       T   S   Y
121 CCTGGACAAG GGCTTGAGTG GATGGGAATA ATCAACCCTA GTAGTGGTAG CACAAGCTAC
        A   Q   K   F       Q   G   R       V   T   M       T   R   D   T       S   T   S       T   V   Y
181 GCACAGAAGT TCCAGGGCAG AGTCACCATG ACCAGGGACA CGTCCACGAG CACAGTCTAC
        M   E   L   S       S   L   R       S   E   D       M   A   V   Y       Y   C   A       R   R   V
241 ATGGAGCTGA GCAGCCTGAG ATCTGAGGAC ATGGCCGTAT ATTACTGTGC GAGGAGGGTG
        V   V   G   G       P   F   D       Y   W   G       Q   G   T       L   V   T   V       S   S
301 GTAGTTGGGG GCCCGTTTGA CTACTGGGGC CAGGGAACCC TGGTCACCGT CTCCTCA

1 GAAGTGCAGC TGTTGGAGTC TGGGGCTGAG GTGAAGAAGC CTGGGGCCTC AGTGAAGGTT
 61 TCCTGCAAGG CATCTGGATA CACCTTCACC AGATACTATA TGCACTGGGT GCGACAGGCC
121 CCTGGACAAG GGCTTGAGTG GATGGGAATA ATCAACCCTA GTAGTGGTAG CACAAGCTAC
181 GCACAGAAGT TCCAGGGCAG AGTCACCATG ACCAGGGACA CGTCCACGAG CACAGTCTAC
241 ATGGAGCTGA GCAGCCTGAG ATCTGAGGAC ATGGCCGTAT ATTACTGTGC GAGGAGGGTG
301 GTAGTTGGGG GCCCGTTTGA CTACTGGGGC CAGGGAACCC TGGTCACCGT CTCCTCA

```
        D   I   Q   L   T   Q   S   P   D   S   L   A   V   S   L   G   E   R   A   T
  1 GACATCCAGT TGACCCAGTC TCCAGACTCC CTGGCTGTGT CTCTGGGCGA GAGGGCCACC
        I   N   C   K   S   S   Q   S   I   L   Y   S   S   N   N   K   N   Y   L   A
 61 ATCAACTGCA AGTCCAGCCA GAGTATTTTA TACAGCTCCA ACAATAAGAA CTACTTAGCT
        W   Y   Q   Q   K   P   G   Q   P   P   K   L   L   I   Y   W   A   S   T   R
121 TGGTACCAGC AGAAACCAGG ACAGCCTCCT AAGCTGCTCA TTTACTGGGC ATCTACCCGG
        E   S   G   V   P   D   R   F   S   G   S   G   S   G   T   D   F   T   L   T
181 GAATCCGGGG TCCCTGACCG ATTCAGTGGC AGCGGGTCTG GACAGATTT CACTCTCACC
        I   S   S   L   Q   A   E   D   V   A   V   Y   Y   C   Q   Q   Y   Y   S   T
241 ATCAGCAGCC TGCAGGCTGA AGATGTGGCA GTTTATTACT GTCAGCAATA TTATAGTACT
        P   P   T   F   G   Q   G   T   K   V   E   I   K
301 CCTCCGACGT TCGGCCAAGG GACCAAGGTG GAAATCAAG

1 GACATCCAGT TGACCCAGTC TCCAGACTCC CTGGCTGTGT CTCTGGGCGA GAGGGCCACC
 61 ATCAACTGCA AGTCCAGCCA GAGTATTTTA TACAGCTCCA ACAATAAGAA CTACTTAGCT
121 TGGTACCAGC AGAAACCAGG ACAGCCTCCT AAGCTGCTCA TTTACTGGGC ATCTACCCGG
181 GAATCCGGGG TCCCTGACCG ATTCAGTGGC AGCGGGTCTG GACAGATTT CACTCTCACC
241 ATCAGCAGCC TGCAGGCTGA AGATGTGGCA GTTTATTACT GTCAGCAATA TTATAGTACT
301 CCTCCGACGT TCGGCCAAGG GACCAAGGTG GAAATCAAG

```
              E   V   Q   L   L   E   S   G   A   E   V   K   K   P   G   A   S   V   K   V
  1 GAAGTGCAGC TGTTGGAGTC TGGGGCTGAG GTGAAGAAGC CTGGGGCCTC AGTGAAGGTT
      S   C   K   A   S   G   Y   I   F   S   R   Y   A   I   H   W   V   R   Q   A
 61 TCCTGCAAGG CTTCTGGATA CATCTTCAGT AGATATGCTA TCCATTGGGT GCGCCAGGCC
      P   G   Q   G   L   E   W   M   G   W   I   N   P   F   N   G   F   T   K   Y
121 CCCGGACAAG GGCTTGAGTG GATGGGATGG ATCAACCCTT TCAATGGTTT CACAAAATAT
      S   Q   K   F   Q   G   R   V   A   L   T   R   D   R   S   A   T   T   G   Y
181 TCACAGAAGT TCAGGGCAG  AGTCGCCCTC ACTAGGGACA GATCCGCGAC CACAGGCTAC
      M   E   L   S   S   L   T   S   E   D   T   A   V   Y   Y   C   A   R   L   E
241 ATGGAGTTGA GCAGCCTGAC ATCTGAAGAC ACGGCTGTGT ACTACTGTGC GAGGCTGGAA
      S   N   K   F   Y   A   F   D   I   W   G   Q   G   T   M   V   T   V   S   S
301 TCTAACAAGT TTTATGCTTT TGATATCTGG GGCCAGGGGA CAATGGTCAC CGTCTCTTCA

1 GAAGTGCAGC TGTTGGAGTC TGGGGCTGAG GTGAAGAAGC CTGGGGCCTC AGTGAAGGTT
 61 TCCTGCAAGG CTTCTGGATA CATCTTCAGT AGATATGCTA TCCATTGGGT GCGCCAGGCC
121 CCCGGACAAG GGCTTGAGTG GATGGGATGG ATCAACCCTT TCAATGGTTT CACAAAATAT
181 TCACAGAAGT TCAGGGCAG  AGTCGCCCTC ACTAGGGACA GATCCGCGAC CACAGGCTAC
241 ATGGAGTTGA GCAGCCTGAC ATCTGAAGAC ACGGCTGTGT ACTACTGTGC GAGGCTGGAA
301 TCTAACAAGT TTTATGCTTT TGATATCTGG GGCCAGGGGA CAATGGTCAC CGTCTCTTCA

```
         E   I   V   M   T   Q   S    P   L   S    L   P   V   T    P   G   E   P   A   S
  1 GAAATTGTAA TGACACAGTC TCCACTCTCC CTGCCCGTCA CCCCTGGAGA GCCGGCCTCC
         I   S   C   T   S   S   Q    S   L   L    H   S   N   G    Y   N   Y   L   D   W
 61 ATCTCCTGCA CGTCTAGTCA GAGCCTCCTG CATAGTAATG GATATAACTA TTTGGATTGG
         Y   L   Q   K   P   G   Q    S   P   Q    L   L   I   Y    L   G   S   N   R   A
121 TACTTGCAGA AGCCAGGGCA GTCTCCACAG CTCCTGATCT ATTTGGGTTC TAATCGGGCC
         S   G   V   P   D   R   F    S   G   S    G   S   G   T    D   F   T   L   K   I
181 TCCGGGGTCC CTGACAGGTT CAGTGGCAGT GGATCAGGCA CAGATTTTAC ACTGAAAATC
         S   T   V   E   A   E   D    V   G   V    Y   Y   C   M    Q   A   L   Q   T   P
241 AGCACAGTGG AGGCTGAGGA TGTTGGGGTT TATTACTGCA TGCAAGCTCT ACAAACTCCG
         W   T   F   G   Q   G   T    K   V   E    I   K
301 TGGACGTTTG GCCAAGGGAC CAAGGTGGAA ATCAAA

1 GAAATTGTAA TGACACAGTC TCCACTCTCC CTGCCCGTCA CCCCTGGAGA GCCGGCCTCC
 61 ATCTCCTGCA CGTCTAGTCA GAGCCTCCTG CATAGTAATG GATATAACTA TTTGGATTGG
121 TACTTGCAGA AGCCAGGGCA GTCTCCACAG CTCCTGATCT ATTTGGGTTC TAATCGGGCC
181 TCCGGGGTCC CTGACAGGTT CAGTGGCAGT GGATCAGGCA CAGATTTTAC ACTGAAAATC
241 AGCACAGTGG AGGCTGAGGA TGTTGGGGTT TATTACTGCA TGCAAGCTCT ACAAACTCCG
301 TGGACGTTTG GCCAAGGGAC CAAGGTGGAA ATCAAA

```
        Q   V   Q   L   L   E   S   G   A   E   V   K   K   P   G   A   S   V   K   V
  1 CAAGTGCAGC TGTTGGAGTC TGGGGCTGAG GTGAAGAAGC TGGGGCCTC AGTGAAGGTT
        S   C   K   A   S   G   Y   T   F   T   S   Y   A   M   H   W   V   R   Q   A
 61 TCCTGCAAGG CTTCTGGATA CACCTTCACT AGCTATGCTA TGCATTGGGT GCGCCAGGCC
        P   G   Q   R   L   E   W   M   G   W   I   N   A   G   N   G   N   T   I   Y
121 CCCGGACAAA GGCTTGAGTG GATGGGATGG ATCAACGCTG GCAATGGTAA CACAATATAT
        S   Q   K   F   Q   A   R   V   T   I   T   R   D   T   S   A   S   T   A   Y
181 TCACAGAAGT TCCAGGCCAG AGTCACCATT ACCAGGGACA CGTCCGCGAG CACAGCCTAC
        M   E   L   S   S   L   R   S   E   D   T   A   V   Y   Y   C   A   R   W   V
241 ATGGAGCTGA GCAGCCTGAG ATCTGAAGAC ACGGCTGTGT ATTACTGTGC GAGATGGGTA
        G   G   V   A   S   Y   F   D   Y   W   G   Q   G   T   L   V   T   V   S   S
301 GGAGGGGTGG CCTCGTACTT TGACTACTGG GGCCAGGGGA CCCTGGTCAC CGTCTCCTCA

1 CAAGTGCAGC TGTTGGAGTC TGGGGCTGAG GTGAAGAAGC CTGGGGCCTC AGTGAAGGTT
 61 TCCTGCAAGG CTTCTGGATA CACCTTCACT AGCTATGCTA TGCATTGGGT GCGCCAGGCC
121 CCCGGACAAA GGCTTGAGTG GATGGGATGG ATCAACGCTG GCAATGGTAA CACAATATAT
181 TCACAGAAGT TCCAGGCCAG AGTCACCATT ACCAGGGACA CGTCCGCGAG CACAGCCTAC
241 ATGGAGCTGA GCAGCCTGAG ATCTGAAGAC ACGGCTGTGT ATTACTGTGC GAGATGGGTA
301 GGAGGGGTGG CCTCGTACTT TGACTACTGG GGCCAGGGGA CCCTGGTCAC CGTCTCCTCA

```
        E   I   V   L   T   Q   S   P   L   S   L   S   V   T   P   G   E   P   A   S
  1 GAAATTGTAT TGACACAGTC TCCACTCTCC CTGTCCGTCA CCCCTGGAGA GCCGGCCTCC
        I   S   C   R   S   S   Q   S   L   L   H   R   N   G   Y   N   Y   F   D   W
 61 ATCTCCTGCA GGTCTAGTCA GAGCCTCCTG CATAGAAATG GATACAATTA TTTTGATTGG
        Y   L   Q   Q   P   G   Q   S   P   Q   L   L   I   Y   L   G   S   N   R   A
121 TACCTGCAGC AGCCAGGGCA GTCTCCACAG CTCCTGATCT ATTTGGGTTC TAATCGGGCC
        S   G   V   P   D   R   F   S   G   S   G   S   G   T   D   F   T   L   K   I
181 TCCGGGGTCC CTGACAGGTT CAGTGGCAGT GGATCAGGCA CAGATTTTAC ACTGAAAATC
        S   R   V   E   A   E   D   V   G   V   Y   Y   C   M   Q   A   L   Q   T   P
241 AGCAGAGTGG AGGCTGAGGA TGTTGGGGTT TATTACTGCA TGCAAGCTCT ACAAACTCCG
        Y   T   F   G   Q   G   T   K   L   E   I   K
301 TACACTTTTG GCCAGGGGAC CAAGCTGGAG ATCAAA

1 GAAATTGTAT TGACACAGTC TCCACTCTCC CTGTCCGTCA CCCCTGGAGA GCCGGCCTCC
 61 ATCTCCTGCA GGTCTAGTCA GAGCCTCCTG CATAGAAATG GATACAATTA TTTTGATTGG
121 TACCTGCAGC AGCCAGGGCA GTCTCCACAG CTCCTGATCT ATTTGGGTTC TAATCGGGCC
181 TCCGGGGTCC CTGACAGGTT CAGTGGCAGT GGATCAGGCA CAGATTTTAC ACTGAAAATC
241 AGCAGAGTGG AGGCTGAGGA TGTTGGGGTT TATTACTGCA TGCAAGCTCT ACAAACTCCG
301 TACACTTTTG GCCAGGGGAC CAAGCTGGAG ATCAAA

```
      Q   V   Q   L       L   E   S       G   A   E       V   K   K       P   G   A   S       V   K   V
  1 CAAGTGCAGC TGTTGGAGTC TGGGGCTGAG GTGAAGAAGC CTGGGGCCTC AGTGAAGGTC
      S   C   E   A   S   G   Y       T   F   T       S   S   D       I   N   W   V       R   Q   A
 61 TCCTGCGAGG CTTCTGGATA CACCTTCACC AGTTCTGATA TCAACTGGGT GCGACAGGCC
      T   G   Q   G       L   E   W       M   G   W       M   N   P   N       S   G   N       T   G   Y
121 ACTGGACAAG GGCTTGAGTG GATGGGATGG ATGAACCCTA ATAGTGGTAA CACAGGCTAT
      A   Q   K   F       Q   G   R       V   T   M       T   R   N   T       S   I   S       T   A   Y
181 GCACAGAAGT TCCAGGGCAG AGTCACCATG ACCAGGAACA CCTCCATAAG CACAGCCTAC
      M   E   L   S       S   L   R       S   E   D       T   A   V   Y       Y   C   A       R   E   R
241 ATGGAGCTGA GCAGCCTGAG ATCTGAGGAC ACGGCCGTGT ATTACTGTGC GAGAGAAAGA
      P   R   R   R       G   G   G       F   D   I       W   G   Q   G       T   M   V       T   V   S
301 CCCCGGAGGC GTGGGGGTGG TTTTGATATC TGGGGCCAAG GGACAATGGT CACCGTCTCT
      S
361 TCA

1 CAAGTGCAGC TGTTGGAGTC TGGGGCTGAG GTGAAGAAGC CTGGGGCCTC AGTGAAGGTC
 61 TCCTGCGAGG CTTCTGGATA CACCTTCACC AGTTCTGATA TCAACTGGGT GCGACAGGCC
121 ACTGGACAAG GGCTTGAGTG GATGGGATGG ATGAACCCTA ATAGTGGTAA CACAGGCTAT
181 GCACAGAAGT TCCAGGGCAG AGTCACCATG ACCAGGAACA CCTCCATAAG CACAGCCTAC
241 ATGGAGCTGA GCAGCCTGAG ATCTGAGGAC ACGGCCGTGT ATTACTGTGC GAGAGAAAGA
301 CCCCGGAGGC GTGGGGGTGG TTTTGATATC TGGGGCCAAG GGACAATGGT CACCGTCTCT
361 TCA

```
        Q   V   Q   L   Q   Q   S   G   A   E   V   K   K   P   G   A   S   V   K   V
  1 CAGGTACAGC TGCAGCAGTC TGGGGCTGAG GTGAAGAAGC CTGGGGCCTC AGTGAAGGTC
        S   C   E   A   S   G   Y   T   F   T   S   S   D   I   N   W   V   R   Q   A
 61 TCCTGCGAGG CTTCTGGATA CACCTTCACC AGTTCTGATA TCAACTGGGT GCGACAGGCC
        T   G   Q   G   L   E   W   M   G   W   M   N   P   K   S   G   N   T   G   Y
121 ACTGGACAAG GGCTTGAGTG GATGGGATGG ATGAACCCTA AAAGTGGTAA CACAGGCTAT
        A   Q   K   F   Q   G   R   V   T   M   T   R   N   T   S   I   S   T   A   Y
181 GCACAGAAGT TCCAGGGCAG AGTCACCATG ACCAGGAACA CCTCCATAAG CACAGCCTAC
        M   E   L   S   S   L   R   S   E   D   T   A   V   Y   Y   C   A   R   E   R
241 ATGGAGCTGA GCAGCCTGAG ATCTGAGGAC ACGGCCGTGT ATTACTGTGC GAGAGAAAGA
        P   R   R   G   G   G   F   D   I   W   G   Q   G   T   M   V   T   V   S
301 CCCCGGAGGC GTGGGGGTGG TTTTGATATC TGGGGCCAAG GGACAATGGT CACCGTCTCT
        S
361 TCA

1 CAGGTACAGC TGCAGCAGTC TGGGGCTGAG GTGAAGAAGC CTGGGGCCTC AGTGAAGGTC
 61 TCCTGCGAGG CTTCTGGATA CACCTTCACC AGTTCTGATA TCAACTGGGT GCGACAGGCC
121 ACTGGACAAG GGCTTGAGTG GATGGGATGG ATGAACCCTA AAAGTGGTAA CACAGGCTAT
181 GCACAGAAGT TCCAGGGCAG AGTCACCATG ACCAGGAACA CCTCCATAAG CACAGCCTAC
241 ATGGAGCTGA GCAGCCTGAG ATCTGAGGAC ACGGCCGTGT ATTACTGTGC GAGAGAAAGA
301 CCCCGGAGGC GTGGGGGTGG TTTTGATATC TGGGGCCAAG GGACAATGGT CACCGTCTCT
361 TCA

1 Q   V   Q   L   Q   Q   S   G   A   E   V   K   K   P   G   A   S   V   K   V
 21 S   C   E   A   S   G   Y   T   F   T   S   S   D   I   N   W   V   R   Q   A
 41 T   G   Q   G   L   E   W   M   G   W   M   N   P   K   S   G   N   T   G   Y
 61 A   Q   K   F   Q   G   R   V   T   M   T   R   N   T   S   I   S   T   A   Y
 81 M   E   L   S   S   L   R   S   E   D   T   A   V   Y   Y   C   A   R   E   R
101 P   R   R   G   G   G   F   D   I   W   G   Q   G   T   M   V   T   V   S
121 S
```

Underlined AA = different from 31F9

```
        D   I   R   M   T   Q   S   P   S   S   L   S   A   S   V   G   D   R   V   T
  1 GACATCCGGA TGACCCAGTC TCCATCCTCC CTGTCTGCAT CTGTAGGAGA CAGAGTCACC
        I   T   C   R   A   S   Q   G   I   S   N   Y   L   A   W   Y   Q   Q   K   P
 61 ATCACTTGCC GGGCGAGTCA GGGCATTAGC AATTATTTAG CCTGGTATCA GCAGAAACCA
        G   K   V   P   K   F   L   I   Y   A   A   S   T   L   Q   S   G   V   P   S
121 GGGAAAGTTC CTAAGTTCCT GATCTATGCT GCATCCACTT TGCAATCAGG GGTCCCATCT
        R   F   S   G   S   G   S   G   T   D   F   T   L   T   I   S   S   L   Q   P
181 CGGTTCAGTG GCAGTGGATC TGGGACAGAT TTCACTCTCA CCATCAGCAG CCTGCAGCCT
        E   D   V   A   T   Y   Y   C   Q   K   Y   N   S   A   P   W   T   F   G   Q
241 GAAGATGTTG CAACTTATTA CTGTCAGAAG TATAACAGTG CCCCGTGGAC GTTCGGCCAA
        G   T   K   V   E   I   K
301 GGGACCAAGG TGGAAATCAA A

1 GACATCCGGA TGACCCAGTC TCCATCCTCC CTGTCTGCAT CTGTAGGAGA CAGAGTCACC
 61 ATCACTTGCC GGGCGAGTCA GGGCATTAGC AATTATTTAG CCTGGTATCA GCAGAAACCA
121 GGGAAAGTTC CTAAGTTCCT GATCTATGCT GCATCCACTT TGCAATCAGG GGTCCCATCT
181 CGGTTCAGTG GCAGTGGATC TGGGACAGAT TTCACTCTCA CCATCAGCAG CCTGCAGCCT
241 GAAGATGTTG CAACTTATTA CTGTCAGAAG TATAACAGTG CCCCGTGGAC GTTCGGCCAA
301 GGGACCAAGG TGGAAATCAA A

```
              Q   V   Q   L   V   E   S       G   A   E       V   K   K   P       G   A   S       V   K   V
  1 CAAGTGCAGC TGGTGGAGTC TGGGGCTGAG GTGAAGAAGC CTGGGGCCTC AGTGAAGGTT
      S   C   K   A   S   G   Y   T   F   T       N   Y   Y   M   H   W   V       R   Q   A
 61 TCCTGCAAGG CATCTGGATA CACCTTCACC AACTACTATA TGCACTGGGT GCGACAGGCC
      P   G   Q   G       L   E   W   M   G   I       I   N   P   S   R   G   S       T   S   Y
121 CCTGGACAAG GGCTCGAGTG GATGGGAATA ATCAACCCTA GTAGAGGTAG CACAAGCTAC
      A   Q   K   F   Q   G   R   V   T   M       T   R   D   T       S   T   S       T   V   Y
181 GCACAGAAGT TCCAGGGCAG AGTCACCATG ACCAGGGACA CGTCCACGAG CACAGTCTAC
      M   E   L   S       S   L   R       S   E   D       T   A   V   Y   Y   C   A   R   R   Q
241 ATGGAGCTGA GCAGCCTGAG ATCTGAGGAC ACGGCCGTGT ATTACTGTGC GCGACGCCAG
      M   A   T   G   P   F   D   Y   W   G       Q   G   T   L   V   T   V       S   S
301 ATGGCTACAG GCCCCTTTGA CTACTGGGGC CAGGGAACCC TGGTCACCGT CTCCTCA

1 CAAGTGCAGC TGGTGGAGTC TGGGGCTGAG GTGAAGAAGC CTGGGGCCTC AGTGAAGGTT
 61 TCCTGCAAGG CATCTGGATA CACCTTCACC AACTACTATA TGCACTGGGT GCGACAGGCC
121 CCTGGACAAG GGCTCGAGTG GATGGGAATA ATCAACCCTA GTAGAGGTAG CACAAGCTAC
181 GCACAGAAGT TCCAGGGCAG AGTCACCATG ACCAGGGACA CGTCCACGAG CACAGTCTAC
241 ATGGAGCTGA GCAGCCTGAG ATCTGAGGAC ACGGCCGTGT ATTACTGTGC GCGACGCCAG
301 ATGGCTACAG GCCCCTTTGA CTACTGGGGC CAGGGAACCC TGGTCACCGT CTCCTCA

```
        D   I   V   L   T   Q   S   P   D   S   L   A   V   S   L   G   E   R   A   T
  1 GATATTGTGC TGACTCAGTC TCCAGACTCC CTGGCTGTGT CTCTGGGCGA GAGGGCCACC
        I   N   C   K   S   S   Q   S   V   L   Y   S   S   N   N   K   N   Y   L   A
 61 ATCAACTGCA AGTCCAGCCA GAGTGTTTTA TACAGCTCCA ACAATAAGAA CTACTTAGCT
        W   Y   Q   Q   K   P   G   Q   P   P   K   L   L   I   Y   W   A   S   T   R
121 TGGTACCAGC AGAAACCAGG ACAGCCTCCT AAGCTGCTCA TTTACTGGGC ATCTACCCGG
        E   S   G   V   P   D   R   F   S   G   S   G   S   G   T   D   F   T   L   T
181 GAATCCGGGG TCCCTGACCG ATTCAGTGGC AGCGGGTCTG GGACAGATTT CACTCTCACC
        I   S   S   L   Q   A   E   D   V   A   V   Y   Y   C   Q   Q   Y   Y   S   T
241 ATCAGCAGCC TGCAGGCTGA AGATGTGGCA GTTTATTACT GTCAGCAATA TTATAGTACT
        P   P   T   F   G   Q   G   T   K   L   E   I   K
301 CCTCCCACTT TTGGCCAGGG GACCAAGCTG GAGATCAAA
```

```
  1 GATATTGTGC TGACTCAGTC TCCAGACTCC CTGGCTGTGT CTCTGGGCGA GAGGGCCACC
 61 ATCAACTGCA AGTCCAGCCA GAGTGTTTTA TACAGCTCCA ACAATAAGAA CTACTTAGCT
121 TGGTACCAGC AGAAACCAGG ACAGCCTCCT AAGCTGCTCA TTTACTGGGC ATCTACCCGG
181 GAATCCGGGG TCCCTGACCG ATTCAGTGGC AGCGGGTCTG GGACAGATTT CACTCTCACC
241 ATCAGCAGCC TGCAGGCTGA AGATGTGGCA GTTTATTACT GTCAGCAATA TTATAGTACT
301 CCTCCCACTT TTGGCCAGGG GACCAAGCTG GAGATCAAA
```

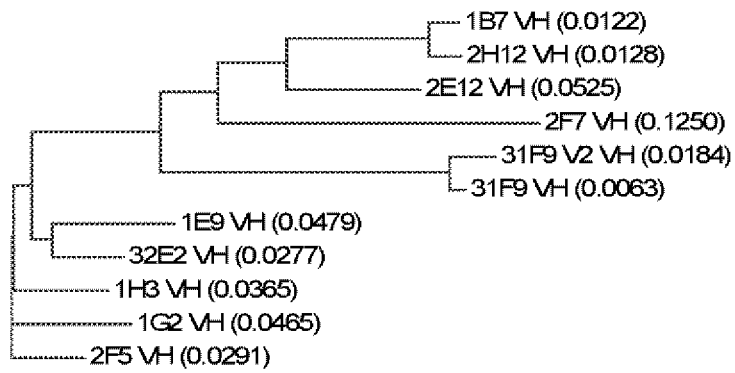

Alignment of VH Region

```
                    1                                                  50
   2E12 VH    (1)   QVQLLESGAEVKKPGASVKVSCKASGYTFTSYAMHWVRQAPGQRLEWMGW
    2F7 VH    (1)   EVQLLESGAEVKKPGASVKVSCKASGYIFSRYAIHWVRQAPGQGLEWMGW
31F9 V2 VH    (1)   QVQLQQSGAEVKKPGASVKVSCEASGYTFTSSDINWVRQATGQGLEWMGW
   31F9 VH    (1)   QVQLLESGAEVKKPGASVKVSCEASGYTFTSSDINWVRQATGQGLEWMGW
    1E9 VH    (1)   QVQLVESGAEVKKPGASVRVSCKASGYRFISYYMHWVRQAPGQGLEWMGI
    1B7 VH    (1)   QVQLVESGAEVKKPGASVKVSCKASGYTFTSYAIHWVRQAPGQRLEWMGW
   32E2 VH    (1)   QVQLVESGAEVKKPGASVKVSCKASGYTFTNYYMHWVRQAPGQGLEWMGI
    1H3 VH    (1)   QVQLVESGAEVKKPGASVKVSCKASGYTFARYYMHWVRQAPGQGPEWMGI
   2H12 VH    (1)   EVQLLESGAEVKKPGASVKVSCKASGYTFTSYAIHWVRQAPGQRLEWMGW
    1G2 VH    (1)   QVQLVESGAEVKKPGASVKMSCRASGYTFTRYYMHWVRQAPGQGLEWMGI
    2F5 VH    (1)   EVQLLESGAEVKKPGASVKVSCKASGYTFTRYYMHWVRQAPGQGLEWMGI
Consensus     (1)   QVQLLESGAEVKKPGASVKVSCKASGYTFTSY MHWVRQAPGQGLEWMGW 51                                                 100
   2E12 VH   (51)   INAGNGNTIYSQKFQARVTITRDTSASTAYMELSSLRSEDTAVYYCARWV
    2F7 VH   (51)   INPFNGFTKYSQKFQGRVALTRDRSATTGYMELSSLTSEDTAVYYCARLE
31F9 V2 VH   (51)   MNPKSGNTGYAQKFQGRVTMTRNTSISTAYMELSSLRSEDTAVYYCARER
   31F9 VH   (51)   MNPNSGNTGYAQKFQGRVTMTRNTSISTAYMELSSLRSEDTAVYYCARER
    1E9 VH   (51)   INPSGGSTSYAQKFQGRVTMTRDTSTSTIYMELSSLRSEDTAVYYCARR-
    1B7 VH   (51)   INAGNGYRKYSQKFQGRVTVTRDTSASTAYMELSSLRSEDTAVYYCARFE
   32E2 VH   (51)   INPSRGSTSYAQKFQGRVTMTRDTSTSTVYMELSSLRSEDTAVYYCARR-
    1H3 VH   (51)   INPSGGSTSYAQKFQGRVTVTRDTSTSTVYMELSSLRSEDTAVYYCARR-
   2H12 VH   (51)   INAGNGYRKYSQKFQGRVTVTRDTSASTAYMELSSLRSEDTAVYYCARFE
    1G2 VH   (51)   INPSAGSTSYAQKFQDRVTMTRDTSRSTVYMELSSLRSEDTAVYYCARR-
    2F5 VH   (51)   INPSSGSTSYAQKFQGRVTMTRDTSTSTVYMELSSLRSEDMAVYYCARR-
Consensus    (51)   INP  G T YAQKFQGRVTMTRDTS STAYMELSSLRSEDTAVYYCAR 101           121
   2E12 VH  (101)   -GGVASYFDYWGQGTLVTVSS
    2F7 VH  (101)   -SNKFYAFDIWGQGTMVTVSS
31F9 V2 VH  (101)   PRRRGGGFDIWGQGTMVTVSS
   31F9 VH  (101)   PRRRGGGFDIWGQGTMVTVSS
    1E9 VH  (100)   -NIVTGPFDYWGQGTLVTVSS
    1B7 VH  (101)   -GGMVTAMDFWGQGTLVTVSS
   32E2 VH  (100)   -QMATGPFDYWGQGTLVTVSS
    1H3 VH  (100)   -VVLGGPFDYWGQGTLVTVSS
   2H12 VH  (101)   -GGMVTAMDYWGQGTLVTVSS
    1G2 VH  (100)   -VVVGGPFDFWGQGTLVTVSS
    2F5 VH  (100)   -VVVGGPFDYWGQGTLVTVSS
Consensus   (101)      VGG FDYWGQGTLVTVSS
```

Figure 23

Alignment of VL Region

```
                    1                                                50
    1B7 VL    (1)   DVVMTQSPLSLPVTPGEPASISCRSSQSLLHR-NGYNYLDWYLQKPGQSP
   2H12 VL    (1)   DIQVTQSPLSLPVTPGEPASISCRSSQSLLHS-NGYNYLDWYLQKPGQSP
   2E12 VL    (1)   EIVLTQSPLSLSVTPGEPASISCRSSQSLLHR-NGYNYFDWYLQQPGQSP
    2F7 VL    (1)   EIVMTQSPLSLPVTPGEPASISCTSSQSLLHS-NGYNYLDWYLQKPGQSP
   31F9 VL    (1)   DIRMTQSPSSLSASVGDRVTITCRASQGISN------YLAWYQQKPGKVP
    1G2 VL    (1)   DIQMTQSPDSLAVSLGERATINCKSSQSVLYSPNKKNYLAWYQQKPGQPP
    1E9 VL    (1)   DVVMTQTPDSLAVSLGERATINCKSSQSVLYISNNKNYLAWYQQKPGQPP
   32E2 VL    (1)   DIVLTQSPDSLAVSLGERATINCKSSQSVLYSSNNKNYLAWYQQKPGQPP
    1H3 VL    (1)   DIRVTQSPDSLAVSLGERATINCKSSQSVLYSSNNKNYLAWYQQKPGQPP
    2F5 VL    (1)   DIQLTQSPDSLAVSLGERATINCKSSQSILYSSNNKNYLAWYQQKPGQPP
 Consensus    (1)   DIVMTQSPDSLAVSLGERATINCKSSQSLLYS N KNYLAWYQQKPGQPP 51                                               100
    1B7 VL   (50)   QLLIYLGSNRASGVPDRFSGSGSGTDFTLKISRVEAEDVGVYYCMQALQT
   2H12 VL   (50)   QLLIYLGSNRASGVPDRFSGSGSGTDFTLKISRVEAEDVGVYYCMQALQT
   2E12 VL   (50)   QLLIYLGSNRASGVPDRFSGSGSGTDFTLKISRVEAEDVGVYYCMQALQT
    2F7 VL   (50)   QLLIYLGSNRASGVPDRFSGSGSGTDFTLKISTVEAEDVGVYYCMQALQT
   31F9 VL   (45)   KFLIYAASTLQSGVPSRFSGSGSGTDFTLTISSLQPEDVATYYCQKYNSA
    1G2 VL   (51)   SLLFYWASTRESGVPDRFSGSGSGTDFTLTISSLQAEDVAVYYCQQYYST
    1E9 VL   (51)   KLLIYWASTRESGVPDRFSGSGSGTDFTLTISSLQAEDVAVYYCQHYYST
   32E2 VL   (51)   KLLIYWASTRESGVPDRFSGSGSGTDFTLTISSLQAEDVAVYYCQQYYST
    1H3 VL   (51)   KLLIYWASTRESGVPDRFSGSGSGTDFTLTISSLQAEDVAVYYCQQYYST
    2F5 VL   (51)   KLLIYWASTRESGVPDRFSGSGSGTDFTLTISSLQAEDVAVYYCQQYYST
 Consensus   (51)   KLLIYWASTRESGVPDRFSGSGSGTDFTLTISSLQAEDVAVYYCQQYYST 101        113
    1B7 VL  (100)   PFTFGPGTKVDIK
   2H12 VL  (100)   PFTFGPGIKVDIK
   2E12 VL  (100)   PYTFGQGTKLEIK
    2F7 VL  (100)   PWTFGQGTKVEIK
   31F9 VL   (95)   PWTFGQGTKVEIK
    1G2 VL  (101)   PPTFGQGTKVEIK
    1E9 VL  (101)   PPTFGQGTKLEIK
   32E2 VL  (101)   PPTFGQGTKLEIK
    1H3 VL  (101)   PPTFGQGTKVEIK
    2F5 VL  (101)   PPTFGQGTKVEIK
 Consensus  (101)   PPTFGQGTKVEIK
```

HUMAN MONOCLONAL ANTIBODIES TO GANGLIOSIDE GD2

CROSS-REFERENCE TO RELATED APPLICATION

This application is a divisional of application Ser. No. 14/730,036, filed Jun. 3, 2015, which claims the benefit of U.S. Ser. No. 62/007,874 filed Jun. 4, 2014, each of which the entire contents are incorporated herein by reference.

SEQUENCE LISTING

The instant application contains a Sequence Listing which has been submitted electronically in ASCII format and is hereby incorporated by reference in its entirety. The ASCII copy, created on Dec. 12, 2017, is named 12967-045-999_Sequence_Listing.txt and is 69,277 bytes in size.

BACKGROUND OF INVENTION

The present invention relates generally to antibodies directed against the disialoganglioside GD2. More specifically, this application relates to polynucleotides encoding human anti-GD2 antibodies and the corresponding encoded antibodies or fragment thereof, as well as to the use of such antibodies for diagnostic or therapeutic purposes. GD2 is attractive for tumor-specific therapies such as antibody therapy because of the tumor selective expression pattern. Currently, several anti-GD2 antibodies have been developed, such as murine anti-GD2 antibodies, human-mouse chimeric anti-GD2 antibodies. However, these antibodies still have undesirable immune effects. Thus, there remains a need to reduce the undesirable immune effects and enhance desirable antitumor effects of the anti-GD2 antibodies. This application discloses human monoclonal antibodies (mAbs) against GD2, which satisfy the need and provide related advantages.

SUMMARY OF INVENTION

In accordance with the present invention, herein provided are compositions for producing antibodies or functional fragments thereof that bind GD2. The compositions include an isolated polynucleotide encoding an antibody or a functional fragment thereof, wherein the antibody includes a variable heavy chain (VH) domain that has complementarity determining regions (VH CDR1, VH CDR2 and VH CDR3) provided herein. In one aspect, the isolated polynucleotide of the invention can also encode an antibody or a functional fragment thereof, wherein the antibody includes a VH domain that has an amino acid sequence provided herein. In another aspect, the isolated polynucleotide of the invention can also include a nucleic acid sequence provided herein, wherein the nucleic acid sequence encodes the VH domain of the antibody or functional fragment thereof.

In another embodiment of the invention, the isolated polynucleotide can encode an antibody or a functional fragment thereof, wherein the antibody includes a variable light chain (VL) domain that has complementarity determining regions (VL CDR1, VL CDR2 and VL CDR3) provided herein. In one aspect, the isolated polynucleotide of the invention can also encode an antibody or a functional fragment thereof, wherein the antibody includes a VL domain that has an amino acid sequence provided herein. In another aspect, the isolated polynucleotide of the invention can also include a nucleic acid sequence provided herein, wherein the nucleic acid sequence encodes the VL domain of the antibody or functional fragment thereof.

The compositions of the invention also include an isolated antibody or functional fragment thereof, wherein the antibody binds to GD2. In some embodiments, the invention provides an isolated antibody or functional fragment thereof that binds GD2, wherein the antibody or functional fragment thereof includes a VH domain having VH CDR1, VH CDR2, and VH CDR3 regions provided herein. In other embodiments, the invention provides an isolated antibody or functional fragment thereof that binds GD2, wherein the antibody or functional fragment thereof includes a VH domain having an amino acid sequence provided herein.

In some embodiments, the invention provides an isolated antibody or functional fragment thereof that binds GD2, wherein the antibody or functional fragment thereof includes a VL domain having VL CDR1, VL CDR2, and VL CDR3 regions provided herein. In other embodiments, the invention provides an isolated antibody or functional fragment thereof that binds GD2, wherein the antibody or functional fragment thereof includes a VL domain having an amino acid sequence provided herein.

In some embodiments, the invention provides an isolated antibody or functional fragment thereof that binds to GD2, wherein the antibody or functional fragment thereof includes both a VH domain and a VL domain, where the VH domain and the VL domain respectively include an amino acid sequence for the respective VH and VL domains of the clonal isolates provided herein.

In some embodiments, the invention provides a conjugate having an antibody or functional fragment provided herein that is conjugated or recombinantly fused to a diagnostic agent, detectable agent or therapeutic agent. In some aspects of the invention, a conjugate of the invention that includes a detectable agent can be used in a method for detecting and/or diagnosing tumor formation is a subject. Such methods can include administering an effective amount of the conjugate to a subject in need thereof.

In some embodiments, the invention provides pharmaceutical compositions having one or more antibody or functional fragment of the invention and a pharmaceutically acceptable carrier. In some aspects, the invention also provides a method for treating or preventing a disease in a subject in need thereof, by administering a therapeutically effective amount of a pharmaceutical composition of the invention. In still another aspect, the invention provides administering a second therapeutic agent concurrently or successively with an antibody or functional fragment of the invention.

BRIEF DESCRIPTION OF THE DRAWINGS

FIG. 1 shows the nucleotide sequence and the encoded amino acid sequence of the variable heavy (VH) chain domain of clone 1B7. The top portion of the figure shows an alignment between the nucleotide sequence of SEQ ID NO: 1 and amino acid sequence of SEQ ID NO: 2. The three complementarity determining regions (VH CDR1, VH CDR2 and VH CDR3) are also identified.

Figure 2:
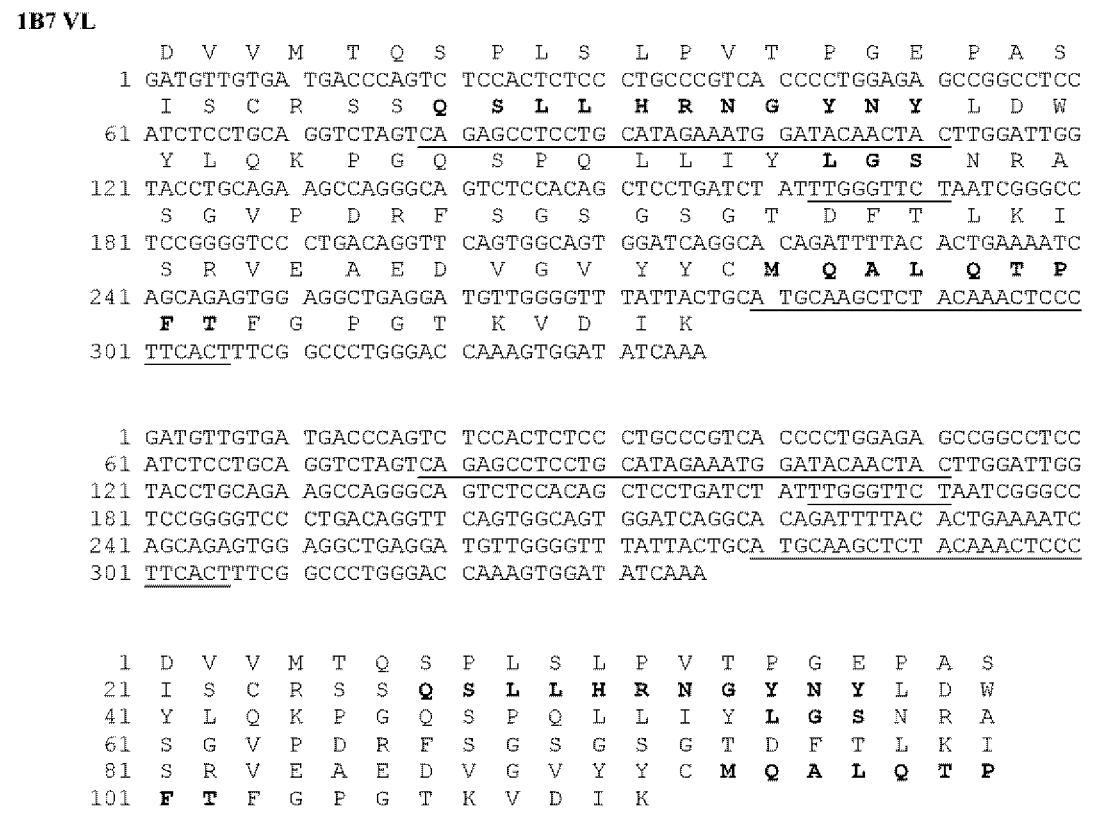

FIG. 2 shows the nucleotide sequence and the encoded amino acid sequence of the variable light (VL) chain domain of clone 1B7. The top portion of the figure shows an alignment between the nucleotide sequence of SEQ ID NO: 3 and amino acid sequence of SEQ ID NO: 4. The three complementarity determining regions (VL CDR1, VL CDR2 and VL CDR3) are also identified.

Figure 3:
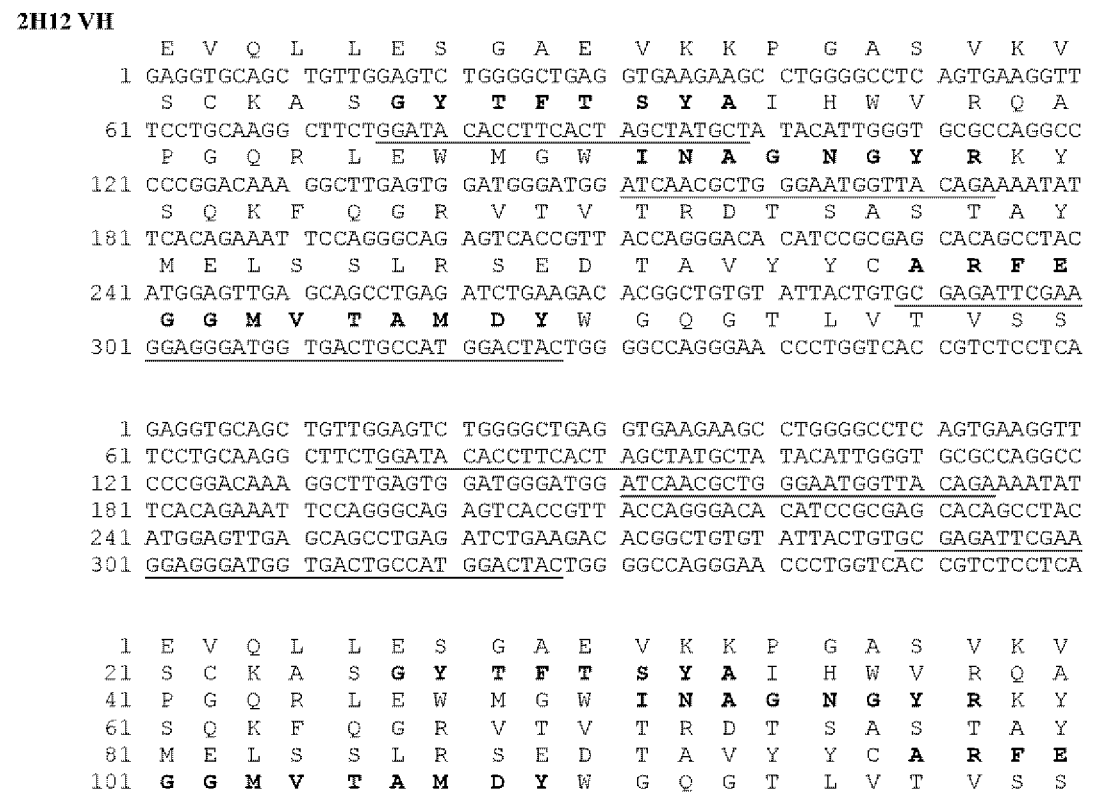

FIG. 3 shows the nucleotide sequence and the encoded amino acid sequence of the variable heavy (VH) chain domain of clone 2H12. The top portion of the figure shows an alignment between the nucleotide sequence of SEQ ID NO: 5 and amino acid sequence of SEQ ID NO: 6. The three complementarity determining regions (VH CDR1, VH CDR2 and VH CDR3) are also identified.

Figure 4:
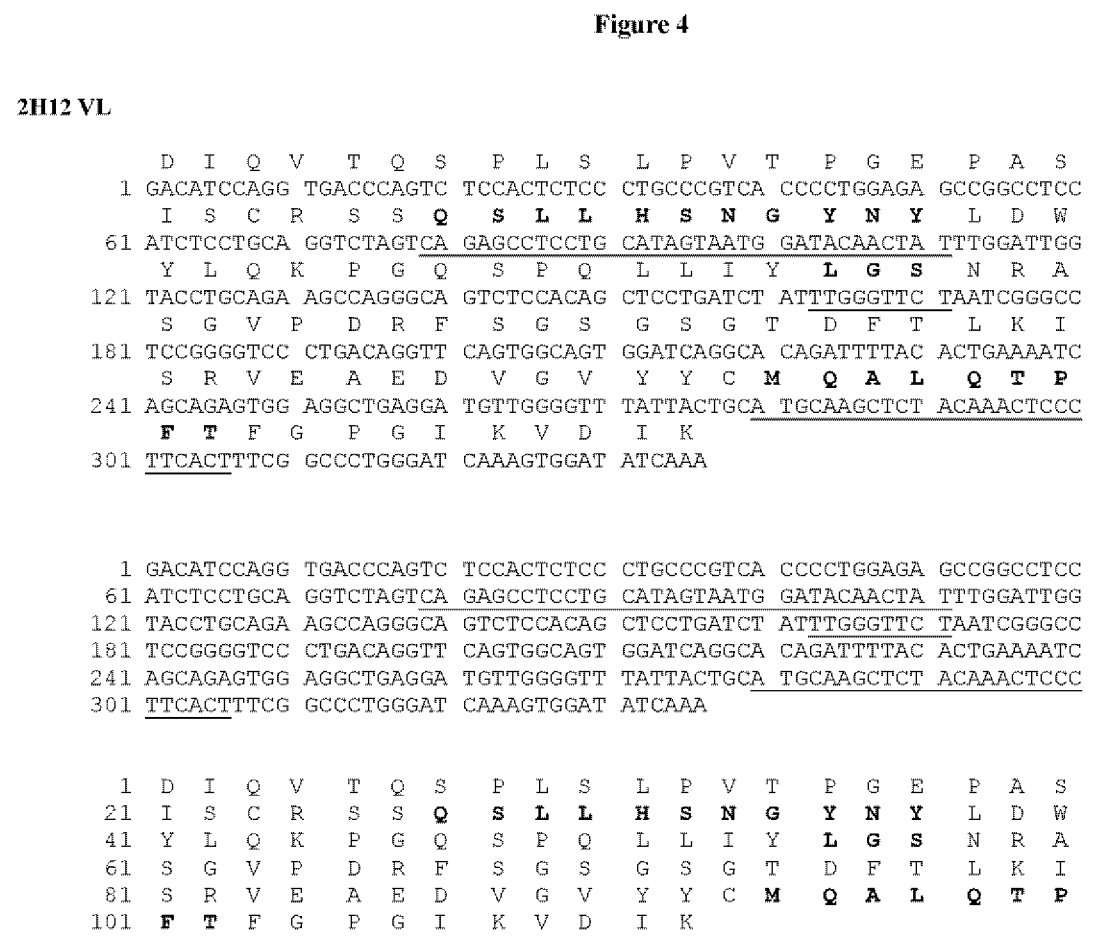

FIG. 4 shows the nucleotide sequence and the encoded amino acid sequence of the variable light (VL) chain domain of clone 2H12. The top portion of the figure shows an alignment between the nucleotide sequence of SEQ ID NO: 7 and amino acid sequence of SEQ ID NO: 8. The three complementarity determining regions (VL CDR1, VL CDR2 and VL CDR3) are also identified.

Figure 5:
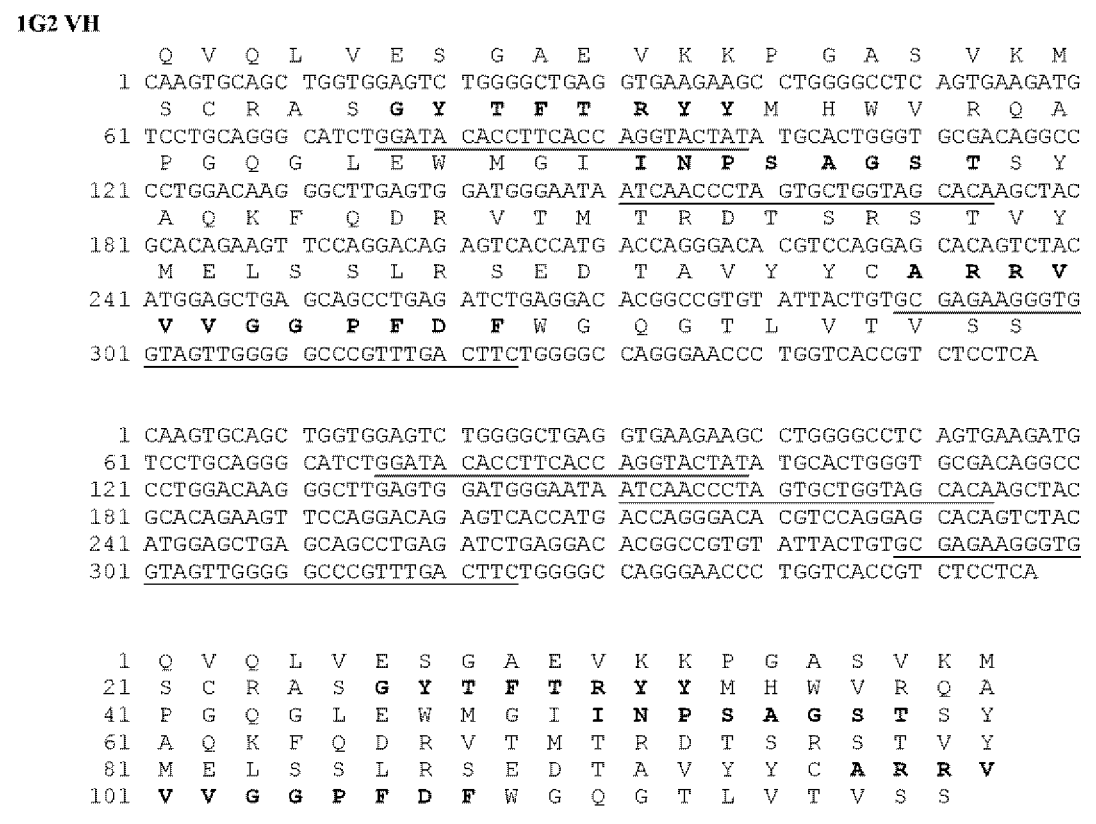

FIG. 5 shows the nucleotide sequence and the encoded amino acid sequence of the variable heavy (VH) chain domain of clone 1G2. The top portion of the figure shows an alignment between the nucleotide sequence of SEQ ID NO: 9 and amino acid sequence of SEQ ID NO: 10. The three complementarity determining regions (VH CDR1, VH CDR2 and VH CDR3) are also identified.

Figure 6:
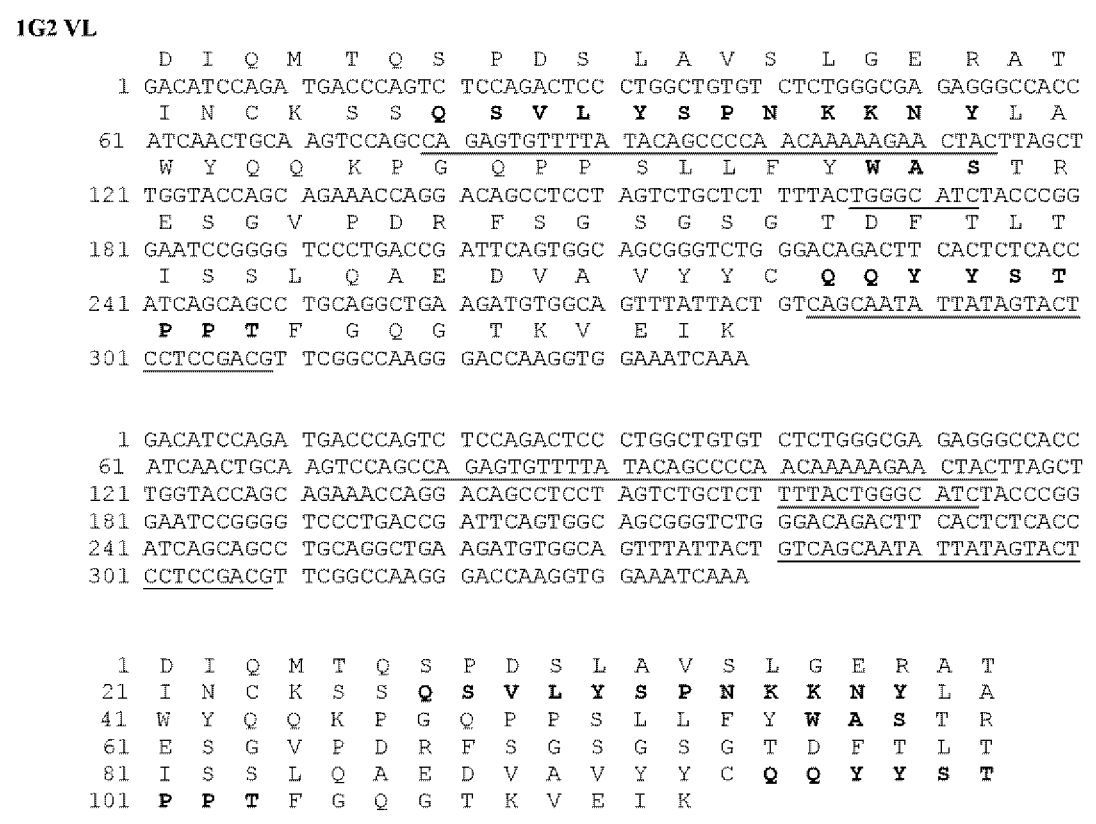

FIG. 6 shows the nucleotide sequence and the encoded amino acid sequence of the variable light (VL) chain domain of clone 1G2. The top portion of the figure shows an alignment between the nucleotide sequence of SEQ ID NO: 11 and amino acid sequence of SEQ ID NO: 12. The three complementarity determining regions (VL CDR1, VL CDR2 and VL CDR3) are also identified.

Figure 7:
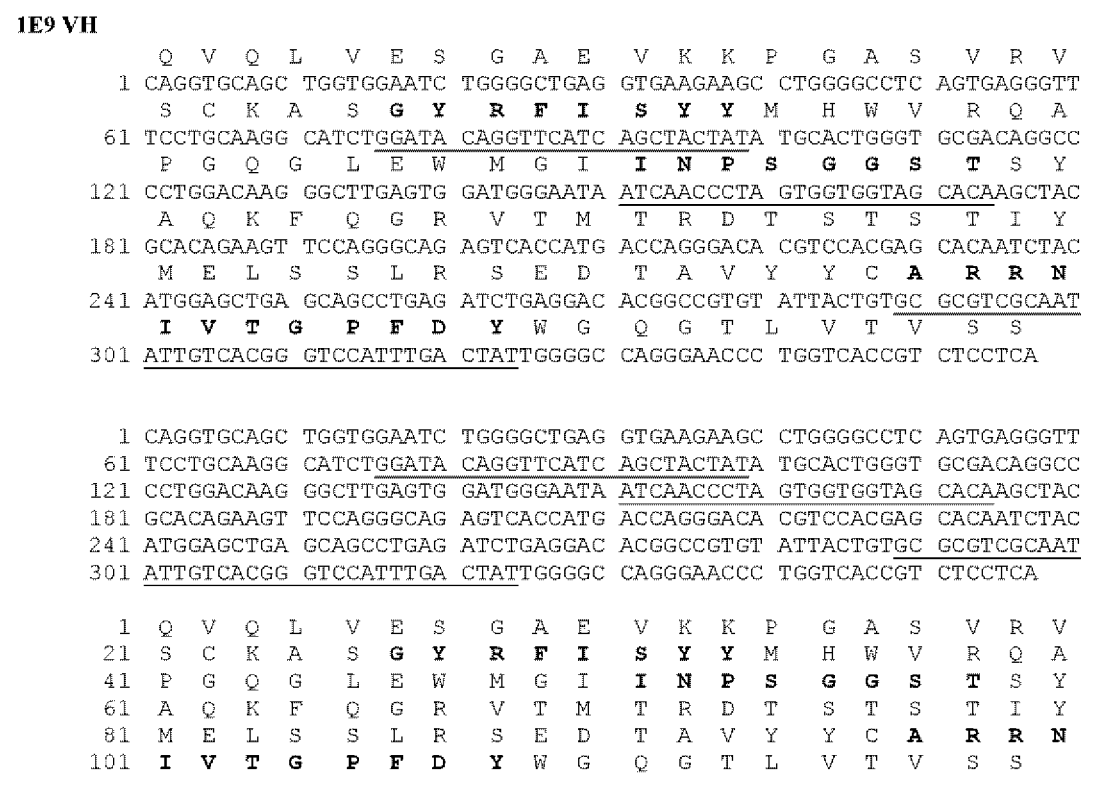

FIG. 7 shows the nucleotide sequence and the encoded amino acid sequence of the variable heavy (VH) chain domain of clone 1E9. The top portion of the figure shows an alignment between the nucleotide sequence of SEQ ID NO: 13 and amino acid sequence of SEQ ID NO: 14. The three complementarity determining regions (VH CDR1, VH CDR2 and VH CDR3) are also identified.

Figure 8:
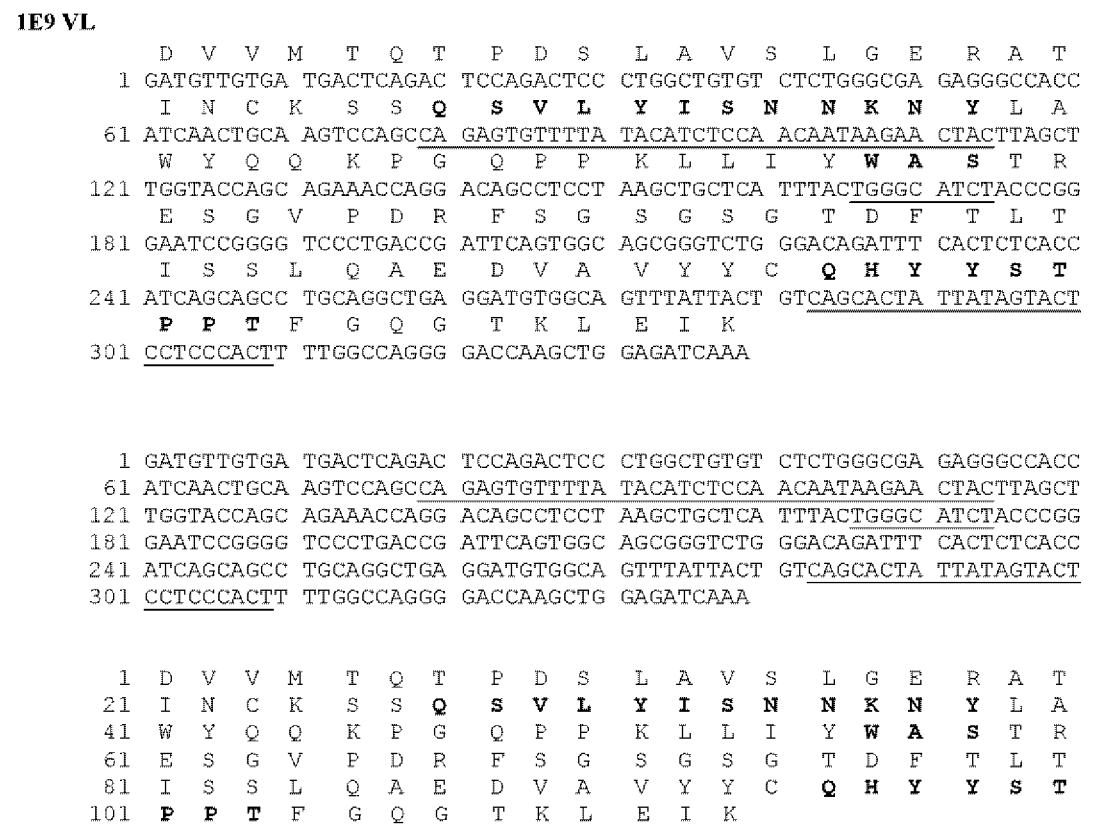

FIG. 8 shows the nucleotide sequence and the encoded amino acid sequence of the variable light (VL) chain domain of clone 1E9. The top portion of the figure shows an alignment between the nucleotide sequence of SEQ ID NO: 15 and amino acid sequence of SEQ ID NO: 16. The three complementarity determining regions (VL CDR1, VL CDR2 and VL CDR3) are also identified.

Figure 9:
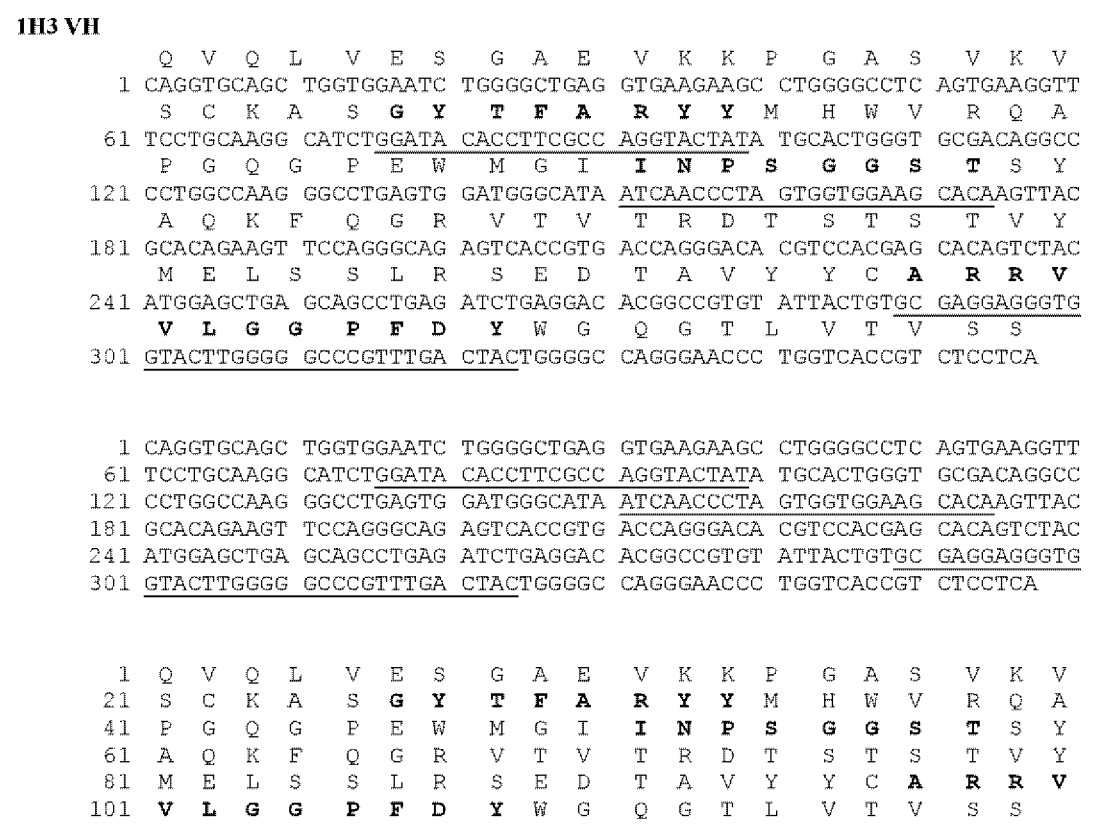

FIG. 9 shows the nucleotide sequence and the encoded amino acid sequence of the variable heavy (VH) chain domain of clone 1H3. The top portion of the figure shows an alignment between the nucleotide sequence of SEQ ID NO: 17 and amino acid sequence of SEQ ID NO: 18. The three complementarity determining regions (VH CDR1, VH CDR2 and VH CDR3) are also identified.

Figure 10:
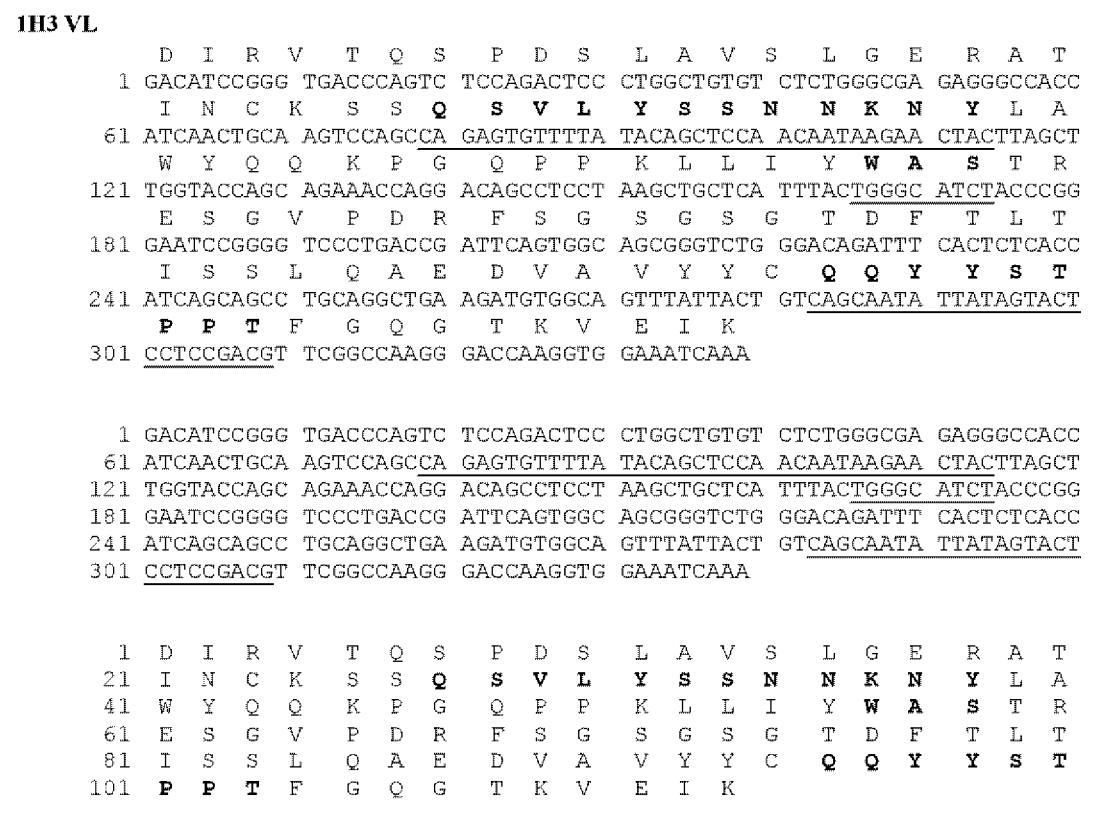

FIG. 10 shows the nucleotide sequence and the encoded amino acid sequence of the variable light (VL) chain domain of clone 1H3. The top portion of the figure shows an alignment between the nucleotide sequence of SEQ ID NO: 19 and amino acid sequence of SEQ ID NO: 20. The three complementarity determining regions (VL CDR1, VL CDR2 and VL CDR3) are also identified.

Figure 11:
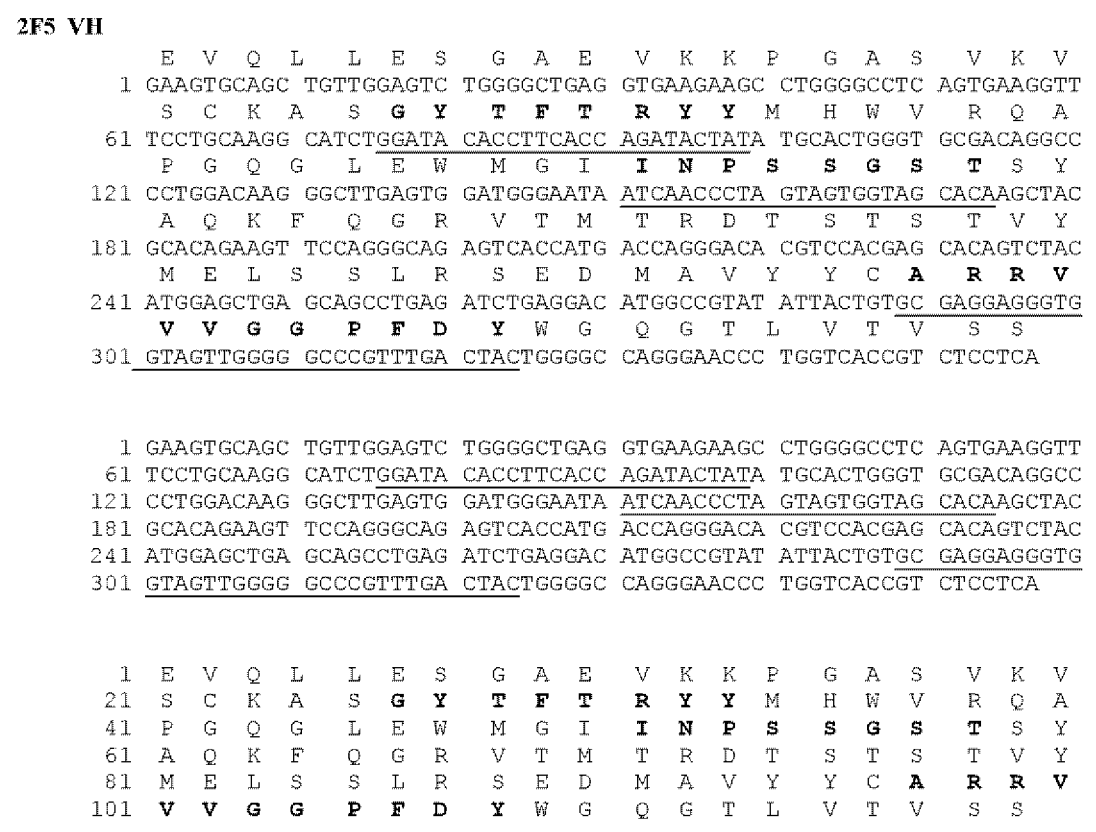

FIG. 11 shows the nucleotide sequence and the encoded amino acid sequence of the variable heavy (VH) chain domain of clone 2F5. The top portion of the figure shows an alignment between the nucleotide sequence of SEQ ID NO: 21 and amino acid sequence of SEQ ID NO: 22. The three complementarity determining regions (VH CDR1, VH CDR2 and VH CDR3) are also identified.

Figure 12:
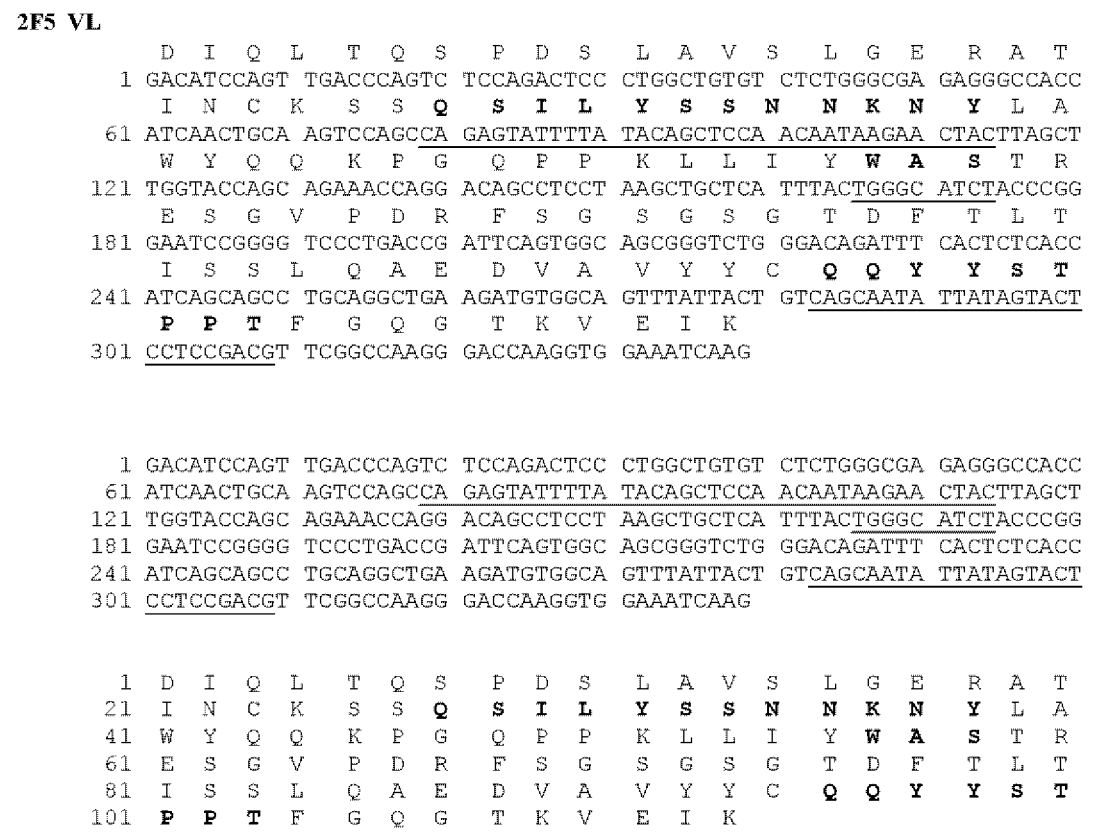

FIG. 12 shows the nucleotide sequence and the encoded amino acid sequence of the variable light (VL) chain domain of clone 2F5. The top portion of the figure shows an alignment between the nucleotide sequence of SEQ ID NO: 23 and amino acid sequence of SEQ ID NO: 24. The three complementarity determining regions (VL CDR1, VL CDR2 and VL CDR3) are also identified.

Figure 13:
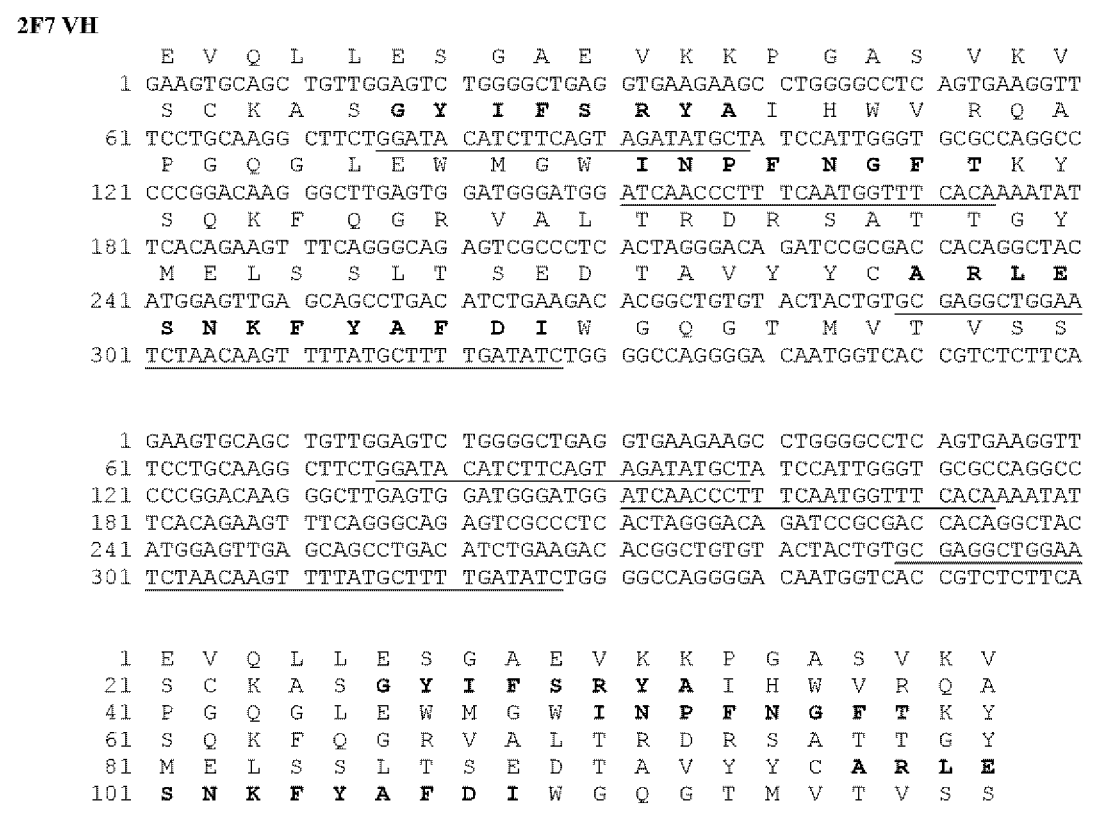

FIG. 13 shows the nucleotide sequence and the encoded amino acid sequence of the variable heavy (VH) chain domain of clone 2F7. The top portion of the figure shows an alignment between the nucleotide sequence of SEQ ID NO: 25 and amino acid sequence of SEQ ID NO: 26. The three complementarity determining regions (VH CDR1, VH CDR2 and VH CDR3) are also identified.

Figure 14:
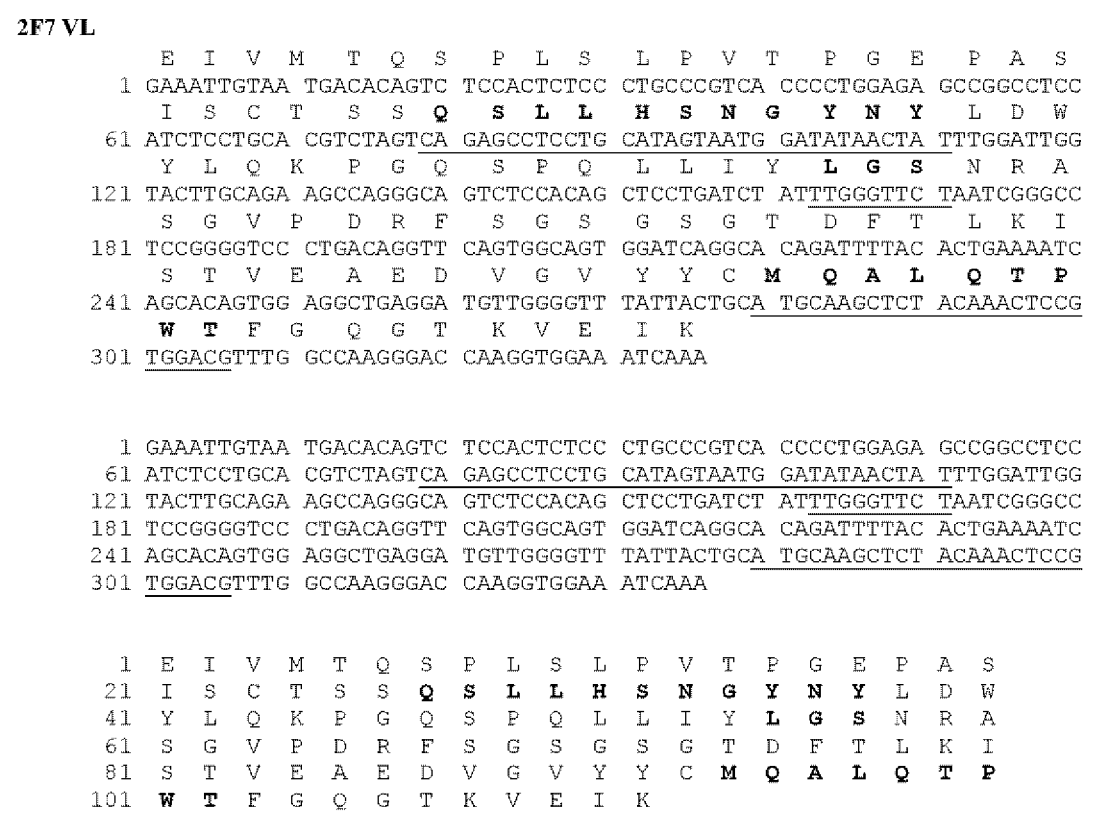

FIG. 14 shows the nucleotide sequence and the encoded amino acid sequence of the variable light (VL) chain domain of clone 2F7. The top portion of the figure shows an alignment between the nucleotide sequence of SEQ ID NO: 27 and amino acid sequence of SEQ ID NO: 28. The three complementarity determining regions (VL CDR1, VL CDR2 and VL CDR3) are also identified.

Figure 15:
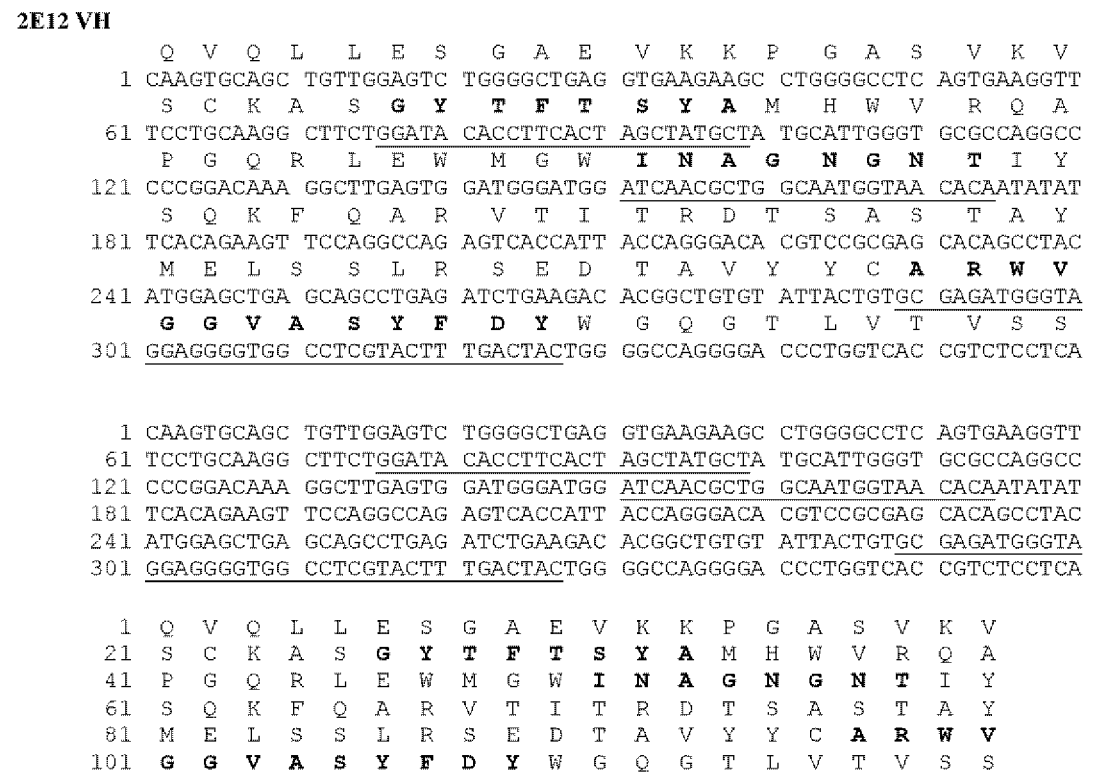

FIG. 15 shows the nucleotide sequence and the encoded amino acid sequence of the variable heavy (VH) chain domain of clone 2E12. The top portion of the figure shows an alignment between the nucleotide sequence of SEQ ID NO: 29 and amino acid sequence of SEQ ID NO: 30. The three complementarity determining regions (VH CDR1, VH CDR2 and VH CDR3) are also identified.

Figure 16:
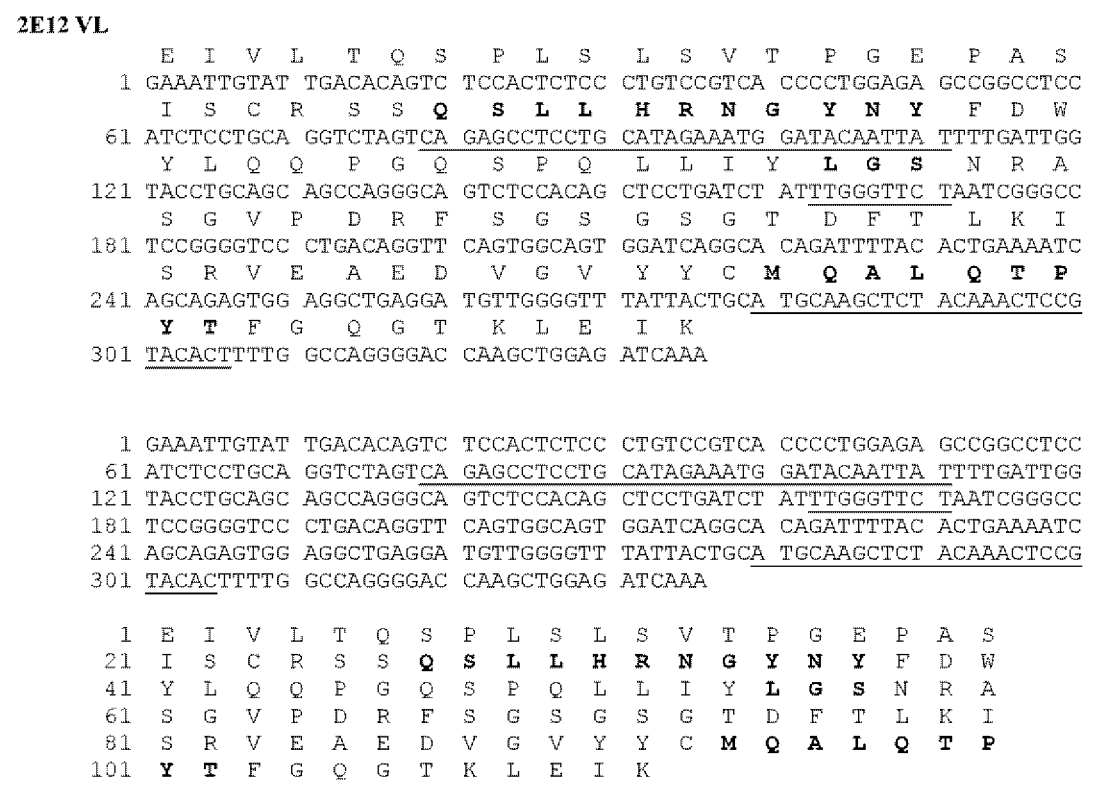

FIG. 16 shows the nucleotide sequence and the encoded amino acid sequence of the variable light (VL) chain domain of clone 2E12. The top portion of the figure shows an alignment between the nucleotide sequence of SEQ ID NO: 31 and amino acid sequence of SEQ ID NO: 32. The three complementarity determining regions (VL CDR1, VL CDR2 and VL CDR3) are also identified.

FIG. 17 shows the nucleotide sequence and the encoded amino acid sequence of the variable heavy (VH) chain domain of clone 31F9. The top portion of the figure shows an alignment between the nucleotide sequence of SEQ ID NO: 33 and amino acid sequence of SEQ ID NO: 34. The three complementarity determining regions (VH CDR1, VH CDR2 and VH CDR3) are also identified.

FIG. 18 shows the nucleotide sequence and the encoded amino acid sequence of the variable heavy (VH) chain domain of clone 31F9V2. The top portion of the figure shows an alignment between the nucleotide sequence of SEQ ID NO: 35 and amino acid sequence of SEQ ID NO: 36. The three complementarity determining regions (VH CDR1, VH CDR2 and VH CDR3) are also identified.

Figure 19:
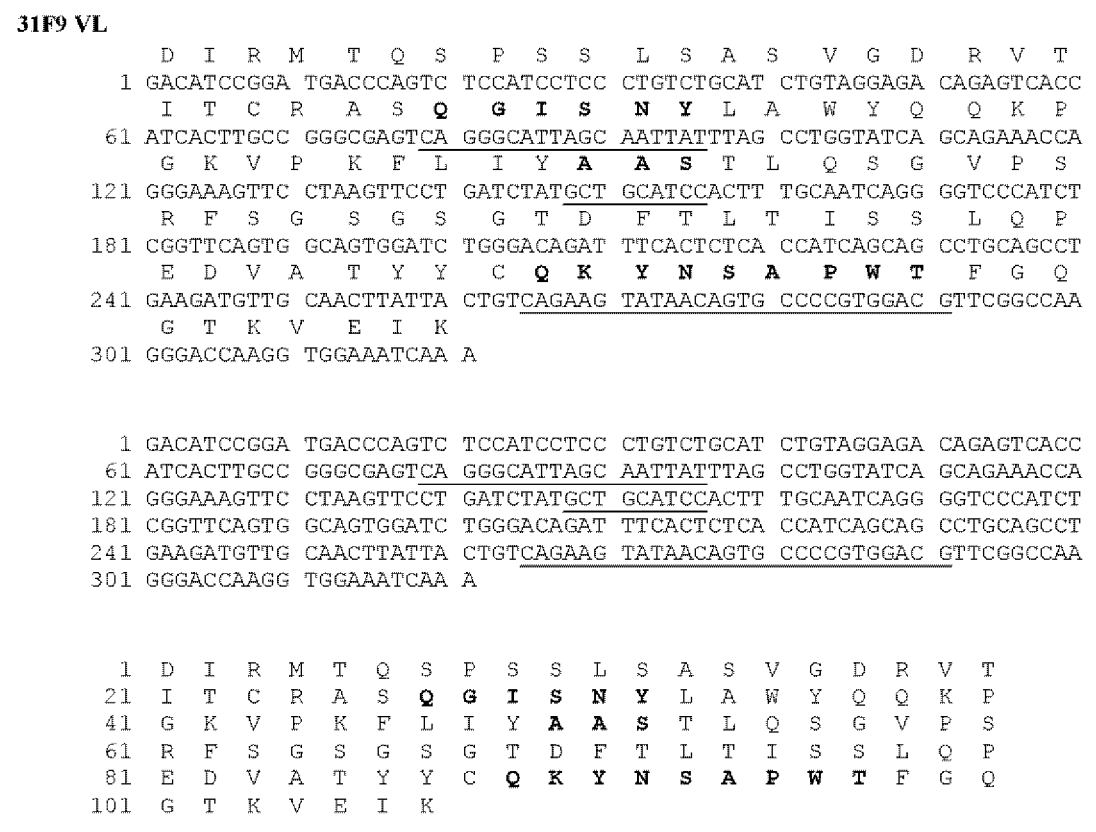

FIG. 19 shows the nucleotide sequence and the encoded amino acid sequence of the variable light (VL) chain domain of clone 31F9. The top portion of the figure shows an alignment between the nucleotide sequence of SEQ ID NO: 37 and amino acid sequence of SEQ ID NO: 38. The three complementarity determining regions (VL CDR1, VL CDR2 and VL CDR3) are also identified.

Figure 20:
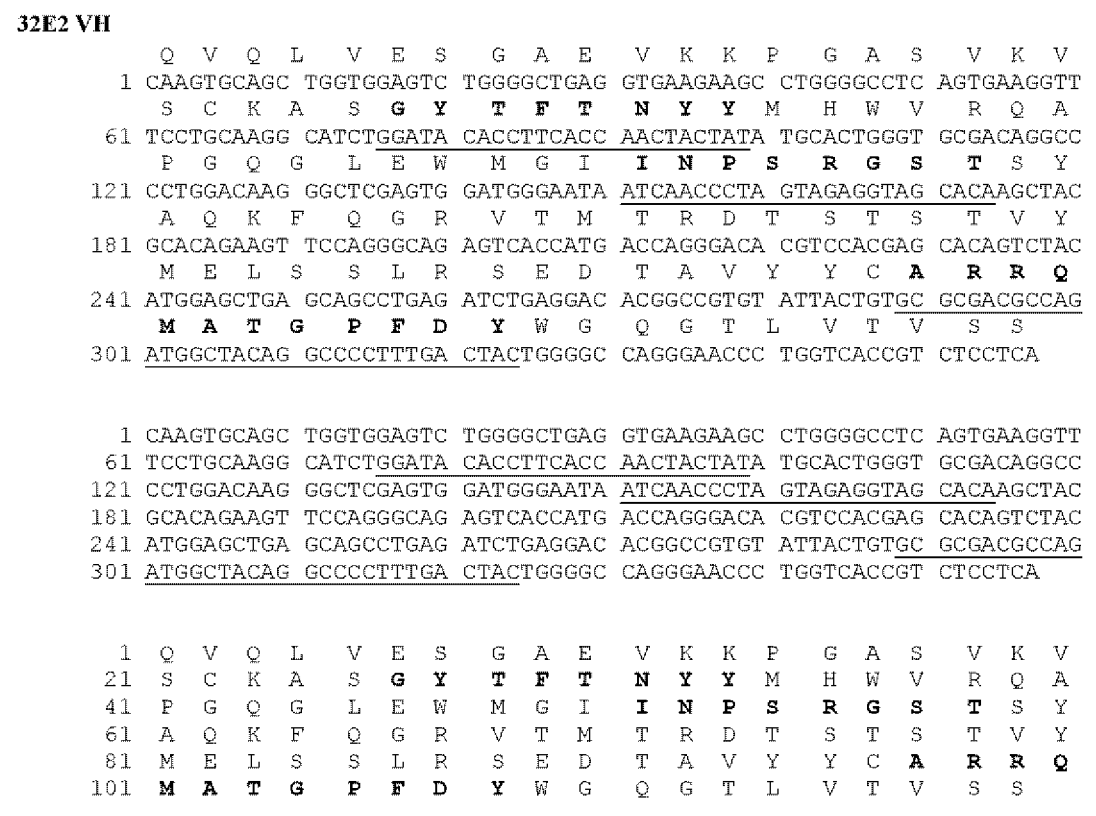

FIG. 20 shows the nucleotide sequence and the encoded amino acid sequence of the variable heavy (VH) chain domain of clone 32E2. The top portion of the figure shows an alignment between the nucleotide sequence of SEQ ID NO: 39 and amino acid sequence of SEQ ID NO: 40. The three complementarity determining regions (VH CDR1, VH CDR2 and VH CDR3) are also identified.

Figure 21:
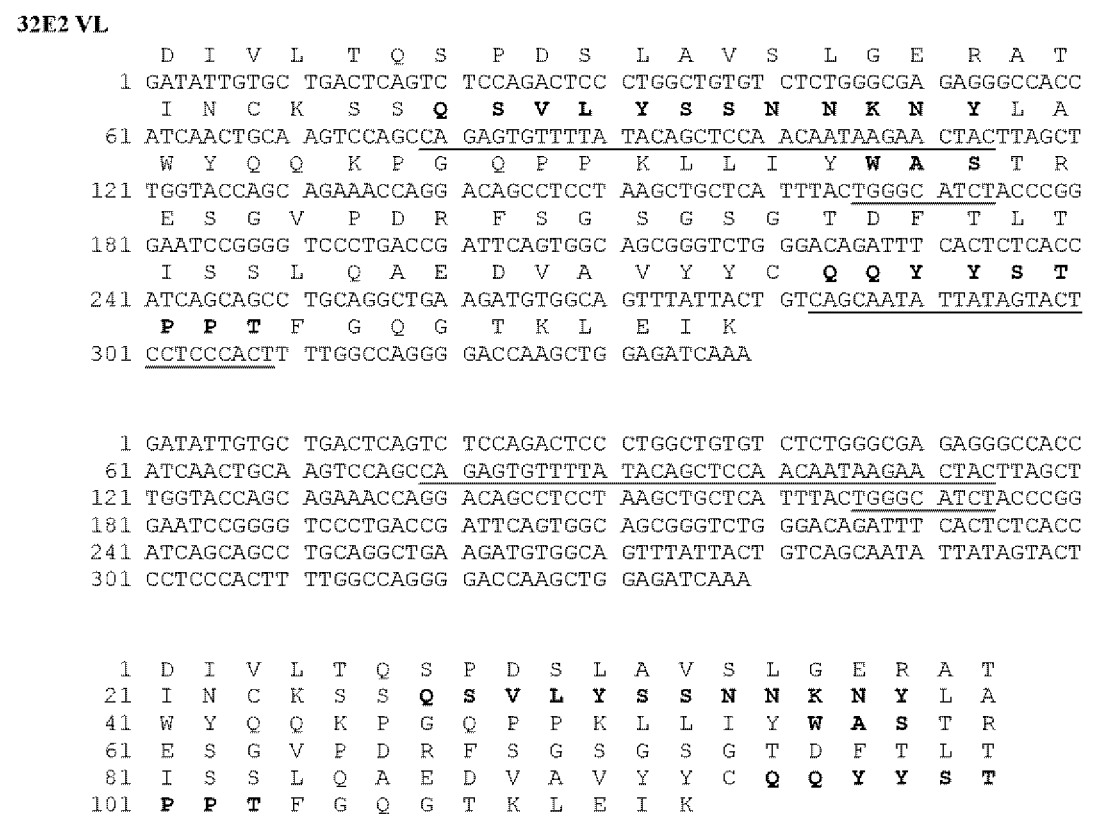

FIG. 21 shows the nucleotide sequence and the encoded amino acid sequence of the variable light (VL) chain domain of clone 32E2. The top portion of the figure shows an alignment between the nucleotide sequence of SEQ ID NO: 41 and amino acid sequence of SEQ ID NO: 42. The three complementarity determining regions (VL CDR1, VL CDR2 and VL CDR3) are also identified.

FIG. 22 shows an alignment of the VH regions of human anti-GD2 monoclonal antibodies 1B7 (SEQ ID NO: 2), 2H12 (SEQ ID NO: 6), 1G2 (SEQ ID NO: 10), 1E9 (SEQ ID NO: 14), 1H3 (SEQ ID NO: 18), 2F5 (SEQ ID NO: 22), 2F7 (SEQ ID NO: 26), 2E12 (SEQ ID NO: 30), 31F9 (SEQ ID NO: 34), 31F9V2 (SEQ ID NO: 36), and 32E2 (SEQ ID NO: 40), with the consensus sequence (SEQ ID NO: 43) listed below.

FIG. 23 shows an alignment of the VL regions of human anti-GD2 monoclonal antibodies 1B7 (SEQ ID NO: 4), 2H12 (SEQ ID NO: 8), 1G2 (SEQ ID NO: 12), 1E9 (SEQ ID NO: 16), 1H3 (SEQ ID NO: 20), 2F5 (SEQ ID NO: 24), 2F7 (SEQ ID NO: 28), 2E12 (SEQ ID NO: 32), 31F9 (SEQ ID NO: 38), and 32E2 (SEQ ID NO: 42), with the consensus sequence (SEQ ID NO: 44) listed below.

DETAILED DESCRIPTION OF THE INVENTION

Figure 24:
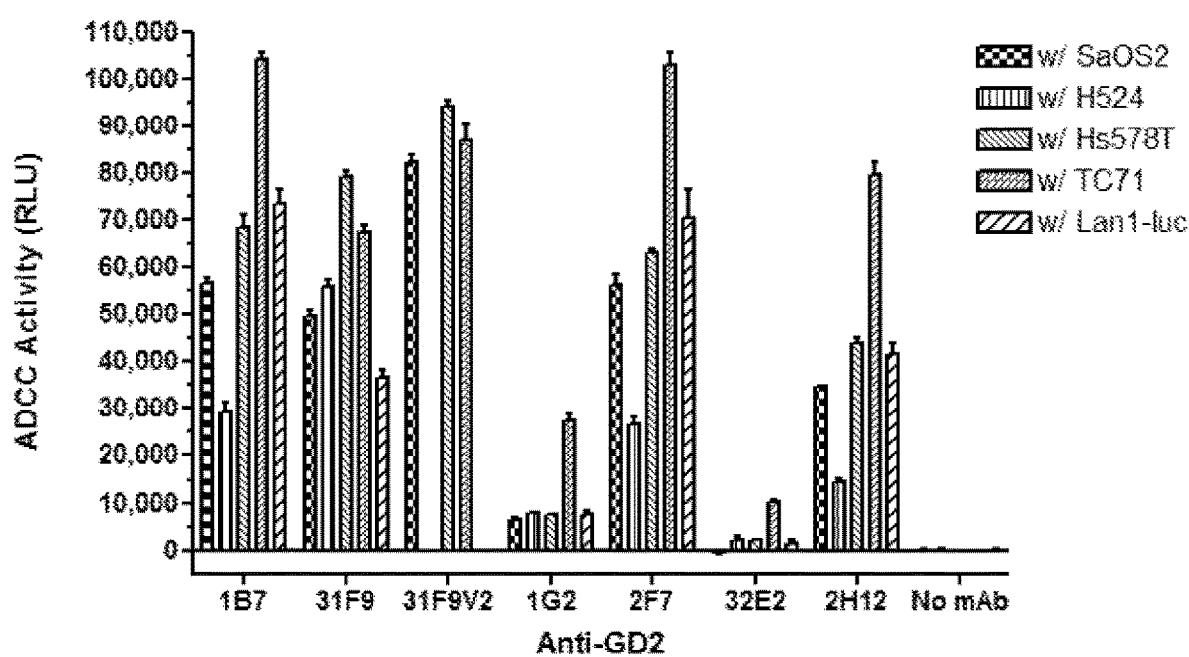
FIG. 24 shows antibody-dependent cell-mediated cytotoxicity (ADCC) of human anti-GD2 monoclonal antibodies 1B7, 31F9, 31F9V2, 1G2, 2F7, 32E2 and 2H12. The ADCC activities were measured by Promega's reporter assay using engineered Jurket cells as effector cells. Target cells are various tumor cells, including SaO52, H524, Hs578T, TC71, and Lan1-luc.

Gangliosides expressed on the tumor cell surface can be targets for cancer immunotherapy. The compositions provided herein are based, at least in part, on the identification and characterization of human antibodies that were generated from blood lymphocytes of individuals immunized with MabVax vaccines (MabVax Therapeutics, San Diego, Calif.) containing KLH-conjugated GD2L, GD3L and GM2 antigens as described, for example, in U.S. Pat. Nos. 6,936,253; 7,001,601, and 6,916,476. At least 11 antibodies with high affinity for GD2 (1B7, 2H12, 1G2, 1E9, 1H3, 2F5, 2F7, 2E12, 31F9, 31F9V2, and 32E2) were identified, expressed as recombinant antibodies, and further characterized in in vitro models. Of the eight antibodies tested, six (1B7, 2H12, 2F7, 2E12, 31F9V2, and 32E2) were potent in complement-dependent cytotoxicity (CDC) assays in at least one cancer cell line. All six antibodies tested show significant activity in antibody-dependent cytotoxicity assays with five different cancer cell lines, albeit to different degree. The two antibodies tested (1B7 and 31F9) also showed significantly anti-tumor activity in vivo, in both a survival model and a subcutaneous tumor model. The translational relevance of the invention provided herein is twofold: First, GD2-KLH conjugate vaccine can elicit an anti-GD2 IgG and IgM antibody response in cancer patients and antibody producing cells can be recovered from patient blood samples. Second, the most potent antibodies that were generated in a clinical trial can be preserved and ultimately used as therapeutics, or in the generation of therapeutics, for a target cancer population. The high affinity of the antibodies provided herein and their high effector functions support this translational potential.

As used herein, the term "antibody" is intended to mean a polypeptide product of B cells within the immunoglobulin class of polypeptides that is able to bind to a specific molecular antigen and is composed of two identical pairs of polypeptide chains, wherein each pair has one heavy chain (about 50-70 kDa) and one light chain (about 25 kDa) and each amino-terminal portion of each chain includes a variable region of about 100 to about 130 or more amino acids and each carboxy-terminal portion of each chain includes a constant region (See Borrebaeck (ed.) (1995) *Antibody Engineering*, Second Edition, Oxford University Press.; Kuby (1997) *Immunology*, Third Edition, W.H. Freeman and Company, New York). In the context of the present invention, the specific molecular antigen that can be bound by an antibody of the invention includes the target GD2.

The term "human" when used in reference to an antibody or a functional fragment thereof refers an antibody or functional fragment thereof that has a human variable region and/or a human constant region or a portion thereof corresponding to human germline immunoglobulin sequences. Such human germline immunoglobulin sequences are described by Kabat et al. (1991) *Sequences of Proteins of Immunological Interest*, Fifth Edition, U.S. Department of Health and Human Services, NIH Publication No. 91-3242. A human antibody, in the context of the present invention, can include an antibody that binds to GD2 and is encoded by a nucleic acid sequence that is a naturally occurring somatic variant of the human germline immunoglobulin nucleic acid sequence. Exemplary methods of producing human antibodies are provided in Example I, but any method well known to those skilled in the art can be used.

The term "monoclonal antibody" refers to an antibody that is the product of a single cell clone or hybridoma or a population of cells derived from a single cell. A monoclonal antibody also is intended to refer to an antibody produced by recombinant methods from heavy and light chain encoding immunoglobulin genes to produce a single molecular immunoglobulin species. Amino acid sequences for antibodies within a monoclonal antibody preparation are substantially homogeneous and the binding activity of antibodies within such a preparation exhibit substantially the same antigen binding activity. In contrast, polyclonal antibodies are obtained from different B cells within a population, which are a combination of immunoglobulin molecules that bind a specific antigen. Each immunoglobulin of the polyclonal antibodies can bind a different epitope of the same antigen. Methods for producing both monoclonal antibodies and polyclonal antibodies are well known in the art (Harlow and Lane., *Antibodies: A Laboratory Manual*, Cold Spring Harbor Laboratory Press (1989) and Borrebaeck (ed.), *Antibody Engineering: A Practical Guide*, W.H. Freeman and Co., Publishers, New York, pp. 103-120 (1991)).

As used herein, the term "functional fragment" when used in reference to an antibody is intended to refer to a portion of the antibody including heavy or light chain polypeptides that retains some or all of the binding activity as the antibody from which the fragment was derived. Such functional fragments can include, for example, an Fd, Fv, Fab, F(ab'), F(ab)$_2$, F(ab')2, single chain Fv (scFv), diabody, triabody, tetrabody and minibody. Other functional fragments can include, for example, heavy or light chain polypeptides, variable region polypeptides or CDR polypeptides or portions thereof so long as such functional fragments retain binding activity. Such antibody binding fragments can be found described in, for example, Harlow and Lane, *Antibodies: A Laboratory Manual*, Cold Spring Harbor Laboratory, New York (1989); Myers (ed.), *Molec. Biology and Biotechnology: A Comprehensive Desk Reference*, New York: VCH Publisher, Inc.; Huston et al., *Cell Biophysics*, 22:189-224 (1993); Plückthun and Skerra, *Meth. Enzymol.*, 178:497-515 (1989) and in Day, E. D., *Advanced Immunochemistry*, Second Ed., Wiley-Liss, Inc., New York, N.Y. (1990).

The term "heavy chain" when used in reference to an antibody refers to a polypeptide chain of about 50-70 kDa, wherein the amino-terminal portion includes a variable region of about 120 to 130 or more amino acids and a carboxy-terminal portion that includes a constant region. The constant region can be one of five distinct types, referred to as alpha ($\alpha$), delta ($\delta$), epsilon ($\varepsilon$), gamma ($\gamma$) and mu ($\mu$), based on the amino acid sequence of the heavy chain constant region. The distinct heavy chains differ in size: $\alpha$, $\delta$ and $\gamma$ contain approximately 450 amino acids, while $\mu$ and $\varepsilon$ contain approximately 550 amino acids. When combined with a light chain, these distinct types of heavy chains give rise to five well known classes of antibodies, IgA, IgD, IgE, IgG and IgM, respectively, including four subclasses of IgG, namely IgG1, IgG2, IgG3 and IgG4. A heavy chain can be a human heavy chain.

The term "light chain" when used in reference to an antibody refers to a polypeptide chain of about 25 kDa, wherein the amino-terminal portion includes a variable region of about 100 to about 110 or more amino acids and a carboxy-terminal portion that includes a constant region. The approximate length of a light chain is 211 to 217 amino acids. There are two distinct types, referred to as kappa ($\kappa$) of lambda ($\lambda$) based on the amino acid sequence of the constant domains. Light chain amino acid sequences are well known in the art. A light chain can be a human light chain.

The term "variable domain" or "variable region" refers to a portion of the light or heavy chains of an antibody that is generally located at the amino-terminal of the light or heavy chain and has a length of about 120 to 130 amino acids in the heavy chain and about 100 to 110 amino acids in the light chain, and are used in the binding and specificity of each particular antibody for its particular antigen. The variable domains differ extensively in sequence between different antibodies. The variability in sequence is concentrated in the CDRs while the less variable portions in the variable domain are referred to as framework regions (FR). The CDRs of the light and heavy chains are primarily responsible for the interaction of the antibody with antigen. Numbering of amino acid positions used herein is according to the EU Index, as in Kabat et al. (1991) *Sequences of proteins of immunological interest*. (U.S. Department of Health and Human Services, Washington, D.C.) 5th ed. A variable region can be a human variable region.

A CDR refers to one of three hypervariable regions (H1, H2 or H3) within the non-framework region of the immunoglobulin (Ig or antibody) VH $\beta$-sheet framework, or one of three hypervariable regions (L1, L2 or L3) within the non-framework region of the antibody VL $\beta$-sheet framework. Accordingly, CDRs are variable region sequences interspersed within the framework region sequences. CDR regions are well known to those skilled in the art and have been defined by, for example, Kabat as the regions of most hypervariability within the antibody variable (V) domains (Kabat et al., *J. Biol. Chem.* 252:6609-6616 (1977); Kabat, *Adv. Prot. Chem.* 32:1-75 (1978)). CDR region sequences also have been defined structurally by Chothia as those residues that are not part of the conserved $\beta$-sheet framework, and thus are able to adapt different conformations (Chothia and Lesk, *J. Mol. Biol.* 196:901-917 (1987)). Both terminologies are well recognized in the art. The positions of CDRs within a canonical antibody variable domain have been determined by comparison of numerous structures (Al-Lazikani et al., *J. Mol. Biol.* 273:927-948 (1997); Morea et al., *Methods* 20:267-279 (2000)). Because the number of residues within a hypervariable region varies in different antibodies, additional residues relative to the canonical positions are conventionally numbered with a, b, c and so forth next to the residue number in the canonical variable domain numbering scheme (Al-Lazikani et al., supra (1997)). Such nomenclature is similarly well known to those skilled in the art.

For example, CDRs defined according to either the Kabat (hypervariable) or Chothia (structural) designations, are set forth in the Table 1 below.

TABLE 1

CDR Definitions

| Kabat[1] | Chothia[2] | Loop Location | |
|---|---|---|---|
| V$_H$ CDR1 | 31-35 | 26-32 | linking B and C strands |
| V$_H$ CDR2 | 50-65 | 53-55 | linking C' and C" strands |
| V$_H$ CDR3 | 95-102 | 96-101 | linking F and G strands |
| V$_L$ CDR1 | 24-34 | 26-32 | linking B and C strands |
| V$_L$ CDR2 | 50-56 | 50-52 | linking C' and C" strands |
| V$_L$ CDR3 | 89-97 | 91-96 | linking F and G strands |

[1]Residue numbering follows the nomenclature of Kabat et al., supra
[2]Residue numbering follows the nomenclature of Chothia et al., supra One or more CDRs also can be incorporated into a molecule either covalently or noncovalently to make it an immunoadhesin. An immunoadhesin can incorporate the CDR(s) as part of a larger polypeptide chain, can covalently link the CDR(s) to another polypeptide chain, or can incorporate the CDR(s) noncovalently. The CDRs permit the immunoadhesin to bind to a particular antigen of interest.

As used herein, the term "isolated" when used in reference to an antibody, antibody functional fragment or polynucleotide is intended to mean that the referenced molecule is free of at least one component as it is found in nature. The term includes an antibody, antibody functional fragment or polynucleotide that is removed from some or all other components as it is found in its natural environment. Components of an antibody's natural environment include, for example, erythrocytes, leukocytes, thrombocytes, plasma, proteins, nucleic acids, salts and nutrients. Components of an antibody functional fragment's or polynucleotide's natural environment include, for example, lipid membranes, cell organelles, proteins, nucleic acids, salts and nutrients. An antibody, antibody functional fragment or polynucleotide of the invention can also be free or all the way to substantially free from all of these components or any other component of the cells from which it is isolated or recombinantly produced.

As used herein, "isotype" refers to the antibody class that is encoded by heavy chain constant region genes. The heavy chains of a given antibody or functional fragment determine the class of that antibody or functional fragment: IgM, IgG, IgA, IgD or IgE. Each class can have either κ or λ light chains. The term "subclass" refers to the minor differences in amino acid sequences of the heavy chains that differentiate the subclasses. In humans there are two subclasses of IgA (subclasses IgA1 and IgA2) and there are four subclasses of IgG (subclasses IgG1, IgG2, IgG3 and IgG4). Such classes and subclasses are well known to those skilled in art.

The terms "binds" or "binding" as used herein refer to an interaction between molecules to form a complex. Interactions can be, for example, non-covalent interactions including hydrogen bonds, ionic bonds, hydrophobic interactions, and/or van der Waals interactions. A complex can also include the binding of two or more molecules held together by covalent or non-covalent bonds, interactions or forces. Binding of an antibody or functional fragment thereof can be detected using, for example, an enzyme-linked immunosorbant assay, a method provided in Example I or any one of a number of methods that are well known to those skilled in the art.

The strength of the total non-covalent interactions between a single antigen-binding site on an antibody or functional fragment and a single epitope of a target molecule, such as GD2, is the affinity of the antibody or functional fragment for that epitope. The ratio of association ($k_1$) to dissociation ($k_{-1}$) of an antibody or functional fragment thereof to a monovalent antigen ($k_1/k_{-1}$) is the association constant K, which is a measure of affinity. The value of K varies for different complexes of antibody or functional fragment and antigen and depends on both $k_1$ and $k_{-1}$. The association constant K for an antibody or functional fragment of the invention can be determined using any method provided herein or any other method well known to those skilled in the art.

The affinity at one binding site does not always reflect the true strength of the interaction between an antibody or functional fragment and an antigen. When complex antigens containing multiple, repeating antigenic determinants, such as a polyvalent GD2, come in contact with antibodies containing multiple binding sites, the interaction of antibody or functional fragment with antigen at one site will increase the probability of a reaction at a second site. The strength of such multiple interactions between a multivalent antibody and antigen is called the avidity. The avidity of an antibody or functional fragment can be a better measure of its binding capacity than is the affinity of its individual binding sites. For example, high avidity can compensate for low affinity as is sometimes found for pentameric IgM antibodies, which can have a lower affinity than IgG, but the high avidity of IgM, resulting from its multivalence, enables it to bind antigen effectively.

The specificity of an antibody or functional fragment thereof refers to the ability of an individual antibody or functional fragment thereof to react with only one antigen. An antibody or functional fragment can be considered specific when it can distinguish differences in the primary, secondary or tertiary structure of an antigen or isomeric forms of an antigen. The antibody can be cross-reactive if the binding epitope is present on other antigens.

The term "polynucleotide" refers to a polymeric form of nucleotides of any length, either deoxyribonucleotides or ribonucleotides or analogs thereof. The sequence of a polynucleotide is composed of four nucleotide bases: adenine (A); cytosine (C); guanine (G); thymine (T); and uracil (U) for thymine when the polynucleotide is RNA. Thus, the terms "nucleotide sequence" or "nucleic acid sequence" is the alphabetical representation of a polynucleotide. A polynucleotide can include a gene or gene fragment (for example, a probe, primer, EST or SAGE tag), exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes and primers. Polynucleotide also refers to both double- and single-stranded molecules. Unless otherwise specified or required, any embodiment of this invention that is a polynucleotide encompasses both the double-stranded form and each of two complementary single-stranded forms known or predicted to make up the double-stranded form. It is understood that the isolated polynucleotides and nucleic acids described herein are directed to non naturally occurring polynucleotides and nucleic acids. Non-naturally occurring polynucleotides and nucleic acids can include, but not limit to, cDNA and chemically synthesized molecules.

The term "encode" or grammatical equivalents thereof as it is used in reference to polynucleotides refers to a polynucleotide in its native state or when manipulated by methods well known to those skilled in the art that can be transcribed to produce mRNA, which is then translated into a polypeptide and/or a fragment thereof. The antisense strand is the complement of such a polynucleotide, and the encoding sequence can be deduced therefrom.

The phrase "therapeutic agent" refers to any agent that can be used in the treatment, management or amelioration of a disease associated with expression of GD2 and/or a symptom related thereto. In certain embodiments, a therapeutic agent refers to an antibody or functional fragment of the invention. In other embodiments, a therapeutic agent refers to an agent other than an antibody or functional fragment of the invention. A therapeutic agent can be an agent which is well known to be useful for, or has been or is currently being used for the treatment, management or amelioration of a disease associated with expression of GD2 and/or one or more symptoms related thereto.

The phrase "diagnostic agent" refers to a substance administered to a subject that aids in the diagnosis of a disease. Such substances can be used to reveal, pinpoint, and/or define the localization of a disease causing process. In certain embodiments, a diagnostic agent includes a substance that is conjugated to an antibody or functional fragment of the invention, that when administered to a subject or contacted to a sample from a subject aids in the diagnosis of cancer or tumor formation.

The phrase "detectable agent" refers to a substance that can be used to ascertain the existence or presence of a desired molecule, such as an antibody or functional fragment of the invention, in a sample or subject. A detectable agent can be a substance that is capable of being visualized or a substance that is otherwise able to be determined and/or measured (e.g., by quantitation).

An "effective amount" is an amount sufficient to effect beneficial or desired results. An effective amount can be administered in one or more administrations, applications or dosages. Such delivery is dependent on a number of variables including the time period for which the individual dosage unit is to be used, the bioavailability of the agent, the route of administration, etc.

The phrase "therapeutically effective amount" as used herein refers to the amount of a therapeutic agent (e.g., an antibody or functional fragment provided herein or any other therapeutic agent provided herein) which is sufficient to reduce and/or ameliorate the severity and/or duration of a given disease and/or a symptom related thereto. A therapeutically effective amount of a therapeutic agent can be an amount necessary for the reduction or amelioration of the advancement or progression of a given disease, reduction or amelioration of the recurrence, development or onset of a given disease, and/or to improve or enhance the prophylactic or therapeutic effect of another therapy (e.g., a therapy other than the administration of an antibody or functional fragment provided herein).

The compound GD2, also known as GD2 ganglioside, ganglioside GD2, and ganglioside G2, is a disialoganglioside with a molecular formula of $C_{74}H_{134}N_4O_{32}$ and a molar mass of 1591.86 g/mol. Gangliosides are acidic glycosphingolipids found on the outer surface of most cell membranes. They can be targets for monoclonal antibodies (mAb) because of the high antigen density, lack of modulation, relative homogeneity in many tumors and the possibility of up-regulation by cytokines. Many tumors have abnormal glycolipid composition and structure. GD2 has been found in a wide spectrum of human tumors, including those of neuroectodermal or epithelial origin, virtually all melanomas, and approximately 50% of tumor samples from osteosarcoma and soft-tissue sarcoma.

In some embodiments, the invention provides an isolated polynucleotide encoding an antibody heavy or light chain or a functional fragment thereof, wherein the antibody heavy or light chain or functional fragment thereof encoded by the polynucleotide of the invention has one or more of the complementarity determining regions (CDRs) depicted in FIGS. 1-21 or listed in Table 2. An antibody or functional fragment thereof that includes one or more of the CDRs can specifically bind to GD2 as described herein. Specific binding to GD2 can include the specificity, affinity and/or avidity as provided in Example I for any of the antibodies provided herein. In some aspects, an antibody or functional fragment thereof encoded by the polynucleotides of the invention can include the complement dependent cytotoxicity (CDC) activity and/or antibody-dependent cell-mediated cytotoxicity (ADCC) activity of any one of the clonal isolates 1B7, 2H12, 1G2, 1E9, 1H3, 2F5, 2F7, 2E12, 31F9, 31F9V2 or 32E2 described herein. Methods for assessing the specificity, affinity and/or avidity of an antibody or functional fragment thereof are well known in the art and exemplary methods are provided herein.

In some embodiments, the antibody or functional fragment thereof of the invention includes less than six CDRs. In some embodiments, the antibody or functional fragment thereof includes one, two, three, four, or five CDRs selected from the group consisting of VH CDR1, VH CDR2, VH CDR3, VL CDR1, VL CDR2, and/or VL CDR3. In specific embodiments, the antibody or functional fragment thereof includes one, two, three, four, or five CDRs selected from the group consisting of VH CDR1, VH CDR2, VH CDR3, VL CDR1, VL CDR2, and/or VL CDR3 of clonal isolates 1B7, 2H12, 1G2, 1E9, 1H3, 2F5, 2F7, 2E12, 31F9, 31F9V2 or 32E2 described herein.

In some embodiments, the present invention provides an isolated polynucleotide encoding an antibody heavy chain or a functional fragment thereof, the antibody heavy chain or functional fragment thereof including a variable heavy chain (VH) domain having VH CDR1, VH CDR2 and VH CDR3 amino acid sequences, wherein the VH CDR1 amino acid sequence is selected from the group consisting of residues 26-33 of SEQ ID NO: 2; residues 26-33 of SEQ ID NO: 6; residues 26-33 of SEQ ID NO: 10; residues 26-33 of SEQ ID NO: 14; residues 26-33 of SEQ ID NO: 18; residues 26-33 of SEQ ID NO: 22; residues 26-33 of SEQ ID NO: 26; residues 26-33 of SEQ ID NO: 30; residues 26-33 of SEQ ID NO: 34; residues 26-33 of SEQ ID NO: 36; and residues 26-33 of SEQ ID NO: 40; the VH CDR2 amino acid sequence is selected from the group consisting of residues 51-58 of SEQ ID NO: 2; residues 51-58 of SEQ ID NO: 6; residues 51-58 of SEQ ID NO: 10; residues 51-58 of SEQ ID NO: 14; residues 51-58 of SEQ ID NO: 18; residues 51-58 of SEQ ID NO: 22; residues 51-58 of SEQ ID NO: 26; residues 51-58 of SEQ ID NO: 30; residues 51-58 of SEQ ID NO: 34; residues 51-58 of SEQ ID NO: 36; and residues 51-58 of SEQ ID NO: 40; and the VH CDR3 amino acid sequence is selected from the group consisting of residues 97-109 of SEQ ID NO: 2; residues 97-109 of SEQ ID NO: 6; residues 97-108 of SEQ ID NO: 10; residues 97-108 of SEQ ID NO: 14; residues 97-108 of SEQ ID NO: 18; residues 97-108 of SEQ ID NO: 22; residues 97-109 of SEQ ID NO: 26; residues 97-109 of SEQ ID NO: 30; residues 97-110 of SEQ ID NO: 34; residues 97-110 of SEQ ID NO: 36; and residues 97-108 of SEQ ID NO: 40.

In other embodiments, the present invention provides an isolated polynucleotide encoding an antibody heavy chain or a functional fragment thereof, the antibody heavy chain or functional fragment thereof including a variable heavy chain (VH) domain having VH CDR1, VH CDR2 and VH CDR3 amino acid sequences, wherein the VH CDR1 amino acid sequence is encoded by the nucleic acid sequence selected from the group consisting of residues 76-99 of SEQ ID NO: 1; residues 76-99 of SEQ ID NO: 5; residues 76-99 of SEQ ID NO: 9; residues 76-99 of SEQ ID NO: 13; residues 76-99 of SEQ ID NO: 17; residues 76-99 of SEQ ID NO: 21; residues 76-99 of SEQ ID NO: 25; residues 76-99 of SEQ ID NO: 29; residues 76-99 of SEQ ID NO: 33; residues 76-99 of SEQ ID NO: 35; residues 76-99 of SEQ ID NO: 39; the VH CDR2 amino acid sequence is encoded by the nucleic acid sequence selected from the group consisting of residues 151-174 of SEQ ID NO: 1; residues 151-174 of SEQ ID NO: 5; residues 151-174 of SEQ ID NO: 9; residues 151-174 of SEQ ID NO: 13; residues 151-174 of SEQ ID NO: 17; residues 151-174 of SEQ ID NO: 21; residues 151-174 of SEQ ID NO: 25; residues 151-174 of SEQ ID NO: 29; residues 151-174 of SEQ ID NO: 33; residues 151-174 of SEQ ID NO: 35; residues 151-174 of SEQ ID NO: 39; and the VH CDR3 amino acid sequence is encoded by the nucleic acid sequence selected from the group consisting of residues 289-327 of SEQ ID NO: 1; residues 289-327 of SEQ ID NO: 5; residues 289-324 of SEQ ID NO: 9; residues 289-324 of SEQ ID NO: 13; residues 289-324 of SEQ ID NO: 17; residues 289-324 of SEQ ID NO: 21; residues 289-327 of SEQ ID NO: 25; residues 289-327 of SEQ ID NO: 29; residues 289-330 of SEQ ID NO: 33; residues 289-330 of SEQ ID NO: 35; residues 289-324 of SEQ ID NO: 39.

In some embodiments, the present invention provides an isolated polynucleotide encoding an antibody heavy chain or a functional fragment thereof, wherein the antibody heavy chain or functional fragment includes a variable heavy (VH)

chain domain having the VH CDR1, VH CDR2 and VH CDR3 amino acid sequence of the clonal isolate 1B7, 2H12, 1G2, 1E9, 1H3, 2F5, 2F7, 2E12, 31F9, 31F9V2 or 32E2.

In some embodiments, the present invention provides an isolated polynucleotide encoding an antibody heavy chain or a functional fragment thereof, the antibody heavy chain or functional fragment thereof including a variable heavy (VH) chain domain, wherein the VH domain has VH CDR1, VH CDR2, and VH CDR3 amino acid sequences selected from the group consisting of residues 26-33, residues 51-58, and residues 97-109 of SEQ ID NO: 2; residues 26-33, residues 51-58, and residues 97-109 of SEQ ID NO: 6; residues 26-33, residues 51-58, and residues 97-108 of SEQ ID NO: 10; residues 26-33, residues 51-58, and residues 97-108 of SEQ ID NO: 14; residues 26-33, residues 51-58, and residues 97-108 of SEQ ID NO: 18; residues 26-33, residues 51-58, and residues 97-108 of SEQ ID NO: 22; residues 26-33, residues 51-58, and residues 97-109 of SEQ ID NO: 26; residues 26-33, residues 51-58, and residues 97-109 of SEQ ID NO: 30; residues 26-33, residues 51-58, and residues 97-110 of SEQ ID NO: 34; residues 26-33, residues 51-58, and residues 97-110 of SEQ ID NO: 36; and residues 26-33, residues 51-58, and residues 97-108 of SEQ ID NO: 40.

In other embodiments, the present invention provides an isolated polynucleotide encoding an antibody heavy chain or a functional fragment thereof, the antibody heavy chain or functional fragment thereof including a variable heavy (VH) chain domain, wherein the VH domain has VH CDR1, VH CDR2, and VH CDR3 amino acid sequences encoded by nucleic acid sequences selected from the group consisting of residues 76-99, residues 151-174, and residues 289-327 of SEQ ID NO: 1; residues 76-99, residues 151-174, and residues 289-327 of SEQ ID NO: 5; residues 76-99, residues 151-174, and residues 289-324 of SEQ ID NO: 9; residues 76-99, residues 151-174, and residues 289-324 of SEQ ID NO: 13; residues 76-99, residues 151-174, and residues 289-324 of SEQ ID NO: 17; residues 76-99, residues 151-174, and residues 289-324 of SEQ ID NO: 21; residues 76-99, residues 151-174, and residues 289-327 of SEQ ID NO: 25; residues 76-99, residues 151-174, and residues 289-327 of SEQ ID NO: 29; residues 76-99, residues 151-174, and residues 289-330 of SEQ ID NO: 33; residues 76-99, residues 151-174, and residues 289-330 of SEQ ID NO: 35; residues 76-99, residues 151-174, and residues 289-324 of SEQ ID NO: 39.

In another embodiment, the present invention provides an isolated polynucleotide encoding an antibody heavy chain or a functional fragment thereof, the antibody heavy chain or functional fragment thereof including a variable heavy (VH) chain domain, wherein the VH domain has an amino acid sequence is selected from the group consisting of SEQ ID NO: 2; SEQ ID NO: 6; SEQ ID NO: 10; SEQ ID NO: 14; SEQ ID NO: 18; SEQ ID NO: 22; SEQ ID NO: 26; SEQ ID NO: 30; SEQ ID NO: 34; SEQ ID NO: 36; and SEQ ID NO: 40.

In yet another embodiment, the present invention provides an isolated polynucleotide encoding an antibody heavy chain or a functional fragment thereof, the antibody heavy chain or functional fragment thereof including a variable heavy (VH) chain domain, wherein the VH domain amino acid sequence is encoded by the nucleic acid sequence selected from the group consisting of SEQ ID NO: 1; SEQ ID NO: 5; SEQ ID NO: 9; SEQ ID NO: 13; SEQ ID NO: 17; SEQ ID NO: 21; SEQ ID NO: 25; SEQ ID NO: 29; SEQ ID NO: 33; SEQ ID NO: 35; and SEQ ID NO: 39.

In some embodiments, the present invention provides an isolated polynucleotide encoding an antibody light chain or a functional fragment thereof, the antibody light chain or functional fragment thereof including a variable light chain (VL) domain having VL CDR1, VL CDR2 and VL CDR3 amino acid sequences, wherein the VL CDR1 is selected from the group consisting of residues 27-37 of SEQ ID NO: 4; residues 27-37 of SEQ ID NO: 8; residues 27-38 of SEQ ID NO: 12; residues 27-38 of SEQ ID NO: 16; residues 27-38 of SEQ ID NO: 20; residues 27-38 of SEQ ID NO: 24; residues 27-37 of SEQ ID NO: 28; residues 27-37 of SEQ ID NO: 32; residues 27-32 of SEQ ID NO: 38; and residues 27-38 of SEQ ID NO: 42; the VL CDR2 is selected from the group consisting of residues 55-57 of SEQ ID NO: 4; residues 55-57 of SEQ ID NO: 8; residues 56-58 of SEQ ID NO: 12; residues 56-58 of SEQ ID NO: 16; residues 56-58 of SEQ ID NO: 20; residues 56-58 of SEQ ID NO: 24; residues 55-57 of SEQ ID NO: 28; residues 55-57 of SEQ ID NO: 32; residues 50-52 of SEQ ID NO: 38; and residues 56-58 of SEQ ID NO: 42, and the VL CDR3 is selected from the group consisting of residues 94-102 of SEQ ID NO: 4; residues 94-102 of SEQ ID NO: 8; residues 95-103 of SEQ ID NO: 12; residues 95-103 of SEQ ID NO: 16; residues 95-103 of SEQ ID NO: 20; residues 95-103 of SEQ ID NO: 24; residues 94-102 of SEQ ID NO: 28; residues 94-102 of SEQ ID NO: 32; residues 89-97 of SEQ ID NO: 38; and residues 95-103 of SEQ ID NO: 42.

In some embodiments, the present invention provides an isolated polynucleotide encoding an antibody light chain or a functional fragment thereof, the antibody light chain or functional fragment thereof including a variable light chain (VL) domain having VL CDR1, VL CDR2 and VL CDR3 amino acid sequences, wherein the VL CDR1 is encoded by the nucleic acid sequence selected from the group consisting of residues 79-111 of SEQ ID NO: 3; residues 79-111 of SEQ ID NO: 7; residues 79-114 of SEQ ID NO: 11; residues 79-114 of SEQ ID NO: 15; residues 79-114 of SEQ ID NO: 19; residues 79-114 of SEQ ID NO: 23; residues 79-111 of SEQ ID NO: 27; residues 79-111 of SEQ ID NO: 31; residues 79-96 of SEQ ID NO: 37; and residues 79-114 of SEQ ID NO: 41; the VL CDR2 is encoded by the nucleic acid sequence selected from the group consisting of residues 163-171 of SEQ ID NO: 3; 163-171 of SEQ ID NO: 7; 166-174 of SEQ ID NO: 11; 166-174 of SEQ ID NO: 15; 166-174 of SEQ ID NO: 19; 166-174 of SEQ ID NO: 23; 163-171 of SEQ ID NO: 27; 163-171 of SEQ ID NO: 31; 148-156 of SEQ ID NO: 37; and 166-174 of SEQ ID NO: 41; and the VL CDR3 is encoded by the nucleic acid sequence selected from the group consisting of residues 280-306 of SEQ ID NO: 3; residues 280-306 of SEQ ID NO: 7; residues 283-309 of SEQ ID NO: 11; residues 283-309 of SEQ ID NO: 15; residues 283-309 of SEQ ID NO: 19; residues 283-309 of SEQ ID NO: 23; residues 280-306 of SEQ ID NO: 27; residues 280-306 of SEQ ID NO: 31; residues 265-291 of SEQ ID NO: 37; residues 283-309 of SEQ ID NO: 41.

In some embodiments, the present invention provides an isolated polynucleotide encoding an antibody light chain or a functional fragment thereof, wherein the antibody light chain or functional fragment includes a variable light (VL) chain domain having the VL CDR1, VL CDR2 and VL CDR3 amino acid sequence of the clonal isolate 1B7, 2H12, 1G2, 1E9, 1H3, 2F5, 2F7, 2E12, 31F9, 31F9V2 or 32E2.

In some embodiments, the present invention provides an isolated polynucleotide encoding an antibody light chain or a functional fragment thereof, the antibody light chain or functional fragment thereof including a variable light chain (VL) domain, wherein the VL domain has VL CDR1, VL CDR2, and VL CDR3 amino acid sequences selected from the group consisting of residues 27-37, residues 55-57, and residues 94-102 of SEQ ID NO: 4; residues 27-37, residues 55-57, and residues 94-102 of SEQ ID NO: 8; residues 27-38, residues 56-58, and residues 95-103 of SEQ ID NO: 12; residues 27-38, residues 56-58, and residues 95-103 of SEQ ID NO: 16; residues 27-38, residues 56-58, and residues 95-103 of SEQ ID NO: 20; residues 27-38, residues 56-58, and residues 95-103 of SEQ ID NO: 24; residues 27-37, residues 55-57, and residues 94-102 of SEQ ID NO: 28; residues 27-37, residues 55-57, and residues 94-102 of SEQ ID NO: 32; residues 27-32, residues 50-52, and residues 89-97 of SEQ ID NO: 38; and residues 27-38, residues 56-58, and residues 95-103 of SEQ ID NO: 42.

In other embodiments, the present invention provides an isolated polynucleotide encoding an antibody light chain or a functional fragment thereof, the antibody light chain or functional fragment thereof including a variable light chain (VL) domain, wherein the VL domain has VL CDR1, VL CDR2, and VL CDR3 amino acid sequences are encoded by the nucleic acid sequence selected from the group consisting of residues 79-111, residues 163-171, and residues 280-306 of SEQ ID NO: 3; residues 79-111, residues 163-171, and residues 280-306 of SEQ ID NO: 7; residues 79-114, residues 166-174, and residues 283-309 of SEQ ID NO: 11; residues 79-114, residues 166-174, and residues 283-309 of SEQ ID NO: 15; residues 79-114, residues 166-174, and residues 283-309 of SEQ ID NO: 19; residues 79-114, residues 166-174, and residues 283-309 of SEQ ID NO: 23; residues 79-111, residues 163-171, and residues 280-306 of SEQ ID NO: 27; residues 79-111, residues 163-171, and residues 280-306 of SEQ ID NO: 31; residues 79-96, residues 148-156, and residues 265-291 of SEQ ID NO: 37; residues 79-114, residues 166-174, and residues 283-309 of SEQ ID NO: 41.

In another embodiment, the present invention provides an isolated polynucleotide encoding an antibody light chain or a functional fragment thereof, the antibody light chain or functional fragment thereof including a variable light chain (VL) domain, wherein the VL domain has an amino acid sequence selected from the group consisting of SEQ ID NO: 4; SEQ ID NO: 8; SEQ ID NO: 12; SEQ ID NO: 16; SEQ ID NO: 20; SEQ ID NO: 24; SEQ ID NO: 28; SEQ ID NO: 32; SEQ ID NO: 38; and SEQ ID NO: 42.

In yet another embodiment, the present invention provides an isolated polynucleotide encoding an antibody light chain or a functional fragment thereof, the antibody light chain or functional fragment thereof including a variable light chain (VL) domain, wherein the VL domain amino acid sequence is encoded by the nucleic acid sequence selected from the group consisting of SEQ ID NO: 3; SEQ ID NO: 7; SEQ ID NO: 11; SEQ ID NO: 15; SEQ ID NO: 19; SEQ ID NO: 23; SEQ ID NO: 27; SEQ ID NO: 31; SEQ ID NO: 37; and SEQ ID NO: 41.

In some embodiments, the present invention provides an isolated antibody or functional fragment thereof that binds to GD2. In some aspects, the antibody or functional fragment thereof has one or more of the CDRs depicted in FIGS. 1-21 or listed in Table 2. An antibody or functional fragment thereof that includes one or more of the CDRs, in particular CDR3, can specifically bind to GD2 as described herein. Specific binding to GD2 can include the specificity and affinity as described in Example I for any of the antibodies provided herein. In some aspects, an antibody or functional fragment thereof of the invention can include the CDC activity and/or ADCC activity of any one of the clonal isolates 1B7, 2H12, 1G2, 1E9, 1H3, 2F5, 2F7, 2E12, 31F9, 31F9V2 or 32E2 described herein.

In some embodiments, the present invention provides an isolated antibody or functional fragment thereof, wherein the antibody binds to GD2. Accordingly, in some aspects, the invention provides an isolated antibody or functional fragment thereof that binds to GD2, the antibody or functional fragment thereof including a variable heavy chain (VH) domain, the domain having VH CDR1, VH CDR2 and VH CDR3 amino acid sequences, wherein the VH CDR1 amino acid sequence is selected from the group consisting of residues 26-33 of SEQ ID NO: 2; residues 26-33 of SEQ ID NO: 6; residues 26-33 of SEQ ID NO: 10; residues 26-33 of SEQ ID NO: 14; residues 26-33 of SEQ ID NO: 18; residues 26-33 of SEQ ID NO: 22; residues 26-33 of SEQ ID NO: 26; residues 26-33 of SEQ ID NO: 30; residues 26-33 of SEQ ID NO: 34; residues 26-33 of SEQ ID NO: 36; and residues 26-33 of SEQ ID NO: 40; the VH CDR2 amino acid sequence is selected from the group consisting of residues 51-58 of SEQ ID NO: 2; residues 51-58 of SEQ ID NO: 6; residues 51-58 of SEQ ID NO: 10; residues 51-58 of SEQ ID NO: 14; residues 51-58 of SEQ ID NO: 18; residues 51-58 of SEQ ID NO: 22; residues 51-58 of SEQ ID NO: 26; residues 51-58 of SEQ ID NO: 30; residues 51-58 of SEQ ID NO: 34; residues 51-58 of SEQ ID NO: 36; and residues 51-58 of SEQ ID NO: 40; and the VH CDR3 amino acid sequence is selected from the group consisting of residues 97-109 of SEQ ID NO: 2; residues 97-109 of SEQ ID NO: 6; residues 97-108 of SEQ ID NO: 10; residues 97-108 of SEQ ID NO: 14; residues 97-108 of SEQ ID NO: 18; residues 97-108 of SEQ ID NO: 22; residues 97-109 of SEQ ID NO: 26; residues 97-109 of SEQ ID NO: 30; residues 97-110 of SEQ ID NO: 34; residues 97-110 of SEQ ID NO: 36; and residues 97-108 of SEQ ID NO: 40.

In some other aspects, the invention provides an isolated antibody or functional fragment thereof that binds to GD2, the antibody or functional fragment thereof including a variable heavy chain (VH) domain, wherein the VH domain has VH CDR1, VH CDR2, and VH CDR3 amino acid sequences selected from the group consisting of residues 26-33, residues 51-58, and residues 97-109 of SEQ ID NO: 2; residues 26-33, residues 51-58, and residues 97-109 of SEQ ID NO: 6; residues 26-33, residues 51-58, and residues 97-108 of SEQ ID NO: 10; residues 26-33, residues 51-58, and residues 97-108 of SEQ ID NO: 14; residues 26-33, residues 51-58, and residues 97-108 of SEQ ID NO: 18; residues 26-33, residues 51-58, and residues 97-108 of SEQ ID NO: 22; residues 26-33, residues 51-58, and residues 97-109 of SEQ ID NO: 26; residues 26-33, residues 51-58, and residues 97-109 of SEQ ID NO: 30; residues 26-33, residues 51-58, and residues 97-110 of SEQ ID NO: 34; residues 26-33, residues 51-58, and residues 97-110 of SEQ ID NO: 36; and residues 26-33, residues 51-58, and residues 97-108 of SEQ ID NO: 40.

In yet other aspects, the invention provides an isolated antibody or functional fragment thereof that binds to GD2, the antibody or functional fragment thereof including a variable heavy chain (VH) domain, wherein the VH domain has an amino acid sequence selected from the group consisting of SEQ ID NO: 2; SEQ ID NO: 6; SEQ ID NO: 10; SEQ ID NO: 14; SEQ ID NO: 18; SEQ ID NO: 22; SEQ ID NO: 26; SEQ ID NO: 30; SEQ ID NO: 34; SEQ ID NO: 36; and SEQ ID NO: 40.

In some embodiments, the present invention provides an isolated antibody or functional fragment thereof that binds to GD2, the antibody or functional fragment thereof including a variable light chain (VL) domain, wherein the VL domain has VL CDR1, VL CDR2 and VL CDR3 amino acid sequences, wherein the VL CDR1 is selected from the group consisting of residues 27-37 of SEQ ID NO: 4; residues 27-37 of SEQ ID NO: 8; residues 27-38 of SEQ ID NO: 12; residues 27-38 of SEQ ID NO: 16; residues 27-38 of SEQ ID NO: 20; residues 27-38 of SEQ ID NO: 24; residues 27-37 of SEQ ID NO: 28; residues 27-37 of SEQ ID NO: 32; residues 27-32 of SEQ ID NO: 38; and residues 27-38 of SEQ ID NO: 42; the VL CDR2 is selected from the group consisting of residues 55-57 of SEQ ID NO: 4; residues 55-57 of SEQ ID NO: 8; residues 56-58 of SEQ ID NO: 12; residues 56-58 of SEQ ID NO: 16; residues 56-58 of SEQ ID NO: 20; residues 56-58 of SEQ ID NO: 24; residues 55-57 of SEQ ID NO: 28; residues 55-57 of SEQ ID NO: 32; residues 50-52 of SEQ ID NO: 38; and residues 56-58 of SEQ ID NO: 42, and the VL CDR3 is selected from the group consisting of residues 94-102 of SEQ ID NO: 4; residues 94-102 of SEQ ID NO: 8; residues 95-103 of SEQ ID NO: 12; residues 95-103 of SEQ ID NO: 16; residues 95-103 of SEQ ID NO: 20; residues 95-103 of SEQ ID NO: 24; residues 94-102 of SEQ ID NO: 28; residues 94-102 of SEQ ID NO: 32; residues 89-97 of SEQ ID NO: 38; and residues 95-103 of SEQ ID NO: 42.

In some aspects, the present invention provides an isolated antibody or functional fragment thereof that binds to GD2, the antibody or functional fragment thereof including a variable light chain (VL) domain, wherein the VL domain has VL CDR1, VL CDR2, and VL CDR3 amino acid sequences selected from the group consisting of residues 27-37, residues 55-57, and residues 94-102 of SEQ ID NO: 4; residues 27-37, residues 55-57, and residues 94-102 of SEQ ID NO: 8; residues 27-38, residues 56-58, and residues 95-103 of SEQ ID NO: 12; residues 27-38, residues 56-58, and residues 95-103 of SEQ ID NO: 16; residues 27-38, residues 56-58, and residues 95-103 of SEQ ID NO: 20; residues 27-38, residues 56-58, and residues 95-103 of SEQ ID NO: 24; residues 27-37, residues 55-57, and residues 94-102 of SEQ ID NO: 28; residues 27-37, residues 55-57, and residues 94-102 of SEQ ID NO: 32; residues 27-32, residues 50-52, and residues 89-97 of SEQ ID NO: 38; and residues 27-38, residues 56-58, and residues 95-103 of SEQ ID NO: 42.

In some other aspects, the present invention provides an isolated antibody or functional fragment thereof that binds to GD2, the antibody or functional fragment thereof including a variable light chain (VL) domain, wherein the VL domain has an amino acid sequence selected from the group consisting of SEQ ID NO: 4; SEQ ID NO: 8; SEQ ID NO: 12; SEQ ID NO: 16; SEQ ID NO: 20; SEQ ID NO: 24; SEQ ID NO: 28; SEQ ID NO: 32; SEQ ID NO: 38; and SEQ ID NO: 42.

In some embodiments, the present invention provides an isolated antibody or functional fragment thereof that binds to GD2, the antibody or functional fragment thereof including a variable heavy chain (VH) domain and a variable light chain (VL) domain, wherein the VH domain has an amino acid sequence selected from the group consisting of SEQ ID NO: 2; SEQ ID NO: 6; SEQ ID NO: 10; SEQ ID NO: 14; SEQ ID NO: 18; SEQ ID NO: 22; SEQ ID NO: 26; SEQ ID NO: 30; SEQ ID NO: 34; SEQ ID NO: 36; and SEQ ID NO: 40; and the VL has an amino acid sequence selected from the group consisting of SEQ ID NO: 4; SEQ ID NO: 8; SEQ ID NO: 12; SEQ ID NO: 16; SEQ ID NO: 20; SEQ ID NO: 24; SEQ ID NO: 28; SEQ ID NO: 32; SEQ ID NO: 38; and SEQ ID NO: 42.

In some other embodiments, the present invention provides an isolated antibody or functional fragment thereof that binds to GD2, the antibody or functional fragment thereof including a variable heavy chain (VH) domain and a variable light chain (VL) domain, wherein the VH domain and the VL domain respectively include amino acid sequences from the group consisting of SEQ ID NO: 2 and SEQ ID NO: 4; SEQ ID NO: 6 and SEQ ID NO: 8; SEQ ID NO: 10 and SEQ ID NO: 12; SEQ ID NO: 14 and SEQ ID NO: 16; SEQ ID NO: 18 and SEQ ID NO: 20; SEQ ID NO: 22 and SEQ ID NO: 24; SEQ ID NO: 26 and SEQ ID NO: 28; SEQ ID NO: 30 and SEQ ID NO: 32; SEQ ID NO: 34 and SEQ ID NO: 38; SEQ ID NO: 36 and SEQ ID NO: 38; and SEQ ID NO: 40 and SEQ ID NO: 42.

TABLE 2

CDRs of Clonal Isolates

| Variable Domain | Nucleic Acid Residues (SEQ ID NO:) | | | Amino Acid Sequence (SEQ ID NO:) | | |
|---|---|---|---|---|---|---|
| | CDR1 | CDR2 | CDR3 | CDR1 | CDR2 | CDR3 |
| 1B7 VH | 76-99 (NO: 1) | 151-174 (NO: 1) | 289-327 (NO: 1) | 26-33 (NO: 2) | 51-58 (NO: 2) | 97-109 (NO: 2) |
| 1B7 VL | 79-111 (NO: 3) | 163-171 (NO: 3) | 280-306 (NO: 3) | 27-37 (NO: 4) | 55-57 (NO: 4) | 94-102 (NO: 4) |
| 2H12 VH | 76-99 (NO: 5) | 151-174 (NO: 5) | 289-327 (NO: 5) | 26-33 (NO: 6) | 51-58 (NO: 6) | 97-109 (NO: 6) |
| 2H12 VL | 79-111 (NO: 7) | 163-171 (NO: 7) | 280-306 (NO: 7) | 27-37 (NO: 8) | 55-57 (NO: 8) | 94-102 (NO: 8) |
| 1G2 VH | 76-99 (NO: 9) | 151-174 (NO: 9) | 289-324 (NO: 9) | 26-33 (NO: 10) | 51-58 (NO: 10) | 97-108 (NO: 10) |
| 1G2 VL | 79-114 (NO: 11) | 1-174 (NO: 11) | 23-309 (NO: 11) | 27 13 (NO: 12) | 565S (NO: 12) | 95-103 (NO: 12) |
| 1E9 VH | 76-99 (NO: 13) | 151-174 (NO: 13) | 289-324 (NO: 13) | 26-33 (NO: 14) | 51-58 (NO: 14) | 97-108 (NO: 14) |
| 1E9 VL | 79-114 (NO: 15) | 166-174 (NO: 15) | 283-309 (NO: 15) | 27-38 (NO: 16) | 56-58 (NO: 16) | 95-103 (NO: 16) |
| 1H3 VH | 76-99 (NO: 17) | 151-174 (NO: 17) | 289-324 (NO: 17) | 26-33 (NO: 18) | 51-58 (NO: 18) | 97-108 (NO: 18) |
| 1H3 VL | 79-114 (NO: 19) | 166-174 (NO: 19) | 283-309 (NO: 19) | 27-38 (NO: 20) | 56-58 (NO: 20) | 95-103 (NO: 20) |
| 2F5 VH | 76-99 (NO: 21) | 151-174 (NO: 21) | 289-324 (NO: 21) | 26-33 (NO: 22) | 51-58 (NO: 22) | 97-108 (NO: 22) |

TABLE 2-continued

CDRs of Clonal Isolates

| Variable Domain | Nucleic Acid Residues (SEQ ID NO:) | | | Amino Acid Sequence (SEQ ID NO:) | | |
|---|---|---|---|---|---|---|
| | CDR1 | CDR2 | CDR3 | CDR1 | CDR2 | CDR3 |
| 2F5 VL | 79-114 (NO: 23) | 166-174 (NO: 23) | 283-309 (NO: 23) | 27-38 (NO: 24) | 56-58 (NO: 24) | 95-103 (NO: 24) |
| 2F7 VH | 76-99 (NO: 25) | 151-174 (NO: 25) | 289-327 (NO: 25) | 26-33 (NO: 26) | 51-58 (NO: 26) | 97-109 (NO: 26) |
| 2F7 VL | 79-111 (NO: 27) | 163-171 (NO: 27) | 280-306 (NO: 27) | 27-37 (NO: 28) | 55-57 (NO: 28) | 94-102 (NO: 28) |
| 2E12 VH | 76-99 (NO: 29) | 151-174 (NO: 29) | 289-327 (NO: 29) | 26-33 (NO: 30) | 51-58 (NO: 30) | 97-109 (NO: 30) |
| 2E12 VL | 79-111 (NO: 31) | 163-171 (NO: 31) | 280-306 (NO: 31) | 27-37 (NO: 32) | 55-57 (NO: 32) | 94-102 (NO: 32) |
| 31F9 VH | 76-99 (NO: 33) | 151-174 (NO: 33) | 289-330 (NO: 33) | 26-33 (NO: 34) | 51-58 (NO: 34) | 97-110 (NO: 34) |
| 31FV2 VH | 76-99 (NO: 35) | 151-174 (NO: 35) | 289-330 (NO: 35) | 26-33 (NO: 36) | 51-58 (NO: 36) | 97-110 (NO: 36) |
| 31F9 VL | 79-96 (NO: 37) | 148-156 (NO: 37) | 265-291 (NO: 37) | 27-32 (NO: 38) | 50-52 (NO: 38) | 89-97 (NO: 38) |
| 32E2 VH | 76-99 (NO: 39) | 151-174 (NO: 39) | 289-324 (NO: 39) | 26-33 (NO: 40) | 51-58 (NO: 40) | 97-108 (NO: 40) |
| 32E2 VL | 79-114 (NO: 41) | 166-174 (NO: 41) | 283-309 (NO: 41) | 27-38 (NO: 42) | 56-58 (NO: 42) | 95-103 (NO: 42) |

In another embodiment, the invention provides a variant of the polynucleotides provided herein. A variant when used in reference to a polynucleotide includes a polynucleotide having one or more modified nucleotides, such as, but not limited to, a methylated nucleotide or a nucleotide analog. Additionally, a variant polynucleotide can include a polynucleotide that is interrupted by non-nucleotide components. Modifications to a polynucleotide can be imparted before or after assembly of the polynucleotide using methods well known to those skilled in the art. For example, a polynucleotide can be modified after polymerization by conjugation with a labeling component using either enzymatic or chemical techniques (e.g., as described in Gottfried and Weinhold, 2011, *Biochem. Soc. Trans.*, 39(2):523-628; Paredes et al., 2011, *Methods*, 54(2):251-259).

The polynucleotides can be obtained, and the nucleotide sequence of the polynucleotides determined, by any method well known in the art. Since the amino acid sequences of the variable heavy and light chain domains of 1B7, 2H12, 1G2, 1E9, 1H3, 2F5, 2F7, 2E12, 31F9, 31F9V2 and 32E2 are known (see, e.g., SEQ ID NOS: 2, 4, 6, 8, 10, 12, 14, 16, 18, 20, 22, 24, 26, 28, 30, 32, 34, 36, 38, 40, 42), nucleotide sequences encoding antibodies and modified versions of these antibodies can be determined using methods well known in the art, i.e., nucleotide codons known to encode particular amino acids are assembled in such a way to generate a nucleic acid that encodes the antibody. Such a polynucleotide encoding the antibody can be assembled from chemically synthesized oligonucleotides (e.g., as described in Kutmeier et al., 1994, *BioTechniques* 17:242), which, briefly, involves the synthesis of overlapping oligonucleotides containing portions of the sequence encoding the antibody, fragments, or variants thereof, annealing and ligating of those oligonucleotides, and then amplification of the ligated oligonucleotides by PCR.

A polynucleotide encoding an antibody or a functional fragment thereof of the invention can be generated using the nucleic acid sequence of the variable heavy and/or light chain domains of isolates 1B7, 2H12, 1G2, 1E9, 1H3, 2F5, 2F7, 2E12, 31F9, 31F9V2 or 32E2 (e.g., SEQ ID NOS: 1, 3, 5, 7, 9, 11, 13, 15, 17, 19, 21, 23, 25, 27, 29, 31, 33, 35, 37, 39, and 41). A nucleic acid encoding the antibody or functional fragment can be chemically synthesized or obtained from a suitable source (e.g., cDNA isolated from cells expressing the antibody or functional fragment thereof, such as hybridoma cells selected to express the antibody or functional fragment thereof) by PCR amplification using synthetic primers hybridizable to the 3' and 5' ends of the sequence or by cloning using an oligonucleotide probe specific for the particular nucleic acid sequence. Amplified nucleic acids generated by PCR can then be cloned into replicable cloning vectors using any method well known in the art.

In some aspects of the invention, the isolated antibody or functional fragment thereof is a monoclonal antibody. In some aspects of the invention, the isolated antibody or functional fragment thereof provided herein is an IgG or IgM isotype. In a further aspect of the invention, the antibody or function fragment thereof is an antibody of the IgG1 subclass.

In some embodiments, the present invention provides a method of producing an antibody or functional fragment thereof of the invention. The method of the invention can include introducing a polynucleotide of the invention into a host cell, culturing the host cell under conditions and for a sufficient period of time to produce the encoded heavy and/or light chain of an antibody or functional fragment of the invention, and purifying the heavy and/or light chain of an antibody or functional fragment. In other embodiments, the present invention provides a recombinant cell having a polynucleotide encoding an antibody or a functional fragment of the invention. In some aspects, the antibody or function fragment thereof has the variable heavy chain domain and the variable light chain domain of the designated antibodies 1B7, 2H12, 1G2, 1E9, 1H3, 2F5, 2F7, 2E12, 31F9, 31F9V2 or 32E2.

Recombinant expression of an antibody or functional fragment thereof of the invention that binds to a GD2 antigen can include construction of an expression vector containing a polynucleotide that encodes the heavy and/or light chain of an antibody or functional fragment of the invention. Once a polynucleotide encoding an antibody or functional fragment thereof (preferably, but not necessarily, containing the heavy and/or light chain variable domain) of the invention has been obtained, the vector for the production of the antibody or functional fragment can be produced by recombinant DNA technology using techniques well known in the art. Methods for preparing a protein by expressing a polynucleotide containing an antibody or a functional fragment thereof encoding nucleotide sequence are described herein.

Methods which are well known to those skilled in the art can be used to construct expression vectors containing antibody or functional fragments thereof coding sequences and appropriate transcriptional and translational control signals. These methods include, for example, in vitro recombinant DNA techniques, synthetic techniques, and in vivo genetic recombination. The invention, thus, provides replicable vectors including a nucleotide sequence encoding an antibody or functional fragment thereof of the invention operably linked to a promoter. Such vectors can include the nucleotide sequence encoding the constant region of the antibody molecule (see, e.g., International Publication Nos. WO 86/05807 and WO 89/01036; and U.S. Pat. No. 5,122,464) and the variable domain of the antibody can be cloned into such a vector for expression of the entire heavy, the entire light chain, or both the entire heavy and light chains.

The expression vector can be transferred to a host cell by conventional techniques and the transfected cells are then cultured by conventional techniques to produce an antibody or functional fragment thereof of the invention. Thus, the invention includes host cells containing a polynucleotide encoding an antibody or functional fragment thereof of the invention operably linked to a heterologous promoter. In some embodiments for the expression of double-chained antibodies, vectors encoding both the heavy and light chains can be co-expressed in the host cell for expression of the entire immunoglobulin molecule, as detailed below.

A variety of host-expression vector systems can be utilized to express the antibody or functional fragments thereof of the invention (see, e.g., U.S. Pat. No. 5,807,715). Such host-expression systems represent vehicles by which the coding sequences of interest can be produced and subsequently purified, but also represent cells which can, when transformed or transfected with the appropriate nucleotide coding sequences, express an antibody molecule of the invention in situ. These include but are not limited to microorganisms such as bacteria (e.g., *E. coli* and *B. subtilis*) transformed with recombinant bacteriophage DNA, plasmid DNA or cosmid DNA expression vectors containing antibody coding sequences; yeast (e.g., *Saccharomyces Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, NS0, and 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). In some aspects, bacterial cells such as *Escherichia coli*, or eukaryotic cells, especially for the expression of whole recombinant antibody, are used for the expression of a recombinant antibody or functional fragment. For example, mammalian cells such as Chinese hamster ovary cells (CHO), in conjunction with a vector such as the major intermediate early gene promoter element from human cytomegalovirus is an effective expression system for antibodies (Foecking et al., 1986, *Gene* 45:101; and Cockett et al., 1990, *Bio/Technology* 8:2). In some embodiments, antibodies or fragments thereof of the invention are produced in CHO cells. In one embodiment, the expression of nucleotide sequences encoding antibodies or functional fragments thereof of the invention which bind to GD2 is regulated by a constitutive promoter, inducible promoter or tissue specific promoter.

In bacterial systems, a number of expression vectors can be advantageously selected depending upon the use intended for the antibody molecule being expressed. For example, when a large quantity of such an antibody is to be produced, for the generation of pharmaceutical compositions of an antibody molecule, vectors which direct the expression of high levels of fusion protein products that are readily purified can be desirable. Such vectors include, but are not limited to, the *E. coli* expression vector pUR278 (Ruther et al., 1983, *EMBO* 12:1791), in which the antibody coding sequence can be ligated individually into the vector in frame with the lac Z coding region so that a fusion protein is produced; pIN vectors (Inouye & Inouye, 1985, *Nucleic Acids Res.* 13:3101-3109; Van Heeke & Schuster, 1989, *J. Biol. Chem.* 24:5503-5509); and the like. pGEX vectors can also be used to express foreign polypeptides as fusion proteins with glutathione 5-transferase (GST). In general, such fusion proteins are soluble and can easily be purified from lysed cells by adsorption and binding to matrix glutathione agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The antibody or functional fragment coding sequence can be cloned individually into non-essential regions (for example the polyhedrin gene) of the virus and placed under control of an AcNPV promoter (for example the polyhedrin promoter).

In mammalian host cells, a number of viral-based expression systems can be utilized. In cases where an adenovirus is used as an expression vector, the antibody coding sequence of interest can be ligated to an adenovirus transcription/translation control complex, e.g., the late promoter and tripartite leader sequence. This chimeric gene can then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts (e.g., see Logan & Shenk, 1984, *Proc. Natl. Acad. Sci. USA* 8 1:355-359). Specific initiation signals can also be used for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression can be enhanced by the inclusion of appropriate transcription enhancer elements, transcription terminators, etc. (see, e.g., Bittner et al., 1987, *Methods in Enzymol.* 153:51-544).

In addition, a host cell strain can be chosen which modulates the expression of the inserted sequences, or modifies and processes the gene product in the specific fashion desired. Such modifications (e.g., glycosylation) and processing (e.g., cleavage) of protein products can be important for the function of the antibody or functional fragment. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product can be used. Such mammalian host cells include but are not limited to CHO, VERY, BHK, Hela, COS, MDCK, 293, 3T3, W138, BT483, Hs578T, HTB2, BT2O and T47D, NS0 (a murine myeloma cell line that does not endogenously produce any immunoglobulin chains), CRL7O3O and HsS78Bst cells.

For long-term, high-yield production of recombinant proteins, stable expression is preferred. For example, cell lines which stably express the antibody or functional fragment of the invention can be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells can be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method can advantageously be used to engineer cell lines which express the antibody molecule.

A number of selection systems can be used, including but not limited to, the herpes simplex virus thymidine kinase (Wigler et al., 1977, *Cell* 11:223), hypoxanthineguanine phosphoribosyltransferase (Szybalska & Szybalski, 1992, *Proc. Natl. Acad. Sci. USA* 48:202), and adenine phosphoribosyltransferase (Lowy et al., 1980, *Cell* 22:8-17) genes can be employed in tk-, hgprt- or aprt-cells, respectively. Also, antimetabolite resistance can be used as the basis of selection for the following genes: dhfr, which confers resistance to methotrexate (Wigler et al., 1980, *Proc. Natl. Acad. Sci. USA.* 77(6):3567-70; O'Hare et al., 1981, *Proc. Natl. Acad. Sci. USA* 78:1527); glutamine synthetase (GS), which is an enzyme responsible for the biosynthesis of glutamine using glutamate and ammonia (Bebbington et al., 1992, *Biuotechnology* 10:169); gpt, which confers resistance to mycophenolic acid (Mulligan & Berg, 1981, *Proc. Natl. Acad. Sci. USA* 78:2072); neo, which confers resistance to the aminoglycoside G-418 (Wu and Wu, 1991, *Biotherapy* 3:87-95; Tolstoshev, 1993, *Ann. Rev. Pharmacol. Toxicol.* 32:573-596; Mulligan, 1993, *Science* 260:926-932; and Morgan and Anderson, 1993, *Ann. Rev. Biochem.* 62:191-217; May, 1993, TIB TECH 11(5):155-215); and hygro, which confers resistance to hygromycin (Santerre et al., 1984, *Gene* 30:147). Methods well known in the art of recombinant DNA technology can be routinely applied to select the desired recombinant clone, and such methods are described, for example, in Ausubel et al. (eds.), *Current Protocols in Molecular Biology*, John Wiley & Sons, N Y (1993); Kriegler, *Gene Transfer and Expression*, A Laboratory Manual, Stockton Press, N Y (1990); and in Chapters 12 and 13, Dracopoli et al. (eds.), *Current Protocols in Human Genetics*, John Wiley & Sons, N Y (1994); Colberre-Garapin et al., 1981, *J. Mol. Biol.* 150:1, which are incorporated by reference herein in their entireties.

The expression levels of an antibody molecule can be increased by vector amplification (for a review, see Bebbington and Hentschel, The use of vectors based on gene amplification for the expression of cloned genes in mammalian cells in DNA cloning, Vol. 3 (Academic Press, New York, 1987)). When a marker in the vector system expressing an antibody or functional fragment thereof is amplifiable, increase in the level of inhibitor present in culture of host cell will increase the number of copies of the marker gene. Since the amplified region is associated with the antibody gene, production of the antibody will also increase (Crouse et al., 1983, *Mol. Cell. Biol.* 3:257).

The host cell can be co-transfected with two expression vectors of the invention, the first vector encoding a heavy chain derived polypeptide and the second vector encoding a light chain derived polypeptide. The two vectors can contain identical selectable markers which enable equal expression of heavy and light chain polypeptides. Alternatively, a single vector can be used which encodes, and is capable of expressing, both heavy and light chain polypeptides. In such situations, the light chain can be placed before the heavy chain to avoid an excess of toxic free heavy chain (Proudfoot, 1986, Nature 322:52; and Kohler, 1980, *Proc. Natl. Acad. Sci. USA* 77:2197-2199). The coding sequences for the heavy and light chains can include cDNA or genomic DNA.

Additionally, polynucleotides encoding the heavy and/or light chains of the antibody or functional fragment of the invention can be subjected to codon optimization using techniques well known in the art to achieve optimized expression of an antibody or functional fragment of the invention in a desired host cell. For example, in one method of codon optimization, a native codon is substituted by the most frequent codon from a reference set of genes, wherein the rate of codon translation for each amino acid is designed to be high. Additional exemplary methods for generating codon optimized polynucleotides for expression of a desired protein, which can be applied to the heavy and/or light chains of the antibody or functional fragment of the invention, are described in Kanaya et al., *Gene,* 238:143-155 (1999), Wang et al., *Mol. Biol. Evol.,* 18(5):792-800 (2001), U.S. Pat. No. 5,795,737, U.S. Publication 2008/0076161 and WO 2008/000632.

Once an antibody molecule of the invention has been produced by recombinant expression, it can be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. Further, the antibodies or functional fragments of the present invention can be fused to heterologous polypeptide sequences provided herein or otherwise known in the art to facilitate purification. For example, an antibody or functional fragment of the invention can be purified through recombinantly adding a poly-histidine tag (His-tag), FLAG-tag, hemagglutinin tag (HA-tag) or myc-tag among others that are commercially available and utilizing purification methods well known to those skilled in the art.

In some embodiments, the antibody functional fragment of the invention can be, but is not limited to, a Fab, a Fab', a F(ab')2, a Fabc, a scFV, a diabody, a triabody, minibody or a single-domain antibody (sdAB). With respect to antibodies and functional fragments thereof, various forms, alterations and modifications are well known in the art. The GD2 specific antibody fragments of the invention can include any of such various antibody forms, alterations and modifications. Examples of such various forms and terms as they are known in the art are set forth below.

A Fab fragment refers to a monovalent fragment consisting of the VL, VH, CL and CH1 domains; a F(ab')$_2$ fragment is a bivalent fragment including two Fab fragments linked by a disulfide bridge at the hinge region; a Fd fragment consists of the VH and CH1 domains; an Fv fragment consists of the VL and VH domains of a single arm of an antibody; and a dAb fragment (Ward et al., Nature 341:544-546, (1989)) consists of a VH domain.

An antibody can have one or more binding sites. If there is more than one binding site, the binding sites can be identical to one another or can be different. For example, a naturally occurring immunoglobulin has two identical binding sites, a single-chain antibody or Fab fragment has one binding site, while a "bispecific" or "bifunctional" antibody has two different binding sites.

A single-chain antibody (scFv) refers to an antibody in which a VL and a VH region are joined via a linker (e.g., a synthetic sequence of amino acid residues) to form a continuous polypeptide chain wherein the linker is long enough to allow the protein chain to fold back on itself and form a monovalent antigen binding site (see, e.g., Bird et al., Science 242:423-26 (1988) and Huston et al., Proc. Natl. Acad. Sci. USA 85:5879-83 (1988)). Diabodies refer to bivalent antibodies including two polypeptide chains, wherein each polypeptide chain includes VH and VL domains joined by a linker that is too short to allow for pairing between two domains on the same chain, thus allowing each domain to pair with a complementary domain on another polypeptide chain (see, e.g., Holliger et al., *Proc. Natl. Acad. Sci. USA* 90:6444-48 (1993), and Poljak et al., *Structure* 2:1121-23 (1994)). If the two polypeptide chains of a diabody are identical, then a diabody resulting from their pairing will have two identical antigen binding sites. Polypeptide chains having different sequences can be used to make a diabody with two different antigen binding sites. Similarly, tribodies and tetrabodies are antibodies including three and four polypeptide chains, respectively, and forming three and four antigen binding sites, respectively, which can be the same or different.

The present invention also provides an antibody or functional fragment thereof derivative of 1B7, 2H12, 1G2, 1E9, 1H3, 2F5, 2F7, 2E12, 31F9, 31F9V2 and 32E2, wherein the antibody or functional fragment binds to GD2. Standard techniques well known to those of skill in the art can be used to introduce mutations in the nucleotide sequence encoding an antibody or functional fragment thereof of the invention, including, for example, site-directed mutagenesis and PCR-mediated mutagenesis which results in amino acid substitutions. In some aspects, the derivative includes less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the original molecule.

In some embodiments, the invention provides an antibody or functional fragment thereof having modified forms of naturally occurring amino acids, conservative substitutions, non-naturally occurring amino acids, amino acid analogues and mimetics so long as such the antibody or functional fragment retains functional activity as defined herein. In one embodiment, the derivative has conservative amino acid substitutions that are made at one or more predicted non-essential amino acid residues. A conservative amino acid substitution is one in which the amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity. Following mutagenesis, the encoded antibody or functional fragment thereof can be expressed and the activity of the antibody or functional fragment can be determined.

In some embodiments, the invention provides an antibody or functional fragment thereof having modified fucosylation, galactosylation and/or sialylation of an Fc fragment contained within an antibody or functional fragment of the invention. Such modifications of an Fc fragment can effect Fc receptor-mediated activity as discussed in Peipp et al., *Blood,* 112(6):2390-2399 (2008). For example, glycoengineered therapeutic antibodies lacking core fucose residues from the Fc N-glycans exhibit strong ADCC at lower concentrations with much higher efficacy compared to fucosylated counterparts. Shields et al., *J. Biol. Chem.,* 277(30): 26733-40 (2002); Okazaki et al., *J Mol Biol.,* 336:1239-1249 (2004); Natsume et al., *J. Immunol. Methods.,* 306:93-103 (2005). Methods for modifying the fucosylation, galactosylation and/or sialylation of an antibody for functional fragment thereof are well known in the art. For example, defucosylation approaches can be grouped into three methodologies (1) conversion of the N-glycosylation pathway of nonmammalian cells to the 'humanized' non-fucosylation pathway; (2) inactivation of the N-glycan fucosylation pathway of mammalian cells and (3) in vitro chemical synthesis of non-fucosylated N-glycoprotein or enzymatic modification of N-glycans to non-fucosylated forms, as described in Yamane-Ohnuki et al., MAbs., 1(3):230-236 (2009). It is understood that any one of these methods or any other method that is well known in the art can be used to produce an antibody or functional fragment thereof having modified fucosylation, galactosylation and/or sialylation.

Antibodies or functional fragments thereof of the invention that bind to GD2 can be produced by any method known in the art for the synthesis of antibodies, in particular, by chemical synthesis or by recombinant expression techniques. The practice of the invention employs, unless otherwise indicated, conventional techniques in molecular biology, microbiology, genetic analysis, recombinant DNA, organic chemistry, biochemistry, PCR, oligonucleotide synthesis and modification, nucleic acid hybridization, and related fields within the skill of the art. These techniques are described in the references cited herein and are fully explained in the literature. See, e.g., Maniatis et al. (1982) *Molecular Cloning: A Laboratory Manual*, Cold Spring Harbor Laboratory Press; Sambrook et al. (1989), *Molecular*

Cloning: A Laboratory Manual, Second Edition, Cold Spring Harbor Laboratory Press; Sambrook et al. (2001) Molecular Cloning: A Laboratory Manual, Cold Spring Harbor Laboratory Press, Cold Spring Harbor, N.Y.; Ausubel et al., Current Protocols in Molecular Biology, John Wiley & Sons (1987 and annual updates); Current Protocols in Immunology, John Wiley & Sons (1987 and annual updates) Gait (ed.) (1984) Oligonucleotide Synthesis: A Practical Approach, IRL Press; Eckstein (ed.) (1991) Oligonucleotides and Analogues: A Practical Approach, IRL Press; Birren et al. (eds.) (1999) Genome Analysis: A Laboratory Manual, Cold Spring Harbor Laboratory Press; Borrebaeck (ed.) (1995) Antibody Engineering, Second Edition, Oxford University Press; Lo (ed.) (2006) Antibody Engineering: Methods and Protocols (Methods in Molecular Biology); Vol. 248, Humana Press, Inc; each of which is incorporated herein by reference in its entirety.

Monoclonal antibodies can be prepared using a wide variety of techniques known in the art including the use of hybridoma and recombinant technologies, or a combination thereof. For example, monoclonal antibodies can be produced using hybridoma techniques including those known in the art and taught, for example, in Harlow et al., Antibodies: A Laboratory Manual, (Cold Spring Harbor Laboratory Press, 2nd ed. 1988); Hammerling et al., in: Monoclonal Antibodies and T-Cell Hybridomas 563 681 (Elsevier, N.Y., 1981), each of which is incorporated herein by reference in its entirety. A monoclonal antibody is not limited to antibodies produced through hybridoma technology. Other exemplary methods of producing monoclonal antibodies are known in the art. Additional exemplary methods of producing monoclonal antibodies are provided in Example I herein.

Antibody functional fragments which bind GD2 can be generated by any technique well known to those of skill in the art. For example, Fab and F(ab')$_2$ fragments of the invention can be produced by proteolytic cleavage of immunoglobulin molecules, using enzymes such as papain (to produce Fab fragments) or pepsin (to produce F(ab')$_2$ fragments). F(ab')$_2$ fragments contain the variable region, the light chain constant region and the CH1 domain of the heavy chain.

The antibody functional fragments of the invention can also be generated using various phage display methods known in the art. For example, in phage display methods, functional antibody domains, such as the heavy and/or light chain variable regions having one, two, three, four, five or six CDRs provided herein, are displayed on the surface of phage particles which carry the polynucleotide sequences encoding them. The DNA encoding the VH and VL domains are recombined together with an scFv linker by PCR and cloned into a phagemid vector. The vector is electroporated in E. coli and the E. coli is infected with helper phage. Phage used in these methods are typically filamentous phage including fd and M13 and the VH and VL domains are usually recombinantly fused to either the phage gene III or gene VIII. Phage expressing an antigen binding domain that binds to a particular antigen, such as GD2, can be selected or identified with antigen, e.g., using labeled antigen or antigen bound or captured to a solid surface or bead. Examples of phage display methods that can be used to make the antibody functional fragments of the present invention include those disclosed in Brinkman et al., 1995, J. Immunol. Methods 182:41-50; Ames et al., 1995, J. Immunol. Methods 184:177-186; Kettleborough et al., 1994, Eur. J. Immunol. 24:952-958; Persic et al., 1997, Gene 187:9-18; Burton et al., 1994, Advances in Immunology 57:191-280; PCT Application No. PCT/GB91/01134; International Publication Nos. WO 90/02809, WO 91/10737, WO 92/01047, WO 92/18619, WO 93/11236, WO 95/15982, WO 95/20401, and WO97/13844; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727, 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described herein.

Techniques to recombinantly produce Fab, Fab' and F(ab')2 fragments can also be employed using methods known in the art such as those disclosed in PCT publication No. WO 92/22324; Mullinax et al., 1992, BioTechniques 12(6):864-869; Sawai et al., 1995, AJRI 34:26-34; and Better et al., 1988, Science 240:1041-1043, each of which is incorporated by reference in its entirety.

To generate whole antibodies, PCR primers including VH or VL nucleotide sequences, a restriction site, and a flanking sequence to protect the restriction site can be used to amplify the VH or VL sequences in scFv clones. Utilizing cloning techniques well known to those of skill in the art, the PCR amplified VH domains can be cloned into vectors expressing a VH constant region, e.g., the human gamma 1 constant region, and the PCR amplified VL domains can be cloned into vectors expressing a VL constant region, e.g., human kappa or lambda constant regions. The VH and VL domains can also be cloned into one vector expressing the necessary constant regions. The heavy chain conversion vectors and light chain conversion vectors are then co-transfected into cell lines to generate stable or transient cell lines that express full-length antibodies, e.g., IgG, using techniques well known to those of skill in the art.

In some embodiments, an antibody or functional fragment of the invention is conjugated (covalent or non-covalent conjugations) or recombinantly fused to one or more diagnostic agent, detectable agent or therapeutic agent or any other desired molecule. The conjugated or recombinantly fused antibody or functional fragment can be useful for monitoring or diagnosing the onset, development, progression and/or severity of a disease associated with the expression of GD2, such as cancer or tumor formation, as part of a clinical testing procedure, such as determining the efficacy of a particular therapy.

In some aspects, an antibody or functional fragment thereof of the invention is conjucated with a detectable agent. Detection and diagnosis can be accomplished, for example, by coupling the antibody or functional fragment of the invention to detectable substances including, but not limited to, radioactive materials, such as, but not limited to, zirconium ($^{89}$Zr), iodine ($^{131}$I, $^{125}$I, $^{124}$I, $^{123}$I, and $^{121}$I) carbon ($^{14}$C, $^{11}$C), sulfur ($^{35}$S), tritium ($^{3}$H), indium ($^{115}$In, $^{113}$In, $^{112}$In, and $^{111}$In,), technetium ($^{99}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{15}$O, $^{13}$N, $^{64}$Cu, $^{94m}$Tc, $^{153}$Sm, $^{177}$Lu, $^{159}$Gd, $^{149}$Pm, $^{140}$La, $^{175}$Yb, $^{166}$Ho, $^{86}$Y, $^{90}$Y, $^{47}$Sc, $^{186}$Re, $^{188}$Re, $^{142}$Pr, $^{105}$Rh, $^{97}$Ru, $^{68}$Ge, $^{57}$Co, $^{65}$Zn, $^{85}$Sr, $^{32}$P, $^{153}$Gd, $^{169}$Yb, $^{51}$Cr, $^{54}$Mn, $^{75}$Se, $^{113}$Sn, and $^{117}$Sn; and positron emitting metals using various positron emission tomographies, various enzymes, such as, but not limited to, horseradish peroxidase, alkaline phosphatase, beta-galactosidase, or acetylcholinesterase; prosthetic groups, such as, but not limited to, streptavidin/biotin and avidin/biotin;

fluorescent materials, such as, but not limited to, umbelliferone, fluorescein, fluorescein isothiocynate, rhodamine, dichlorotriazinylamine fluorescein, dansyl chloride or phycoerythrin; luminescent materials, such as, but not limited to, luminol; bioluminescent materials, such as but not limited to, luciferase, luciferin, and aequorin, and non-radioactive paramagnetic metal ions.

The present invention further encompasses therapeutic uses of an antibody or functional fragment of the invention conjugated (covalent or non-covalent conjugations) or recombinantly fused to one or more therapeutic agent. In this context, for example, the antibody can be conjugated or recombinantly fused to a therapeutic agent, such as a cytotoxin, e.g., a cytostatic or cytocidal agent, or a radioactive metal ion, e.g., alpha-emitters. A cytotoxin or cytotoxic agent includes any agent that is detrimental to cells. A therapeutic agent can be a chemotherapeutic such as, but is not limited to, an anthracycline (e.g., doxorubicin and daunorubicin (formerly daunomycin)); a taxan (e.g., paclitaxel (Taxol) and docetaxel (Taxotere); an antimetabolite (e.g., methotrexate, 6-mercaptopurine, 6-thioguanine, cytarabine, 5-fluorouracil and decarbazine); or an alkylating agent (e.g., mechlorethamine, thioepa chlorambucil, melphalan, carmustine (BCNU), lomustine (CCNU), cyclothosphamide, busulfan, dibromomannitol, streptozotocin, mitomycin C, cisdichlorodiamine platinum (II) (DDP) and cisplatin); an antibiotic (e.g., actinomycin D, bleomycin, mithramycin, and anthramycin (AMC)); an Auristatin molecule (e.g., auristatin PHE, bryostatin 1, solastatin 10, monomethyl auristatin E (MMAE) and monomethylauristatin F (MMAF)); a hormone (e.g., glucocorticoids, progestins, androgens, and estrogens); a nucleoside analoge (e.g. Gemcitabine), a DNA-repair enzyme inhibitor (e.g., etoposide and topotecan), a kinase inhibitor (e.g., compound ST1571, also known as Gleevec or imatinib mesylate); a cytotoxic agent (e.g., maytansine, paclitaxel, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, 1-dehydrotestosterone, glucorticoids, procaine, tetracaine, lidocaine, propranolol, puromycin and analogs or homologs thereof, and those compounds disclosed in U.S. Pat. Nos. 6,245,759, 6,399,633, 6,383,790, 6,335,156, 6,271,242, 6,242,196, 6,218,410, 6,218,372, 6,057,300, 6,034,053, 5,985,877, 5,958,769, 5,925,376, 5,922,844, 5,911,995, 5,872,223, 5,863,904, 5,840,745, 5,728,868, 5,648,239, 5,587,459); a farnesyl transferase inhibitor (e.g., R115777, BMS-214662, and those disclosed by, for example, U.S. Pat. Nos. 6,458,935, 6,451,812, 6,440,974, 6,436,960, 6,432,959, 6,420,387, 6,414,145, 6,410,541, 6,410,539, 6,403,581, 6,399,615, 6,387,905, 6,372,747, 6,369,034, 6,362,188, 6,342,765, 6,342,487, 6,300,501, 6,268,363, 6,265,422, 6,248,756, 6,239,140, 6,232,338, 6,228,865, 6,228,856, 6,225,322, 6,218,406, 6,211,193, 6,187,786, 6,169,096, 6,159,984, 6,143,766, 6,133,303, 6,127,366, 6,124,465, 6,124,295, 6,103,723, 6,093,737, 6,090,948, 6,080,870, 6,077,853, 6,071,935, 6,066,738, 6,063,930, 6,054,466, 6,051,582, 6,051,574, and 6,040,305); a topoisomerase inhibitor (e.g., camptothecin, irinotecan, SN-38, topotecan, 9-aminocamptothecin, GG-211 (GI 147211), DX-8951f, IST-622, rubitecan, pyrazoloacridine, XR-5000, saintopin, UCE6, UCE1022, TAN-1518A, TAN 1518B, KT6006, KT6528, ED-110, NB-506, ED-110, NB-506, fagaronine, coralyne, beta-lapachone and rebeccamycin); a DNA minor groove binder (e.g., Hoescht dye 33342 and Hoechst dye 33258); adenosine deaminase inhibitors (e.g., Fludarabine phosphate and 2-Chlorodeoxyadenosine); or pharmaceutically acceptable salts, solvates, clathrates, or prodrugs thereof. A therapeutic agent can be a immunotherapeutic such as, but is not limited to, cetuximab, bevacizumab, heceptin, rituximab).

In addition, an antibody or functional fragment of the invention can be conjugated to a therapeutic agent such as a radioactive metal ion, such as alpha-emitters such as $^{213}$Bi or macrocyclic chelators useful for conjugating radiometal ions, including but not limited to, $^{131}$In, $^{131}$LU, $^{131}$Y, $^{131}$Ho, $^{131}$Sm; or a macrocyclic chelator, such as 1,4,7,10-tetraazacyclododecane-N,N',N'',N'''-tetraacetic acid (DOTA) which can be attached to the antibody or functional fragment via a linker molecule. Such linker molecules are commonly known in the art and described in Denardo et al., 1998, Clin Cancer Res. 4(10):2483-90; Peterson et al., 1999, Bioconjug. Chem. 10(4):553-7; and Zimmerman et al., 1999, Nucl. Med. Biol. 26(8):943-50.

Further, an antibody or functional fragment of the invention can be conjugated (covalent or non-covalent conjugations) or recombinantly fused to a therapeutic agent that modifies a given biological response. Thus, therapeutic agents are not to be construed as limited to classical chemical therapeutic agents. For example, the therapeutic agent can be a protein, peptide, or polypeptide possessing a desired biological activity. Such proteins can include, for example, a toxin (e.g., abrin, ricin A, pseudomonas exotoxin, cholera toxin and diphtheria toxin); a protein such as tumor necrosis factor, γ-interferon, α-interferon, nerve growth factor, platelet derived growth factor, tissue plasminogen activator, an apoptotic agent (e.g., TNF-γ, AIM I, AIM II, Fas Ligand and VEGF), an anti-angiogenic agent (e.g., angiostatin, endostatin and a component of the coagulation pathway such as tissue factor); a biological response modifier (e.g., a cytokine such as interferon gamma, interleukin-1, interleukin-2, interleukin-5, interleukin-6, interleukin-7, interleukin-9, interleukin-10, interleukin-12, interleukin-15, interleukin-23, granulocyte macrophage colony stimulating factor, and granulocyte colony stimulating factor); a growth factor (e.g., growth hormone), or a coagulation agent (e.g., calcium, vitamin K, tissue factors, such as but not limited to, Hageman factor (factor XII), high-molecular-weight kininogen (HMWK), prekallikrein (PK), coagulation proteins-factors II (prothrombin), factor V, XIIa, VIII, XIIIa, XI, XIa, IX, IXa, X, phospholipid, and fibrin monomer).

The present invention encompasses antibodies or functional fragments of the invention recombinantly fused or chemically conjugated (covalent or non-covalent conjugations) to a heterologous protein or polypeptide to generate fusion proteins. In some aspects, such a polypeptide can be about 10, about 20, about 30, about 40, about 50, about 60, about 70, about 80, about 90 or about 100 amino acids in length. In some aspects, the invention provides fusion proteins having a functional fragment of an antibody of the invention (e.g., a Fab fragment, Fd fragment, Fv fragment, F(ab)$_2$ fragment, a VH domain, a VH CDR, a VL domain or a VL CDR) and a heterologous protein or polypeptide. In one embodiment, the heterologous protein or polypeptide that the antibody or functional fragment is fused to is useful for targeting the antibody or functional fragment to a particular cell type, such as a cell that expresses GD2.

A conjugated or fusion protein of the invention includes any antibody or functional fragment of the invention provided herein conjugated (covalent or non-covalent conjugations) or recombinantly fused to a diagnostic agent, detectable agent or therapeutic agent. In one embodiment, a conjugated or fusion protein of the invention includes a 1B7, 2H12, 1G2, 1E9, 1H3, 2F5, 2F7, 2E12, 31F9, 31F9V2 or 32E2 antibody, and a diagnostic agent, detectable agent or therapeutic agent. In another embodiment, a conjugated or fusion protein of the invention includes a functional fragment of 1B7, 2H12, 1G2, 1E9, 1H3, 2F5, 2F7, 2E12, 31F9, 31F9V2 or 32E2 antibodies, and a diagnostic agent, detectable agent or therapeutic agent.

In some embodiments, a conjugated or fusion protein of the present invention includes one or more VH CDRs having the amino acid sequence of any one of the VH CDRs depicted in SEQ ID NOS: 2, 6, 10, 14, 18, 22, 26, 30, 34, 36, or 40 and a diagnostic agent, detectable agent or therapeutic agent. In another embodiment, a conjugated or fusion protein includes one or more VL CDRs having the amino acid sequence of any one of the VL CDRs depicted in SEQ ID NOS: 4, 8, 12, 16, 20, 24, 28, 32, 38, or 42 and a diagnostic agent, detectable agent or therapeutic agent.

In some aspects, a conjugated or fusion protein of the invention includes a VH domain, the VH domain having VH CDR1, VH CDR2 and VH CDR3 amino acid sequences, wherein the VH CDR1 amino acid sequence is selected from the group consisting of residues 26-33 of SEQ ID NO: 2; residues 26-33 of SEQ ID NO: 6; residues 26-33 of SEQ ID NO: 10; residues 26-33 of SEQ ID NO: 14; residues 26-33 of SEQ ID NO: 18; residues 26-33 of SEQ ID NO: 22; residues 26-33 of SEQ ID NO: 26; residues 26-33 of SEQ ID NO: 30; residues 26-33 of SEQ ID NO: 34; residues 26-33 of SEQ ID NO: 36; and residues 26-33 of SEQ ID NO: 40; the VH CDR2 amino acid sequence is selected from the group consisting of residues 51-58 of SEQ ID NO: 2; residues 51-58 of SEQ ID NO: 6; residues 51-58 of SEQ ID NO: 10; residues 51-58 of SEQ ID NO: 14; residues 51-58 of SEQ ID NO: 18; residues 51-58 of SEQ ID NO: 22; residues 51-58 of SEQ ID NO: 26; residues 51-58 of SEQ ID NO: 30; residues 51-58 of SEQ ID NO: 34; residues 51-58 of SEQ ID NO: 36; and residues 51-58 of SEQ ID NO: 40; and the VH CDR3 amino acid sequence is selected from the group consisting of residues 97-109 of SEQ ID NO: 2; residues 97-109 of SEQ ID NO: 6; residues 97-108 of SEQ ID NO: 10; residues 97-108 of SEQ ID NO: 14; residues 97-108 of SEQ ID NO: 18; residues 97-108 of SEQ ID NO: 22; residues 97-109 of SEQ ID NO: 26; residues 97-109 of SEQ ID NO: 30; residues 97-110 of SEQ ID NO: 34; residues 97-110 of SEQ ID NO: 36; and residues 97-108 of SEQ ID NO: 40, and a diagnostic agent, detectable agent or therapeutic agent.

In some other aspects, a conjugated or fusion protein of the invention includes a VH domain, the VH domain having VH CDR1, VH CDR2, and VH CDR3 amino acid sequences selected from the group consisting of residues 26-33, residues 51-58, and residues 97-109 of SEQ ID NO: 2; residues 26-33, residues 51-58, and residues 97-109 of SEQ ID NO: 6; residues 26-33, residues 51-58, and residues 97-108 of SEQ ID NO: 10; residues 26-33, residues 51-58, and residues 97-108 of SEQ ID NO: 14; residues 26-33, residues 51-58, and residues 97-108 of SEQ ID NO: 18; residues 26-33, residues 51-58, and residues 97-108 of SEQ ID NO: 22; residues 26-33, residues 51-58, and residues 97-109 of SEQ ID NO: 26; residues 26-33, residues 51-58, and residues 97-109 of SEQ ID NO: 30; residues 26-33, residues 51-58, and residues 97-110 of SEQ ID NO: 34; residues 26-33, residues 51-58, and residues 97-110 of SEQ ID NO: 36; and residues 26-33, residues 51-58, and residues 97-108 of SEQ ID NO: 40, and a diagnostic agent, detectable agent or therapeutic agent.

In yet other aspects, a conjugated or fusion protein of the invention includes a VH domain, the VH domain having an amino acid sequence selected from the group consisting of SEQ ID NO: 2; SEQ ID NO: 6; SEQ ID NO: 10; SEQ ID NO: 14; SEQ ID NO: 18; SEQ ID NO: 22; SEQ ID NO: 26; SEQ ID NO: 30; SEQ ID NO: 34; SEQ ID NO: 36; and SEQ ID NO: 40, and a diagnostic agent, detectable agent or therapeutic agent.

In some embodiments, a conjugated or fusion protein of the invention includes a VL domain, the VL domain having VL CDR1, VL CDR2 and VL CDR3 amino acid sequences, wherein the VL CDR1 is selected from the group consisting of residues 27-37 of SEQ ID NO: 4; residues 27-37 of SEQ ID NO: 8; residues 27-38 of SEQ ID NO: 12; residues 27-38 of SEQ ID NO: 16; residues 27-38 of SEQ ID NO: 20; residues 27-38 of SEQ ID NO: 24; residues 27-37 of SEQ ID NO: 28; residues 27-37 of SEQ ID NO: 32; residues 27-32 of SEQ ID NO: 38; and residues 27-38 of SEQ ID NO: 42; the VL CDR2 is selected from the group consisting of residues 55-57 of SEQ ID NO: 4; residues 55-57 of SEQ ID NO: 8; residues 56-58 of SEQ ID NO: 12; residues 56-58 of SEQ ID NO: 16; residues 56-58 of SEQ ID NO: 20; residues 56-58 of SEQ ID NO: 24; residues 55-57 of SEQ ID NO: 28; residues 55-57 of SEQ ID NO: 32; residues 50-52 of SEQ ID NO: 38; and residues 56-58 of SEQ ID NO: 42, and the VL CDR3 is selected from the group consisting of residues 94-102 of SEQ ID NO: 4; residues 94-102 of SEQ ID NO: 8; residues 95-103 of SEQ ID NO: 12; residues 95-103 of SEQ ID NO: 16; residues 95-103 of SEQ ID NO: 20; residues 95-103 of SEQ ID NO: 24; residues 94-102 of SEQ ID NO: 28; residues 94-102 of SEQ ID NO: 32; residues 89-97 of SEQ ID NO: 38; and residues 95-103 of SEQ ID NO: 42, and a diagnostic agent, detectable agent or therapeutic agent.

In other embodiments, a conjugated or fusion protein of the invention includes a VL domain, the VL domain having VL CDR1, VL CDR2, and VL CDR3 amino acid sequences selected from the group consisting of residues 27-37, residues 55-57, and residues 94-102 of SEQ ID NO: 4; residues 27-37, residues 55-57, and residues 94-102 of SEQ ID NO: 8; residues 27-38, residues 56-58, and residues 95-103 of SEQ ID NO: 12; residues 27-38, residues 56-58, and residues 95-103 of SEQ ID NO: 16; residues 27-38, residues 56-58, and residues 95-103 of SEQ ID NO: 20; residues 27-38, residues 56-58, and residues 95-103 of SEQ ID NO: 24; residues 27-37, residues 55-57, and residues 94-102 of SEQ ID NO: 28; residues 27-37, residues 55-57, and residues 94-102 of SEQ ID NO: 32; residues 27-32, residues 50-52, and residues 89-97 of SEQ ID NO: 38; and residues 27-38, residues 56-58, and residues 95-103 of SEQ ID NO: 42, and a diagnostic agent, detectable agent or therapeutic agent.

In some other aspects, a conjugated or fusion protein of the invention includes a VL domain, the VL domain an amino acid sequence selected from the group consisting of SEQ ID NO: 4; SEQ ID NO: 8; SEQ ID NO: 12; SEQ ID NO: 16; SEQ ID NO: 20; SEQ ID NO: 24; SEQ ID NO: 28; SEQ ID NO: 32; SEQ ID NO: 38; and SEQ ID NO: 42, and a diagnostic agent, detectable agent or therapeutic agent.

In some embodiments, a conjugated or fusion protein of the invention includes a VH domain and a VL domain, wherein the VH domain has an amino acid sequence selected from the group consisting of SEQ ID NO: 2; SEQ ID NO: 6; SEQ ID NO: 10; SEQ ID NO: 14; SEQ ID NO: 18; SEQ ID NO: 22; SEQ ID NO: 26; SEQ ID NO: 30; SEQ ID NO: 34; SEQ ID NO: 36; and SEQ ID NO: 40; and the VL domain has an amino acid sequence selected from the group consisting of SEQ ID NO: 4; SEQ ID NO: 8; SEQ ID NO: 12; SEQ ID NO: 16; SEQ ID NO: 20; SEQ ID NO: 24; SEQ ID NO: 28; SEQ ID NO: 32; SEQ ID NO: 38; and SEQ ID NO: 42, and a diagnostic agent, detectable agent or therapeutic agent.

In some other embodiments, a conjugated or fusion protein of the invention includes a VH domain and a VL domain, wherein the VH domain and the VL domain respectively have an amino acid sequence from the group consisting of SEQ ID NO: 2 and SEQ ID NO: 4; SEQ ID NO: 6 and SEQ ID NO: 8; SEQ ID NO: 10 and SEQ ID NO: 12; SEQ ID NO: 14 and SEQ ID NO: 16; SEQ ID NO: 18 and SEQ ID NO: 20; SEQ ID NO: 22 and SEQ ID NO: 24; SEQ ID NO: 26 and SEQ ID NO: 28; SEQ ID NO: 30 and SEQ ID NO: 32; SEQ ID NO: 34 and SEQ ID NO: 38; SEQ ID NO: 36 and SEQ ID NO: 38; and SEQ ID NO: 40 and SEQ ID NO: 42, and a diagnostic agent, detectable agent or therapeutic agent.

Methods for fusing or conjugating diagnostic agents, detectable agents or therapeutic agents (including polypeptides) to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies 84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), Thorpe et al., 1982, Immunol. Rev. 62:119-58; U.S. Pat. Nos. 5,336,603, 5,622,929, 5,359,046, 5,349,053, 5,447,851, 5,723,125, 5,783,181, 5,908,626, 5,844,095, 5,112,946, 7,981,695, 8,039,273, 8,142,784; U.S. Publications 2009/0202536, 2010/0034837, 2011/0137017, 2011/0280891, 2012/0003247; EP 307,434; EP 367,166; EP 394,827; PCT publications WO 91/06570, WO 96/04388, WO 96/22024, WO 97/34631, and WO 99/04813; Ashkenazi et al., Proc. Natl. Acad. Sci. USA, 88: 10535-10539, 1991; Traunecker et al., Nature, 331:84-86, 1988; Zheng et al., J. Immunol., 154:5590-5600, 1995; Vil et al., Proc. Natl. Acad. Sci. USA, 89:11337-11341, 1992; and Senter, Current Opinion in Chemical Biology, 13:235-244 (2009), which are incorporated herein by reference in their entireties.

In another aspect, a diagnostic agent, detectable agent or therapeutic agent can be attached at the hinge region of a reduced antibody component via disulfide bond formation. Alternatively, such agents can be attached to the antibody component using a heterobifunctional cross-linker, such as N-succinyl 3-(2-pyridyldithio)proprionate (SPDP). Yu et al., Int. J. Cancer 56: 244 (1994). General techniques for such conjugation are well known in the art. See, for example, Wong, CHEMISTRY OF PROTEIN CONJUGATION AND CROSS-LINKING (CRC Press 1991); Upeslacis et al., "Modification of Antibodies by Chemical Methods," in MONOCLONAL ANTIBODIES: PRINCIPLES AND APPLICATIONS, Birch et al. (eds.), pages 187-230 (Wiley-Liss, Inc. 1995); Price, "Production and Characterization of Synthetic Peptide-Derived Antibodies," in MONOCLONAL ANTIBODIES: PRODUCTION, ENGINEERING AND CLINICAL APPLICATION, Ritter et al. (eds.), pages 60-84 (Cambridge University Press 1995).

Alternatively, a diagnostic agent, detectable agent or therapeutic agent can be conjugated via a carbohydrate moiety in the Fc region of the antibody. Methods for conjugating peptides to antibody components via an antibody carbohydrate moiety are well known to those of skill in the art. See, for example, Shih et al., Int. J. Cancer. 41:832-839 (1988); Shih et al., Int. J. Cancer. 46:1101-1106 (1990); and Shih et al., U.S. Pat. No. 5,057,313, all of which are incorporated in their entirety by reference. The general method involves reacting an antibody component having an oxidized carbohydrate portion with a carrier polymer that has at least one free amine function and that is loaded with a plurality of peptide. This reaction results in an initial Schiff base (imine) linkage, which can be stabilized by reduction to a secondary amine to form the final conjugate.

However, if the Fc region is absent, for example, if an antibody functional fragment as provided herein is desirable, it is still possible to attach a diagnostic agent, a detectable agent or a therapeutic agent. A carbohydrate moiety can be introduced into the light chain variable region of a full-length antibody or antibody fragment. See, for example, Leung et al., J. Immunol., 154: 5919 (1995); U.S. Pat. Nos. 5,443,953 and 6,254,868, all of which are incorporated in their entirety by reference. The engineered carbohydrate moiety is used to attach the diagnostic agent, detectable agent or therapeutic agent.

The therapeutic agent conjugated or recombinantly fused to an antibody or functional fragment of the invention that binds to GD2 can be chosen to achieve the desired prophylactic or therapeutic effect(s). It is understood that it is within the skill level of a clinician or other medical personnel to consider the following when deciding which therapeutic agent to conjugate or recombinantly fuse to an antibody or functional fragment of the invention: the nature of the disease, the severity of the disease, and the condition of the subject.

A conjugate or fusion antibody or functional fragment of the invention that is detectably labeled as provided herein and binds to GD2 can be used for diagnostic purposes to detect, diagnose, or monitor a disease, wherein the cells that cause or are associated with the disease express GD2. For example, as provided herein, cancer cells and tumors have been shown to express GD2, such as, but not limited to, neuroblastoma, osteosarcomas and other subsets of sarcomas, melanomas, gliomas, small cell lung cancer, breast cancer and breast cancer stem cells, medulloblastoma, and astrocytoma. Other types of sarcomas include, but are not limited be soft tissue sarcoma, chondrosarcoma, liposarcoma, and leiomyosarcoma. Soft tissue sarcomas include, but are not limited to aveolar soft part sarcoma, angiosarcoma, epithelioid sarcoma, extraskeletal chondrosarcoma, extraskeletal osteosarcoma, fibrosarcoma, gastrointestinal stromal tumor, liposarcoma, malignant peripheral nerve sheath tumor, Neurofibrosarcoma, rhabdomyosarcoma.

Accordingly, the invention provides methods for detecting cancer or a tumor formation in a subject by administering an effective amount of a conjugate or fusion antibody or functional fragment of the invention to a subject in need thereof. In some aspects, the detection method can further include assaying the expression of a GD2 on the cells or a tissue sample of a subject using one or more conjugates or fusion antibodies or functional fragments of the invention that bind to GD2; and comparing the level of the GD2 with a control level, e.g., levels in normal tissue samples (e.g., from a subject not having a disease, or from the same subject before disease onset), whereby an increase in the assayed level of GD2 compared to the control level of the GD2 is indicative of the disease. Such diagnostic methods can allow health professionals to employ preventative measures or aggressive treatment earlier than otherwise possible thereby preventing the development or further progression of the disease.

An antibody or functional fragment of the invention can also be used to assay GD2 antigen levels in a biological sample using classical immunohistological methods as provided herein or as well known to those of skill in the art (e.g., see Jalkanen et al., 1985, J. Cell. Biol. 101:976-985; and Jalkanen et al., 1987, J. Cell. Biol. 105:3087-3096). Other antibody-based methods useful for detecting GD2 include immunoassays, such as the enzyme linked immunosorbent assay (ELISA) and the radioimmunoassay (MA). Suitable antibody assay labels are known in the art and include enzyme labels, such as, glucose oxidase; radioisotopes, such as iodine ($^{125}$I, $^{121}$I) carbon ($^{14}$C), sulfur ($^{35}$S), tritium ($^{3}$H), indium ($^{121}$In), and technetium ($^{99}$Tc); luminescent labels, such as luminol; and fluorescent labels, such as fluorescein and rhodamine, and biotin.

In one aspect, the invention provides for the detection and diagnosis of disease in a human. In one embodiment, diagnosis includes: a) administering (for example, parenterally, subcutaneously, or intraperitoneally) to a subject an effective amount of a conjugate or fusion protein of the invention that binds to GD2; b) waiting for a time interval following the administering for permitting the conjugate or fusion protein to preferentially concentrate at sites in the subject where GD2 is expressed (and, in some aspects, for unbound conjugate or fusion protein to be cleared to background level); c) determining background level; and d) detecting the conjugate or fusion protein in the subject, such that detection of conjugate or fusion protein above the background level indicates that the subject has a disease. Background level can be determined by various methods including, comparing the amount of conjugate or fusion protein detected to a standard value previously determined for a particular system.

It is understood that the size of the subject and the imaging system used will determine the quantity of imaging moiety needed to produce diagnostic images and can be readily determined by one of skill in the art. For example, in the case of a radioisotope conjugated to an antibody or functional fragment of the invention, for a human subject, the quantity of radioactivity injected will normally range from about 5 to 20 millicuries of $^{99}$Tc. The conjugate will then preferentially accumulate at the location of cells which express GD2. In vivo tumor imaging is described in S. W. Burchiel et al., "Immunopharmacokinetics of Radiolabeled Antibodies and Their Fragments." (Chapter 13 in Tumor Imaging: The Radiochemical Detection of Cancer, S. W. Burchiel and B. A. Rhodes, eds., Masson Publishing Inc. (1982).

Depending on several variables, including the type of detectable agent used and the mode of administration, the time interval following the administration for permitting the conjugate to preferentially concentrate at sites in the subject and for unbound conjugate to be cleared to background level is 6 to 48 hours or 6 to 24 hours or 6 to 12 hours. In another embodiment, the time interval following administration is 5 to 20 days or 5 to 10 days. In one embodiment, monitoring of a disease is carried out by repeating the method for diagnosing as provided herein, for example, one month after initial diagnosis, six months after initial diagnosis, one year after initial diagnosis, or longer.

The presence of the conjugate or fusion protein can be detected in the subject using methods known in the art for in vivo scanning. These methods depend upon the type of detectable agent used. A skilled artisan will be able to determine the appropriate method for detecting a particular detectable agent. Methods and devices that can be used in the diagnostic methods of the invention include, but are not limited to, computed tomography (CT), whole body scan such as position emission tomography (PET), magnetic resonance imaging (MM), and sonography. In one embodiment, an antibody or function fragment of the invention is conjugated to a radioisotope and is detected in the subject using a radiation responsive surgical instrument. In another embodiment, an antibody or function fragment of the invention is conjugated to a fluorescent compound and is detected in the subject using a fluorescence responsive scanning instrument. In another embodiment, an antibody or function fragment of the invention is conjugated to a positron emitting metal, such as zirconium ($^{89}$Zr) or any other positron emitting metal provided herein or that is well known in the art to be detectable by positron emission-tomography, and is detected in the subject using positron emission-tomography. In yet another embodiment, an antibody or function fragment of the invention is conjugated to a paramagnetic label and is detected in a subject using magnetic resonance imaging (MRI).

In one embodiment, the invention provides a pharmaceutical composition having an antibody or a functional fragment of the invention and a pharmaceutically acceptable carrier. A pharmaceutically acceptable carrier that can be used in the pharmaceutical compositions of the invention include any of the standard pharmaceutical carriers known in the art, such as phosphate buffered saline solution, water and emulsions such as an oil and water emulsion, and various types of wetting agents. These pharmaceutical compositions can be prepared in liquid unit dose forms or any other dosing form that is sufficient for delivery of the antibody or functional fragment of the invention to the target area of the subject in need of treatment. For example, the pharmaceutical compositions can be prepared in any manner appropriate for the chosen mode of administration, e.g., intravascular, intramuscular, sub-cutaneous, intraperitoneal, etc. Other optional components, e.g., pharmaceutical grade stabilizers, buffers, preservatives, excipients and the like can be readily selected by one of skill in the art. The preparation of a pharmaceutically composition, having due regard to pH, isotonicity, stability and the like, is within the level of skill in the art.

Pharmaceutical formulations containing one or more antibodies or functional fragments of the invention provided herein can be prepared for storage by mixing the antibody having the desired degree of purity with optional physiologically acceptable carriers, excipients or stabilizers (*Remington's Pharmaceutical Sciences* (1990) Mack Publishing Co., Easton, Pa.), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

Thus, in some embodiments, the invention provides a method for treating or preventing a disease in a subject in need thereof. The methods of the invention can include administering a therapeutically effective amount of a pharmaceutical composition provided herein to the subject. For example, the pharmaceutical composition can include one or more antibody or functional fragment provided herein. Diseases that can be treated or prevented using the methods of the invention include cancer, tumor formation and/or metastasis. In particular, the methods of the invention are useful for treating cancers or tumor formation wherein the cancer cells or tumor expresses GD2. Non-limiting examples of cancers or tumors that can be treated or prevented using the methods of the invention include neuroblastoma, osteosarcomas and other subsets of sarcomas, melanomas, gliomas, small cell lung cancer, breast cancer, medulloblastoma, and astrocytoma. Other types of sarcomas include, but are not limited to soft tissue sarcoma, chondrosarcoma, liposarcoma, and leiomyosarcoma. Soft tissue sarcomas include, but are not limited to aveolar soft part sarcoma, angiosarcoma, epithelioid sarcoma, extraskeletal chondrosarcoma, extraskeletal osteosarcoma, fibrosarcoma, gastrointestinal stromal tumor, liposarcoma, malignant peripheral nerve sheath tumor, Neurofibrosarcoma, rhabdomyosarcoma. Breast cancer stem cells are also known to express GD2. Battulal V L et al., *Ganglioside GD2 identifies breast cancer stem cells and promotes tumorigenesis*. J CLIN INVEST. 122 (6):2066-2078 (2012).

Accordingly, in some aspects, the invention provides a method for treating cancer or a tumor formation in a subject in need thereof by administering a therapeutically effective amount of a pharmaceutical composition having an antibody or functional fragment thereof, wherein the antibody or functional fragment binds to GD2 and has a variable heavy chain (VH) domain, the domain having VH CDR1, VH CDR2 and VH CDR3 amino acid sequences, wherein the VH CDR1 amino acid sequence is selected from the group consisting of residues 26-33 of SEQ ID NO: 2; residues 26-33 of SEQ ID NO: 6; residues 26-33 of SEQ ID NO: 10; residues 26-33 of SEQ ID NO: 14; residues 26-33 of SEQ ID NO: 18; residues 26-33 of SEQ ID NO: 22; residues 26-33 of SEQ ID NO: 26; residues 26-33 of SEQ ID NO: 30; residues 26-33 of SEQ ID NO: 34; residues 26-33 of SEQ ID NO: 36; and residues 26-33 of SEQ ID NO: 40; the VH CDR2 amino acid sequence is selected from the group consisting of residues 51-58 of SEQ ID NO: 2; residues 51-58 of SEQ ID NO: 6; residues 51-58 of SEQ ID NO: 10; residues 51-58 of SEQ ID NO: 14; residues 51-58 of SEQ ID NO: 18; residues 51-58 of SEQ ID NO: 22; residues 51-58 of SEQ ID NO: 26; residues 51-58 of SEQ ID NO: 30; residues 51-58 of SEQ ID NO: 34; residues 51-58 of SEQ ID NO: 36; and residues 51-58 of SEQ ID NO: 40; and the VH CDR3 amino acid sequence is selected from the group consisting of residues 97-109 of SEQ ID NO: 2; residues 97-109 of SEQ ID NO: 6; residues 97-108 of SEQ ID NO: 10; residues 97-108 of SEQ ID NO: 14; residues 97-108 of SEQ ID NO: 18; residues 97-108 of SEQ ID NO: 22; residues 97-109 of SEQ ID NO: 26; residues 97-109 of SEQ ID NO: 30; residues 97-110 of SEQ ID NO: 34; residues 97-110 of SEQ ID NO: 36; and residues 97-108 of SEQ ID NO: 40.

In some other aspects, the invention provides a method for treating cancer or a tumor formation in a subject in need thereof by administering a therapeutically effective amount of a pharmaceutical composition having an antibody or functional fragment thereof, wherein the antibody or functional fragment binds to GD2 and has a variable heavy chain (VH) domain, the VH domain having VH CDR1, VH CDR2, and VH CDR3 amino acid sequences selected from the group consisting of residues 26-33, residues 51-58, and residues 97-109 of SEQ ID NO: 2; residues 26-33, residues 51-58, and residues 97-109 of SEQ ID NO: 6; residues 26-33, residues 51-58, and residues 97-108 of SEQ ID NO: 10; residues 26-33, residues 51-58, and residues 97-108 of SEQ ID NO: 14; residues 26-33, residues 51-58, and residues 97-108 of SEQ ID NO: 18; residues 26-33, residues 51-58, and residues 97-108 of SEQ ID NO: 22; residues 26-33, residues 51-58, and residues 97-109 of SEQ ID NO: 26; residues 26-33, residues 51-58, and residues 97-109 of SEQ ID NO: 30; residues 26-33, residues 51-58, and residues 97-110 of SEQ ID NO: 34; residues 26-33, residues 51-58, and residues 97-110 of SEQ ID NO: 36; and residues 26-33, residues 51-58, and residues 97-108 of SEQ ID NO: 40.

In yet other aspects, the invention provides a method for treating cancer or a tumor formation in a subject in need thereof by administering a therapeutically effective amount of a pharmaceutical composition having an antibody or functional fragment thereof, wherein the antibody or functional fragment binds to GD2 and has a variable heavy chain (VH) domain, the VH domain having an amino acid sequence selected from the group consisting of SEQ ID NO: 2; SEQ ID NO: 6; SEQ ID NO: 10; SEQ ID NO: 14; SEQ ID NO: 18; SEQ ID NO: 22; SEQ ID NO: 26; SEQ ID NO: 30; SEQ ID NO: 34; SEQ ID NO: 36; and SEQ ID NO: 40.

In some embodiments, the invention provides a method for treating cancer or a tumor formation in a subject in need thereof by administering a therapeutically effective amount of a pharmaceutical composition having an antibody or functional fragment thereof, wherein the antibody or functional fragment binds to GD2 and has a variable light chain (VL) domain, the VL domain having VL CDR1, VL CDR2 and VL CDR3 amino acid sequences, wherein the VL CDR1 is selected from the group consisting of residues 27-37 of SEQ ID NO: 4; residues 27-37 of SEQ ID NO: 8; residues 27-38 of SEQ ID NO: 12; residues 27-38 of SEQ ID NO: 16; residues 27-38 of SEQ ID NO: 20; residues 27-38 of SEQ ID NO: 24; residues 27-37 of SEQ ID NO: 28; residues 27-37 of SEQ ID NO: 32; residues 27-32 of SEQ ID NO: 38; and residues 27-38 of SEQ ID NO: 42; the VL CDR2 is selected from the group consisting of residues 55-57 of SEQ ID NO: 4; residues 55-57 of SEQ ID NO: 8; residues 56-58 of SEQ ID NO: 12; residues 56-58 of SEQ ID NO: 16; residues 56-58 of SEQ ID NO: 20; residues 56-58 of SEQ ID NO: 24; residues 55-57 of SEQ ID NO: 28; residues 55-57 of SEQ ID NO: 32; residues 50-52 of SEQ ID NO: 38; and residues 56-58 of SEQ ID NO: 42, and the VL CDR3 is selected from the group consisting of residues 94-102 of SEQ ID NO: 4; residues 94-102 of SEQ ID NO: 8; residues 95-103 of SEQ ID NO: 12; residues 95-103 of SEQ ID NO: 16; residues 95-103 of SEQ ID NO: 20; residues 95-103 of SEQ ID NO: 24; residues 94-102 of SEQ ID NO: 28; residues 94-102 of SEQ ID NO: 32; residues 89-97 of SEQ ID NO: 38; and residues 95-103 of SEQ ID NO: 42.

In some aspects, the present invention provides a method for treating cancer or a tumor formation in a subject in need thereof by administering a therapeutically effective amount of a pharmaceutical composition having an antibody or functional fragment thereof, wherein the antibody or functional fragment binds to GD2 and has a variable light chain (VL) domain, the VL domain having VL CDR1, VL CDR2, and VL CDR3 amino acid sequences selected from the group consisting of residues 27-37, residues 55-57, and residues 94-102 of SEQ ID NO: 4; residues 27-37, residues 55-57, and residues 94-102 of SEQ ID NO: 8; residues 27-38, residues 56-58, and residues 95-103 of SEQ ID NO: 12; residues 27-38, residues 56-58, and residues 95-103 of SEQ ID NO: 16; residues 27-38, residues 56-58, and residues 95-103 of SEQ ID NO: 20; residues 27-38, residues 56-58, and residues 95-103 of SEQ ID NO: 24; residues 27-37, residues 55-57, and residues 94-102 of SEQ ID NO: 28; residues 27-37, residues 55-57, and residues 94-102 of SEQ ID NO: 32; residues 27-32, residues 50-52, and residues 89-97 of SEQ ID NO: 38; and residues 27-38, residues 56-58, and residues 95-103 of SEQ ID NO: 42.

In some other aspects, the present invention provides a method for treating cancer or a tumor formation in a subject in need thereof by administering a therapeutically effective amount of a pharmaceutical composition having an antibody or functional fragment thereof, wherein the antibody or functional fragment binds to GD2 and has a variable light chain (VL) domain, the VL domain having an amino acid sequence selected from the group consisting of SEQ ID NO: 4; SEQ ID NO: 8; SEQ ID NO: 12; SEQ ID NO: 16; SEQ ID NO: 20; SEQ ID NO: 24; SEQ ID NO: 28; SEQ ID NO: 32; SEQ ID NO: 38; and SEQ ID NO: 42.

In some embodiments, the present invention provides a method for treating cancer or a tumor formation in a subject in need thereof by administering a therapeutically effective amount of a pharmaceutical composition having an antibody or functional fragment thereof that binds to GD2, the antibody or functional fragment thereof including a variable heavy chain (VH) domain and a variable light chain (VL) domain, wherein the VH domain has an amino acid sequence selected from the group consisting of SEQ ID NO: 2; SEQ ID NO: 6; SEQ ID NO: 10; SEQ ID NO: 14; SEQ ID NO: 18; SEQ ID NO: 22; SEQ ID NO: 26; SEQ ID NO: 30; SEQ ID NO: 34; SEQ ID NO: 36; and SEQ ID NO: 40; and the VL domain has an amino acid sequence selected from the group consisting of SEQ ID NO: 4; SEQ ID NO: 8; SEQ ID NO: 12; SEQ ID NO: 16; SEQ ID NO: 20; SEQ ID NO: 24; SEQ ID NO: 28; SEQ ID NO: 32; SEQ ID NO: 38; and SEQ ID NO: 42.

In some other embodiments, the present invention provides a method for treating cancer or a tumor formation in a subject in need thereof by administering a therapeutically effective amount of a pharmaceutical composition having an antibody or functional fragment thereof that binds to GD2, the antibody or functional fragment thereof including a variable heavy chain (VH) domain and a variable light chain (VL) domain, wherein the VH domain and the VL domain respectively have an amino acid sequence from the group consisting of SEQ ID NO: 2 and SEQ ID NO: 4; SEQ ID NO: 6 and SEQ ID NO: 8; SEQ ID NO: 10 and SEQ ID NO: 12; SEQ ID NO: 14 and SEQ ID NO: 16; SEQ ID NO: 18 and SEQ ID NO: 20; SEQ ID NO: 22 and SEQ ID NO: 24; SEQ ID NO: 26 and SEQ ID NO: 28; SEQ ID NO: 30 and SEQ ID NO: 32; SEQ ID NO: 34 and SEQ ID NO: 38; SEQ ID NO: 36 and SEQ ID NO: 38; and SEQ ID NO: 40 and SEQ ID NO: 42.

Formulations, such as those described herein, can also contain more than one active compound as necessary for the particular disease being treated. In certain embodiments, formulations include an antibody or functional fragment of the invention and one or more active compounds with complementary activities that do not adversely affect each other. Such molecules are suitably present in combination in amounts that are effective for the purpose intended. For example, an antibody or functional fragment of the invention can be combined with one or more other therapeutic agents. Such combined therapy can be administered to the subject concurrently or successively.

Thus, in some embodiments, invention provides a method for treating or preventing a disease by administering a therapeutically effective amount of a pharmaceutical composition provided herein to a subject in need thereof, wherein the pharmaceutical composition includes an antibody or functional fragment of the invention and a second therapeutic agent. The appropriate second therapeutic agent can be readily determined by one of ordinary skill in the art as discussed herein. In one aspect, the second therapeutic agent is a chemotherapeutic agent or an immunotherapeutic agent.

The pharmaceutical compositions provided herein contain therapeutically effective amounts of one or more of the antibodies of the invention provided herein, and optionally one or more additional therapeutic agents, in a pharmaceutically acceptable carrier. Such pharmaceutical compositions are useful in the prevention, treatment, management or amelioration of a disease, such as cancer or tumor formation, or one or more of the symptoms thereof.

The pharmaceutical compositions can contain one or more antibodies or functional fragments of the invention. In one embodiment, the antibodies or functional fragments are formulated into suitable pharmaceutical preparations, such as sterile solutions or suspensions for parenteral administration. In one embodiment, the antibodies or functional fragments provided herein are formulated into pharmaceutical compositions using techniques and procedures well known in the art (see, e.g., Ansel (1985) *Introduction to Pharmaceutical Dosage Forms*, 4$^{th}$ Ed., p. 126).

An antibody or functional fragment of the invention can be included in the pharmaceutical composition in a therapeutically effective amount sufficient to exert a therapeutically useful effect in the absence of undesirable side effects on the subject treated. The therapeutically effective concentration can be determined empirically by testing the compounds in in vitro and in vivo systems using routine methods and then extrapolated therefrom for dosages for humans. The concentration of an antibody or functional fragment in the pharmaceutical composition will depend on, e.g., the physicochemical characteristics of the antibody or functional fragment, the dosage schedule, and amount administered as well as other factors well known to those of skill in the art.

In one embodiment, a therapeutically effective dosage produces a serum concentration of an antibody or functional fragment of from about 0.1 ng/ml to about 50-100 µg/ml. The pharmaceutical compositions, in another embodiment, provide a dosage of from about 0.001 mg to about 500 mg of antibody per kilogram of body weight per day. Pharmaceutical dosage unit forms can be prepared to provide from about 0.01 mg, 0.1 mg or 1 mg to about 30 mg, 100 mg or 500 mg, and in one embodiment from about 10 mg to about 500 mg of the antibody or functional fragment and/or a combination of other optional essential ingredients per dosage unit form.

The antibody or functional fragment of the invention can be administered at once, or can be divided into a number of smaller doses to be administered at intervals of time. It is understood that the precise dosage and duration of treatment is a function of the disease being treated and can be determined empirically using known testing protocols or by extrapolation from in vivo or in vitro test data. It is to be noted that concentrations and dosage values can also vary with the severity of the condition to be alleviated. It is to be further understood that for any particular subject, specific dosage regimens can be adjusted over time according to the individual need and the professional judgment of the person administering or supervising the administration of the compositions, and that the concentration ranges set forth herein are exemplary only and are not intended to limit the scope or practice of the claimed compositions.

Upon mixing or addition of the antibody or functional fragment of the invention, the resulting mixture can be a solution, suspension or the like. The form of the resulting mixture depends upon a number of factors, including the intended mode of administration and the solubility of the compound in the selected carrier or vehicle. The effective concentration is sufficient for ameliorating the symptoms of the disease, disorder or condition treated and can be empirically determined.

The pharmaceutical compositions are provided for administration to humans and animals in unit dosage forms, such as sterile parenteral solutions or suspensions containing suitable quantities of the compounds or pharmaceutically acceptable derivatives thereof. The antibody or functional fragment can be, in one embodiment, formulated and administered in unit-dosage forms or multiple-dosage forms. Unit-dose forms refers to physically discrete units suitable for human and animal subjects and packaged individually as is known in the art. Each unit-dose contains a predetermined quantity of the antibody or functional fragment of the invention sufficient to produce the desired therapeutic effect, in association with the required pharmaceutical carrier, vehicle or diluent. Examples of unit-dose forms include ampoules and syringes. Unit-dose forms can be administered in fractions or multiples thereof. A multiple-dose form is a plurality of identical unit-dosage forms packaged in a single container to be administered in segregated unit-dose form. Examples of multiple-dose forms include vials or bottles of pints or gallons. Hence, multiple dose form is a multiple of unit-doses which are not segregated in packaging.

In one embodiment, one or more antibody or functional fragment of the invention is in a liquid pharmaceutical formulation. Liquid pharmaceutically administrable compositions can, for example, be prepared by dissolving, dispersing, or otherwise mixing an antibody or functional fragment as provided herein and optional pharmaceutical adjuvants in a carrier, such as, for example, water, saline, aqueous dextrose, glycerol, glycols, ethanol, and the like, to thereby form a solution. If desired, the pharmaceutical composition to be administered can also contain minor amounts of nontoxic auxiliary substances such as wetting agents, emulsifying agents, solubilizing agents, pH buffering agents and the like, for example, acetate, sodium citrate, cyclodextrine derivatives, sorbitan monolaurate, triethanolamine sodium acetate, triethanolamine oleate, and other such agents. Actual methods of preparing such dosage forms are known, or will be apparent, to those skilled in this art; for example, see Remington's Pharmaceutical Sciences (1990) Mack Publishing Co., Easton, Pa.

Methods for administering a pharmaceutical composition of the invention are well known in the art. It is understood that the appropriate route of administration of a pharmaceutical composition can be readily determined by a skilled clinician. Exemplary routes of administration include intravenous injection, intramuscular injection, intradermal injection or subcutaneous injection. Moreover, it is understood that the formulation of the pharmaceutical composition can be readily adjusted to accommodate the route of administration. The invention also provides that following administration of a pharmaceutical composition of the invention, delayed, successive and/or repeated dosages of one or more pharmaceutical composition as provided herein can be administered to the subject.

The methods of the invention for treating a disease is intended to include (1) preventing the disease, i.e., causing the clinical symptoms of the disease not to develop in a subject that can be predisposed to the disease but does not yet experience or display symptoms of the disease; (2) inhibiting the disease, i.e., arresting or reducing the development of the disease or its clinical symptoms; or (3) relieving the disease, i.e., causing regression of the disease or its clinical symptoms. The methods of the invention for preventing a disease is intended to include forestalling of a clinical symptom indicative of cancer or tumor formation. Such forestalling includes, for example, the maintenance of normal physiological indicators in a subject. Therefore, preventing can include the prophylactic treatment of a subject to guard them from the occurrence of tumor metastasis.

The therapeutically effective amount of the pharmaceutical composition used in the methods of the invention will vary depending on the pharmaceutical composition used, the disease and its severity and the age, weight, etc., of the subject to be treated, all of which is within the skill of the attending clinician. A subject that that can be treated by the methods of the invention include a vertebrate, preferably a mammal, more preferably a human.

It is understood that modifications which do not substantially affect the activity of the various embodiments of this invention are also provided within the definition of the invention provided herein. Accordingly, the following examples are intended to illustrate but not limit the present invention.

Example I

Human Monoclonal Antibodies to GD2 have Potent Antitumor Activity

The disialoganglioside GD2 has been found in a wide spectrum of human tumors, including neuroblastoma, osteo sarcomas and other subsets of sarcomas, melanomas, gliomas, small cell lung cancer, breast cancer, medulloblastoma, and astrocytoma. Breast cancer stem cells are also known to express GD2. Battulal V L et al., Ganglioside GD2 identifies breast cancer stem cells and promotes tumorigenesis. J Clin Invest. 122(6):2066-2078 (2012). Gangliosides are ideal targets for monoclonal antibodies (mAb) because of the high antigen density, lack of modulation, relative homogeneity in many tumors and the possibility of up-regulation by cytokines. Accordingly, as described herein, fully human monoclonal antibodies (mAb) against GD2 were generated. Several mAbs were selected based on ELISA and FACS and further characterized. Of the tested antibodies, 1B7, 2H12, 2F7, 2E12, and 31F9V2 showed high levels of complement-dependent cytotoxicity on some cancer cell lines; 1B7, 31F9, 31F9V2, and 2F7 showed high levels of antibody-dependent cell-mediated cytotoxicity on some cancer cell lines; and the antitumor activity was also confirmed in in vivo models. Based on the potential of GD2 as a target for immune attack and their affinity, specificity, and effector functions, anti-GD2 mAb have clinical utility in the treatment of cancer.

Materials, Cells, and Antibodies

Antigens: GD2-PAA-biotin (cat #0832-BP), GM2-PAA-Biotin (cat #0835-BP) and GD3-PAA-biotin (cat #0898-BP) were purchased from Lectinity (Moscow, Russia). Tn-PAA-biotin (cat #01-010), sTn-PAA-biotin (cat #01-059), TF-PAA-biotin (cat #01-023) and sLeA-PAA-biotin (cat #01-044) were purchased from Glycotech (Gaithersburg, Md.). GD2-ceramide, GM2-ceramide, GD3-ceramide, Fucosyl-GM1-ceramide and Globo-H-biotin were obtained from MSKCC (New York, N.Y.). MUC1 peptide-biotin (cat #353951) was purchased from American Peptide Company (Sunnyvale, Calif.). GM3-ceramide (cat #1503) was purchased from Matreya (Pleasant Gap, Pa.). Ceramide antigens were dissolved in Methanol and all others were resuspended in PBS at 1 mg/ml.

Cell Lines: H524, Lan1-luc, BxPC3, SK-MEL19, ST88, LS141, SaO52 cell line were obtained from MSKCC (New York, N.Y.). Capan2 (ATCC, HTB-80), DMS79 (ATCC, CRL-2049), Jurkat (ATCC, TIB-152), SK-MEL28 (ATCC, HTB72), HT29, (HTB-38) and MCF7 (ATCC, HTB22) were purchased from ATCC (Manassas, Va.). TC-71 (AAC516) was purchased from Leibniz Institute DSMZ (Braunschweig, Germany).

Generation of anti-GD2 mAb-producing hybridomas and lymphoblastoid cell lines (LCL): Blood samples were obtained from patients in trials with GD2-/GD3-KLH conjugate vaccine in patients with melonoma and GD2-/GD3-/GM2-KLH trivalent vaccine in patients with sarcoma. The melanoma Phase I trial was done at MSKCC while the sarcoma trial was a multicenter, blinded Phase II study. All samples were obtained under respective institutional and FDA approved IRB protocol and IND. Human B cells were isolated from approximately 80-90 ml of blood by RosetteSep Human B Cell Enrichment Cocktail (cat #15024, StemCell Technologies, Vancouver, BC, Canada) using gradient centrifugation on Histopaque-1077 (cat #10771, Sigma, St Louis, Mo.). The B cells were cultured in RPMI-1640 medium (cat #10-040-CV, Mediatech, Manassas, Va.) supplemented with L-Glutamine (cat #25030081, Life Technologies, Carlsbad, Calif.), non-essential amino acids (cat #NE-01), sodium pyruvate (cat #SP-90), vitamin (cat #ME-30), penicillin/streptomycin (PS-20), 10% FBS (cat #FB-01) from Omega Scientific, Tarzana, Calif., and a mixture of stimulants and cytokines. Five to seven days later cells were fused by electrofusion to P3X63Ag8.653 myeloma cells (cat #PTA-8434, ATCC, Manassas, Va.). LCLs were generated by infecting the B cell with EBV (B95-8 culture supernatant) in presence of IL2 and R848 or PS2006. Anti-GD2 producing hybridomas and LCLs were identified using a GD2 specific ELISA.

ELISA: For the biotinylated Antigens: 50 µl/well of NeutrAvidin (cat #31000, Thermo Scientific, Rockford, Ill.) was coated on the ELISA plate (cat #655061, Greiner Bio-One, Monroe, N.C.) at 4 µg/ml and incubated at RT for 2 hrs. The plate was blocked with 1.25% human serum albumin (HuSA) (cat #HA25S, Monobind, Lake Forest, Calif.) for 2 hrs at RT or 4C, O/N. After washing the plate with 0.05% Tween/PBS (PBS-0.05% T) twice, 50 µl/well of biotinylated antigen (final concentration at 2 µg/ml in PBS) or PBS was added and incubated at RT for 30 min or 4° C., 0/N. The plate was washed with PBS-T twice and incubated with 100 µl/well of purified mAbs diluted in 1.25% HuSA at 2 µg/ml for 1 hr at RT. After washing the plate with PBS-0.05% T three times 100 µl/well of secondary antibody, alkaline phosphatase conjugated-anti-human IgG or IgM (1:3000 dilution in 1.25% HuSA, cat #075-1002 and cat #075-1003, respectively, KPL, Gaithersburg, Md.) was added and incubated at RT for 1 hr. The plate was washed four times with PBS-0.05% T. A hundred µl/well pNPP substrate (cat #PI34045, Thermo Scientific, Rockford, Ill.) was added and incubated at RT for 1 hr and the reaction was stopped with 25 µl/well of 2N NaOH.

For the ceramide antigens: 50 µl/well of ceramide antigen (final concentration at 5 µg/ml in EtOH) or EtOH was coated on the 96 well plate (cat #269620, Thermo Scientific, Rockford, Ill.) and incubated at RT over 2 hrs. The plate was washed with PBS once and blocked with 2.5% HuSA at RT for 2 hrs or 4° C., 0/N. The plate was washed with PBS once and incubated with 100 µl/well of purified mAbs diluted in 1.25% HuSA at 2 µg/ml for 1 hr at RT. The plate was washed with PBS twice before adding the $2^{nd}$ antibody as described above. The plate was washed with PBS-0.025% T three times before adding the substrate.

FACS: The cells were resuspended in 200 µl/tube of PBS/1% BSA (cat #A3059, Sigma, St. Louis, Mo.) at $0.25 \times 10^6$ cells/ml. Purified mAb was added to the tube at 2 mg/ml for IgG or 5 mg/ml for IgM and incubated for 40 min at 4° C. After washing with PBS/1% BSA once 200 µl of Fluorophore conjugated antibody, Alexa488-anti-human IgG (cat #H10120, Life Technologies, Carlsbad, Calif.) or Alexa488-anti-human IgM (cat #A21215, Life Technologies, Carlsbad, Calif.) was added to the tube and incubated for 40 min at 4° C. The cells were washed with PBS/1% BSA twice and analyzed with Guava ExpressPro software using the Guava Personal Cell Analysis-96 (PCA-96) System (Millipore, Billerica, Mass.).

Affinity determination: Affinity constants were determined using the principal of Surface Plasmon Resonance (SPR) with a BiaCore 3000 (GE Healthcare, Piscataway, N.J.). Custom synthesized biotin-labeled GD2-polyacrylamide (GD2-PAA-biotin) was obtained from Lectinity Holdings Inc (Moscow, Russia) and was coupled to a streptavidin coated biosensor chip (SA; Cat #BR100398) according to the manufacturer's instructions. One flow cell blocked with HSA and culture medium containing free biotin was used as a reference cell. The binding kinetic parameters were determined from several known concentrations of antibody diluted in HBS-EP buffer (10 mM HEPES pH 7.4, 150 mM NaCl, 3.4 mM EDTA, 0.005% surfactant P20) using the GD2-PAA-biotin coated flow cell. The curve-fitting software provided by the BiaCore instrument was used to calculate the association and dissociation rates.

CDC Assay: The cells were washed with PBS twice, resuspended in 1 ml of PBS at $10^6$ cells/ml/tube and incubated with 12.5 µl/tube of Calcein AM (1 mg/ml in DMSO) (cat #C3100MP, Invitrogen, Carlsbad, Calif.) at 37° C. for 30 min. The labeled cells were washed with medium containing 10% FBS (complete medium) (cat #FB-12, Omega Scientific, Tarzana, Calif.) twice and resuspended in 1 ml of complete medium. The labeled cells (50 µl/well) were incubated with 100 µl well of mAb diluted in complete medium for 15 min at 4C. 50 µl/well of human complements (cat #IPLA-CSER, Innovative Research, Novi, Mich.) diluted in complete medium were added to the wells and incubated at 37° C. for 90 min. The appropriate final dilution for human complement was pre-determined for each cell line (between 1:5 and 1:16). After a centrifuge at 1600 rpm for 8 min supernatant (100 µl/well) were transferred to a new fluorescence 96 well plate (cat #7605, Thermo Scientific, Rockford, Ill.). Each sample was assessed in triplicate. Control samples that receive NP40 are used to determine maximal killing and samples receiving complement alone serve as baseline. The percentage of killed cells is determined by relative fluorescent units and calculated according to the following formula: % killed=(% sample–% complement alone)/(% NP40–% complement alone)*100.

Antibody-dependent cell-mediated cytotoxicity Assay: ADCC Reporter Bioassay Core Kit (cat #G7010) was purchased from Promega (Madison, Wis.) and the assay was performed according to the instruction manual. Briefly, effector cells (Jurkat from the core kit) and GD2 antigen expressing target cells were washed and resuspended in RPMI1640 medium containing 10% low bovine IgG serum (core kit) at 3×10$^6$ cells/ml and 0.5×10$^6$ cells/ml, respectively. The target cells (12,500 cells/25 µl/well) were incubated with 25 µl/well of anti-GD2 mAb (final concentration at 5 µg/ml) or medium only, and the effector cells (75,000/25 µl/well) for 17 hrs at 37° C. 100 µl/well of Bio-Glo luciferase assay substrate (core kit) was added and incubated for 10 min. Relative light unit (RLU) was measured by Synergy 2 luminometer (BioTek, Winooski, Vt.). The effector cells and medium only wells served as baseline RLU. Each sample is tested in triplicate.

Internalization Assay: Internalization of anti-GD2 antibodies were evaluated by measuring the cytotoxic activity of mAb and Hum-ZAP secondary conjugate (cat #IT22, Advanced Targeting Systems, San Diego, Calif.) complex against GD2 expressing cell lines, H524 and Lan1-luc. Cells were plated into a 96 well plate (2,000 cells/90 µl/well) and incubated overnight in duplicates. Anti-GD2 antibody was incubated with Hum-ZAP secondary conjugates at RT according to the manufacturer's instruction. Next, 10 µl/well of mAb and Hum-ZAP complex was added to the cells and incubated for 3 days. The final concentration of the mAb was 10 µg/ml. The assay was performed in triplicate. 25 µl of Thiazolyl Blue Tetrazolium Bromide (cat #M5655, Sigma, St Louis, Mo.) solution (5 mg/ml in PBS) was added to each well and incubated at 37° C. After 2 hrs incubation 100 µl/well of solubilization solution (20% SDS/50% N,N-Dimethylformamide, cat #D4551, Sigam, St Louis, Mo.) was added to each well and incubated for another 4 hrs at 37° C. The OD was measured at 570/690 nm and values obtained with medium alone were used for plate background subtraction. Three parallel cultures without antibody were used to normalize the sample values (Sample/Mean Untreated*100).

Internalization Assay using a pH sensitive Intracellular Fluorescent Probe: Goat anti-human IgG F(ab')2 fragments (Jackson ImmunoResearch, cat #109-006-006) were conjugated with pHAb Amine Reactive Dye (Promega, cat #G9841) according to the manufacturer's protocol. pHAb is a pH sensor dye that shows fluorescence only at acidic pH, which is encountered when the cells take up the antibodies into their lysosomes. In brief, primary antibody (1B7, 31F9, 5A7G3 or no mAb as reagent control) at 6 µg/ml (200 µl/tube) and anti-human IgG F(ab')2-pHAb at 4.5 µg/ml (200 µl/tube) were incubated at RT for 20 min. H524 or TC-71 cells were re-suspended in RPMI1640+10% FBS+ Glutamine+P/S medium at 1.5×10$^6$ cell/ml. Two hundred µl of cells were added to the primary plus secondary antibody mixture and incubated for 40 min at 4° C. The cells were centrifuged and re-suspended in 0.5 ml of culture medium, distributed into a 96 well tissue culture plate and incubated at 37° C., 5% $CO_2$. Samples were taken at 1 hr, 2 hrs, 4 hrs and 24 hrs for flow cytometry analysis using Guava Express Pro software to determine the percentage of positive of cells.

Xenograft transplantation model: Osteosarcoma SaOS2 cells were obtained from ATCC (Cat #HTB-85; Manassas, Va.) and female CB17 SCID mice (5-8 weeks old) were purchased from Taconic (Germantown, N.Y.). SaOS2 cells (1×10$^6$) in 0.1 ml complete growth media were injected via the tail vein on Day 0 using a BD insulin syringe with 28G needle (BD, Franklin Lakes, N.J.) into 10 animals per group. 200 µg mAb (1B7 or 31F9) was injected intraperitoneally on days 1, 4, 8, 11, 14, 21 and 28 post tumor cell injection. Survival was monitored daily and Kaplan-Meier survival curves were generated using GraphPad Prism 6.05 (GraphPad Software, San Diego, Calif.).

Ewing's sarcoma TC-71 cells were obtained from the Leibniz-Institute DSMZ GmbH (Braunschweig, Germany) and cultured as recommended. TC-71 cells (0.1×10$^6$) in 0.1 ml of BD Matrigel™ Basement Membrane Matrix (Becton Dickinson Bioscience) were injected subcutaneously into the right hind flank of female CB17 SCID mice (5-8 weeks old) on day 0, 5 mice per group. 200 µg mAb (1B7 or 31F9) was injected intraperitoneally on days 1, 4, 8, 11, 14, 21 and 28 post tumor cell injection. Animals in the control group received mock injections with PBS. Mice were monitored for tumor growth twice per week and tumor size was measured by caliper. Tumor volume (mm$^3$) was calculated as length*width*width*0.5.

All procedures were performed under a protocol approved by the Memorial Sloan Kettering Cancer Center Institutional Animal Care and Use Committee.

Immunoglobin cDNA cloning and recombinant antibody expression: Variable region of human mAb heavy and light chain cDNA was recovered by RT-PCR from the individual hybridoma or LCL cell line and subcloned into IgG1 or IgM heavy chain, or IgK or IgL light chain expression vector as described before. Sawada-Hirai, R., et al. *Human anti-anthrax protective antigen neutralizing monoclonal antibodies derived from donors vaccinated with anthrax vaccine adsorbed.* J IMMUNE BASED THER VACCINES 2(1): 5 (2004). Ig heavy chain or light chain expression vector were double digested with Not I and Sal I, and then both fragments were ligated to form a dual gene expression vector. CHO cells in 6 well-plate were transfected with the dual gene expression vector using Lipofectamine 2000 (cat #11668019, Life Technologies, Carlsbad, Calif.). After 24 hrs, transfected cells were transferred to 10 cm dish with selection medium [DMEM supplemented with 10% dialyzed FBS (cat #26400044, Life Technologies, Carlsbad, Calif.), 50 µM L-methionine sulphoximine (MSX, cat #M5379, Sigma, St Louis, Mo.), GS supplement (cat #58762C, Sigma, St Louis, Mo.) and penicillin/streptomycin (cat #PS-20, Omega Scientific, Tarzana, Calif.)]. Two weeks later MSX resistant transfectants were isolated and expanded. High anti-GD2 antibody producing clones were selected by measuring the antibody levels in supernatants in a GD2 specific ELISA assay and expanded for large scale mAb productions.

Results

Generation of recombinant antibodies: The heavy and light chain variable regions from 11 selected antibodies were recovered by RT-PCR and cloned into full-length IgG or IgM heavy chain, or IgK or IgL light chain expression vectors. Molecular sequence analysis using IMGT/V-Quest (Brochet et al., *Nucleic Acids Res.*, 36:W503-8 (2008)) revealed that the nine selected human anti-GD2 antibodies were derived from three different VH families and all used kappa light chains. These IgG antibodies showed different CDR sequences with 5, 7, 8, 9, 10, or 20 mutations deviating from the germ line, respectively (FIGS. 1-14, 17-21; Table 3). The IgM antibody (2E12) also utilizes the kappa light chain and has 3 heavy chain mutations (FIGS. 15-16; Table 3). Recombinant antibodies were produced in CHO cell lines in a wave bioreactor system and purified using protein A or hydroxyapatite chromatography for IgG and IgM, respectively. The purified recombinant antibodies retained the properties of the original hybridoma-derived antibodies with respect to ELISA binding and specificity.

TABLE 3 cDNA Classification of selected human anti-GD2 antibodies

| | VH | | | | | VL | | | |
|---|---|---|---|---|---|---|---|---|---|
| Clone ID | VH | Mutations from germline | DH (RF) | CDR length | JH | VL | Mutations from germline | CDR length | JL |
| 1B7 | 1-3*01 | 10 | 2-21*02 (3) | 8, 8, 13 | 4*02 | K2-28*01 | 5 | 11, 3, 9 | JK3*01 |
| 2H12 | 1-3*01 | 7 | 2-21*02 (3) | 8, 8, 13 | 4*02 | K2-28*01 | 0 | 11, 3, 9 | JK3*01 |
| 1G2 | 1-46*01 | 9 | 2-15*01 (3) | 8, 8, 12 | 4*02 | K4-1*01 | 6 | 12, 3, 9 | JK1*01 |
| 1E9 | 1-46*01 | 9 | 3-9*01 (2) | 8, 8, 12 | 4*02 | K4-1*01 | 3 | 12, 3, 9 | JK2*01 |
| 1H3 | 1-46*01 | 10 | 2-21*-01 (3) | 8, 8, 12 | 4*02 | K4-1*01 | 0 | 12, 3, 9 | JK1*01 |
| 2F5 | 1-46*01 | 7 | 2-15*01 (3) | 8, 8, 12 | 4*02 | K4-1*01 | 1 | 12, 3, 9 | JK1*01 |
| 2F7 | 1-3*01 | 20 | 3-3*01 (2) | 8, 8, 13 | 3*02 | K2-28*01 | 4 | 11, 3, 9 | JK1*01 |
| 2E12 | 1-3*01 | 3 | 2-15*01 (3) | 8, 8, 13 | 4*02 | K2-28*01 | 4 | 11, 3, 9 | JK2*01 |
| 31F9 | 1-8*01 | 5 | 4-23*01 (1) | 8, 8, 14 | 3*02 | K1-27*01 | 5 | 6, 3, 9 | JK1*01 |
| 32E2 | 1-46*03 | 8 | 5-24*01 (1) | 8, 8, 12 | 4*02 | K4-1*01 | 1 | 12, 3, 9 | JK2*02 |

Binding Specificity: In the antigen-specific ELISA assays, seven human anti-GD2 antibodies (1B7, 2H12, 1G2, 2F7, 2E12, 31F9, and 32E2) showed strong reactivity against GD2-PAA conjugate, but not against GD3-PAA, Globo-H, MUC1, Tn-PAA, sTn-PAA, TF-PAA, or SleA-PAA. Three antibodies (1B7, 2H12 and 2F7) also showed cross-activity to GM2-PAA conjugates. Similarly, the seven antibodies also demonstrated strong reactivity with GD2-ceramide conjugate (GD2-cer), but not GD3-ceramide conjugate (GD3-cer), F-GM1-ceramide conjugate (F-GM1-cer), or GM3-ceramide conjugate (GM3-cer).

TABLE 4

Binding of anti-GD2 Antibodies Measured by ELISA

| Clone ID | PBS | GM2-PAA | GD2-PAA | GD3-PAA | Globo-H | MUC1 | Tn-PAA | sTn-PAA | TF-PAA | sLeA-PAA |
|---|---|---|---|---|---|---|---|---|---|---|
| 1B7 | 0.08 | 2.54 | 3.21 | 0.08 | 0.08 | 0.08 | 0.08 | 0.08 | 0.08 | 0.08 |
| 2H12 | 0.08 | 2.37 | 2.98 | 0.08 | 0.08 | 0.08 | 0.08 | 0.08 | 0.08 | 0.08 |
| 1G2 | 0.09 | 0.09 | 2.77 | 0.10 | 0.09 | 0.09 | 0.09 | 0.09 | 0.09 | 0.09 |
| 2F7 | 0.10 | 1.03 | 2.89 | 0.13 | 0.12 | 0.11 | 0.10 | 0.10 | 0.10 | 0.10 |
| 2E12* | 0.12 | 0.38 | 2.94 | 0.09 | 0.08 | 0.09 | 0.09 | 0.09 | 0.09 | 0.39 |
| 31F9 | 0.08 | 0.09 | 1.36 | 0.08 | 0.08 | 0.08 | 0.08 | 0.14 | 0.08 | 0.19 |
| 32E2 | 0.09 | 0.11 | 2.80 | 0.25 | 0.10 | 0.11 | 0.14 | 0.21 | 0.11 | 0.11 |

| Clone ID | EtOH | GM2-cer | GD2-cer | GD3-cer | F-GM1-cer | GM3-cer |
|---|---|---|---|---|---|---|
| 1B7 | 0.08 | 0.82 | 2.14 | 0.08 | 0.08 | 0.07 |
| 2H12 | 0.08 | 0.23 | 1.86 | 0.08 | 0.09 | 0.08 |
| 1G2 | 0.09 | 0.10 | 1.45 | 0.08 | 0.08 | 0.08 |
| 2F7 | 0.09 | 0.12 | 2.27 | 0.09 | 0.08 | 0.08 |
| 2E12* | 0.08 | 0.17 | 2.06 | 0.10 | 0.08 | 0.08 |
| 31F9 | 0.09 | 0.09 | 1.19 | 0.09 | 0.10 | 0.16 |
| 32E2 | 0.09 | 0.09 | 0.62 | 0.11 | 0.09 | 0.09 |

Binding Specificity by ELISA at 2 ug/ml;
*IgM

Analysis of tumor cell binding: Cell surface binding is crucial for cytotoxic activity and was therefore tested next for anti-GD2 antibodies 1B7, 2H12, 1G2, 2F7, 2E12, 31F9, and 32E2. Flow cytometry showed strong binding of all seven antibodies to H524, a small cell cancer cell line, to Lan1-Luc, a neuroblastoma cell line, to Hs527T, a breast cancer cell line, and to TC71 and SaOS2, two sarcoma cell lines. Positive binding was also detected between some of the seven antibodies and other cancer cell lines, including pancreatic cancer cells, acute T cell leukemia cells, melanoma cells, and other sarcoma cells. (Table 5).

TABLE 5

Binding of anti-GD2-mAbs to Different Cell Lines

| | Pancreatic Cancer | | | | | | SCLC | | | | | |
|---|---|---|---|---|---|---|---|---|---|---|---|---|
| | BxPC3 (5 ug/ml) | | | Capan-2 (5 ug/ml) | | | DMS 79 (5 ug/ml) | | | H524 (5 ug/ml) | | |
| Clone ID | Geo-MFI | MFI | % Positive | Geo-MFI | MFI | % Positive | Geo-MFI | MFI | % Positive | Geo-MFI | MFI | % Positive |
| 1B7 | 5.38 | 7.3 | 2.73 | 5.48 | 8.09 | 11.08 | 61.71 | 138.69 | 88.65 | 799.87 | 1304.65 | 99.95 |
| 2H12 | 2.27 | 2.77 | 1.85 | 4.73 | 11.69 | 13.84 | 8.15 | 16.12 | 31.45 | 1919.7 | 2917.48 | 97.78 |
| 1G2 | 2.39 | 3.21 | 0.73 | 3.8 | 5.33 | 2.65 | 5.12 | 9.79 | 14.66 | 147.49 | 228.29 | 99.48 |
| 2F7 | 2.78 | 3.22 | 1.31 | 3.33 | 3.95 | 1.29 | 4.04 | 6.11 | 5.37 | 526.45 | 731.9 | 100 |
| 2E12* | 3.77 | 4.55 | 10.43 | 18.17 | 24.72 | 77.5 | 15.99 | 18.85 | 72.6 | 456.04 | 983.34 | 99.48 |
| 31F9 | 9.94 | 34.43 | 67.52 | 9.8 | 32.38 | 37.51 | 35.06 | 101.5 | 70.71 | 2249.34 | 3321.89 | 97.05 |
| 32E2 | 2.26 | 13.65 | 62.87 | 19.94 | 26.96 | 82.87 | 8.92 | 17.16 | 35.13 | 89.53 | 134.1 | 98.12 |

| | Neuroblastoma | | | Acute T Cell Leukemia | | | Melanoma | | | | | |
|---|---|---|---|---|---|---|---|---|---|---|---|---|
| | Lan1-Luc (5 ug/ml) | | | Jurkat (5 ug/ml) | | | SK-MEL 28 (5 ug/ml) | | | SK-MEL19 (5 ug/ml) | | |
| Clone ID | Geo-MFI | MFI | % Positive | Geo-MFI | MFI | % Positive | Geo-MFI | MFI | % Positive | Geo-MFI | MFI | % Positive |
| 1B7 | 634.22 | 782.54 | 100 | 20.43 | 68.4 | 64.46 | 3.35 | 3.58 | 1.32 | 3.32 | 5.3 | 8.47 |
| 2H12 | 1181.18 | 1776.73 | 100 | 15.17 | 72.83 | 55.62 | 2.79 | 3.4 | 1.45 | 4.68 | 7.18 | 4.52 |
| 1G2 | 109.5 | 187.99 | 94.82 | 3.64 | 6.89 | 6.84 | 3.05 | 3.5 | 1.71 | 3.81 | 4.33 | 0.92 |
| 2F7 | 365.29 | 612.53 | 99.65 | 3.68 | 8.1 | 8.13 | 2.76 | 2.95 | 0.36 | 4 | 4.7 | 1.49 |
| 2E12* | 122.66 | 307.13 | 94.71 | 3.9 | 8.65 | 8.71 | 2.73 | 2.9 | 0.21 | 4.58 | 5.09 | 2.02 |
| 31F9 | 379.28 | 751.54 | 99.63 | 8.74 | 30.53 | 38.13 | 65.83 | 85.92 | 98.64 | 290.52 | 329.63 | 100 |
| 32E2 | 55.99 | 105.08 | 86.16 | 5.16 | 12.46 | 18.76 | 3.71 | 4.8 | 6.94 | 8.99 | 13.51 | 35.7 |

| | Breast Cancer | | | | | | | | | Colorectal Cancer | | |
|---|---|---|---|---|---|---|---|---|---|---|---|---|
| | MCF 7 (5 ug/ml) | | | MDA-MB-231 (5 ug/ml) | | | Hs527T (5 ug/ml) | | | HT29 (5 ug/ml) | | |
| Clone ID | Geo-MFI | MFI | % Positive | Geo-MFI | MFI | % Positive | Geo-MFI | MFI | % Positive | Geo-MFI | MFI | % Positive |
| 1B7 | 93.48 | 196.08 | 91.25 | 76.41 | 771.46 | 67.24 | 125.64 | 653.11 | 90.57 | 4.36 | 6.85 | 2.9 |
| 2H12 | 3.26 | 8.23 | 4.68 | 94.58 | 777.5 | 73.38 | 74.66 | 241.04 | 90.74 | 4.67 | 6.52 | 1.15 |
| 1G2 | 2.84 | 3.46 | 1.02 | 3.9 | 4.59 | 0.74 | 6.66 | 13.47 | 13.87 | 4.47 | 5.9 | 1.66 |
| 2F7 | 2.94 | 3.51 | 1.01 | 9.03 | 45.09 | 17.61 | 14.47 | 92.7 | 33.71 | 4.67 | 5.83 | 1.79 |
| 2E12* | 6.85 | 7.77 | 3.69 | 4.19 | 4.97 | 0.93 | 14.97 | 56.47 | 52.2 | 8.08 | 13.45 | 7.55 |
| 31F9 | 4.36 | 5.2 | 6.15 | 109.38 | 178.36 | 90.7 | 110.26 | 323.89 | 97.13 | 4.15 | 5.33 | 1.47 |
| 32E2 | 3.77 | 5.75 | 7.5 | 6.02 | 7.75 | 3.99 | 9.71 | 27.47 | 27.28 | 5.29 | 13.27 | 5.52 |

| | Sarcoma | | | | | | | | | | | |
|---|---|---|---|---|---|---|---|---|---|---|---|---|
| | ST88 (5 ug/ml) | | | LS141 (5 ug/ml) | | | TC71 (5 ug/ml) | | | SaOS2 (5 ug/ml) | | |
| Clone ID | Geo-MFI | MFI | % Positive | Geo-MFI | MFI | % Positive | Geo-MFI | MFI | % Positive | Geo-MFI | MFI | % Positive |
| 1B7 | 39.34 | 89.69 | 87.51 | 14.32 | 31.67 | 69.65 | 1181.21 | 1869.11 | 99.53 | 890.37 | 1159.57 | 99.74 |
| 2H12 | 34.81 | 69.31 | 91.8 | 23.92 | 37.31 | 90.78 | 430.61 | 820.56 | 100 | 731.18 | 979.77 | 99.89 |
| 1G2 | 3.49 | 4.11 | 2.25 | 3.4 | 3.67 | 0.75 | 44.57 | 82.12 | 95.39 | 56.16 | 86.28 | 96.04 |
| 2F7 | 4.04 | 6.4 | 5.74 | 3.68 | 4.32 | 2.22 | 193.66 | 377.28 | 99.44 | 199.6 | 317.14 | 99.63 |
| 2E12* | 4 | 9.89 | 5.15 | 3.35 | 3.69 | 1.68 | 77.76 | 209.89 | 85.59 | 368.29 | 664.34 | 98.98 |
| 31F9 | 165.38 | 402.28 | 98.14 | 54.87 | 93.62 | 94.89 | 128.94 | 298.18 | 94.99 | 897.48 | 1270.06 | 100 |
| 32E2 | 5.03 | 7.13 | 11.19 | 5.17 | 6.03 | 11.1 | 40.95 | 68.1 | 94.87 | 124.88 | 162.96 | 99.58 |

*IgM, 2 ug/ml

Affinity measurements: The relative affinity/avidity of the binding to GD2 was probed by SPR using a streptavidin-coated biosensor chip to capture biotinylated GD2-PAA (Table 6).

TABLE 6

Kinetic Parameters for anti-GD2 mAbs

| mAb | KA (1/M) | KD (M) | ka (1/Ms) | kd (1/s) | Species | Isotype |
|---|---|---|---|---|---|---|
| 1B7 | $1.4 \times 10^9$ | $7.0 \times 10^{-10}$ | $1.5 \times 10^6$ | $1.0 \times 10^{-3}$ | Human | IgG1/κ |
| 2H12 | $3.7 \times 10^8$ | $2.7 \times 10^{-9}$ | $6.8 \times 10^5$ | $1.8 \times 10^{-3}$ | Human | IgG1/κ |
| 31F9 | $2.0 \times 10^8$ | $5.0 \times 10^{-9}$ | $1.6 \times 10^5$ | $7.7 \times 10^{-4}$ | Human | IgG1/κ |
| 31F9V2 | $3.5 \times 10^8$ | $2.9 \times 10^{-9}$ | $4.0 \times 10^5$ | $1.1 \times 10^{-3}$ | Human | IgG1/κ |
| 32E2 | $1.1 \times 10^8$ | $9.3 \times 10^{-9}$ | $5.0 \times 10^4$ | $4.7 \times 10^{-4}$ | Human | IgG1/κ |

TABLE 6-continued

Kinetic Parameters for anti-GD2 mAbs

| mAb | KA (1/M) | KD (M) | ka (1/Ms) | kd (1/s) | Species | Isotype |
|---|---|---|---|---|---|---|
| 1G2 | $4.0 \times 10^8$ | $2.5 \times 10^{-9}$ | $4.5 \times 10^5$ | $1.1 \times 10^{-3}$ | Human | IgG1/κ |
| 2F7 | $7.0 \times 10^8$ | $1.4 \times 10^{-9}$ | $1.1 \times 10^6$ | $1.5 \times 10^{-3}$ | Human | IgG1/κ |
| 2E12 | $9.0 \times 10^9$ | $1.1 \times 10^{-10}$ | $8.9 \times 10^5$ | $9.9 \times 10^{-5}$ | Human | IgM/κ |

CDC activity: To evaluate the functional activity of 1B7, 2H12, 1G2, 2F7, 2E12, 31F9, 31F9V2, and 32E2, we tested their cytotoxic activity with four different cells (H524, Lan1-Luc, Jurkat, and TC-71) in the presence of human serum as a source of complement. 1B7 showed close to 100% killing activity at 10 μg/mL in three of the four cells tested. 2H12, 2F7, 31F9V2, and 32E2 all showed significant levels of CDC activity toward some cell lines. 2E12, an IgM antibody, showed close to 100% killing activity at 5 μg/mL to H524, Lan1-Luc and TC-71, which was expected because IgM antibodies were known to be more effective in complement-mediated cytotoxicity assays.

TABLE 7

Complement Dependent Cytotoxicity

| | Cytotoxicity (%) | | | |
|---|---|---|---|---|
| Clone ID | H524 | Lan1-luc | Jurkat | TC-71 |
| 1B7 | 98.09 | 106.23 | 69.77 | 94.54 |
| 2H12 | 54.73 | 103.76 | 38.38 | NT |
| 1G2 | −21.44 | −4.97 | NT | 6.23 |
| 2F7 | −1.07 | 79.63 | 63.56 | 20.57 |
| 2E12* | 125.04 | 103.28 | NT | 91.29 |
| 31F9 | 10.47 | −2.09 | −10.28 | 2.91 |
| 31F9V2 | 72.89 | 28.9 | −3.51 | 45.33 |
| 32E2 | −18.43 | −8.1 | 22.48 | −25.7 |

Final concentration: IgGs at 10 ug/ml, IgM at 5 ug/ml; *IgM

Antibody-dependent cell-mediated cytotoxicity: While 2E12 was more potent in the CDC assay, IgG antibodies were known to have antibody-dependent cell-mediated cytotoxicity (ADCC) activity, which is important for tumor killing in vivo. Six anti-GD2 IgG antibodies (1B7, 31F9, 31F9V2, 1G2, 2F7, and 32E2) were tested with five different cell lines (SaOS2, H524, Hs578T, TC71). Treatment with medium only was used as control. High levels of cytotoxicity were measured using 1B7, 31F9, 31F9V2 and 2F7 antibodies, especially with TC71 cell line (FIG. 24). 1G2 and 32E2 also showed some, albeit relatively low level activity.

Figure 25:
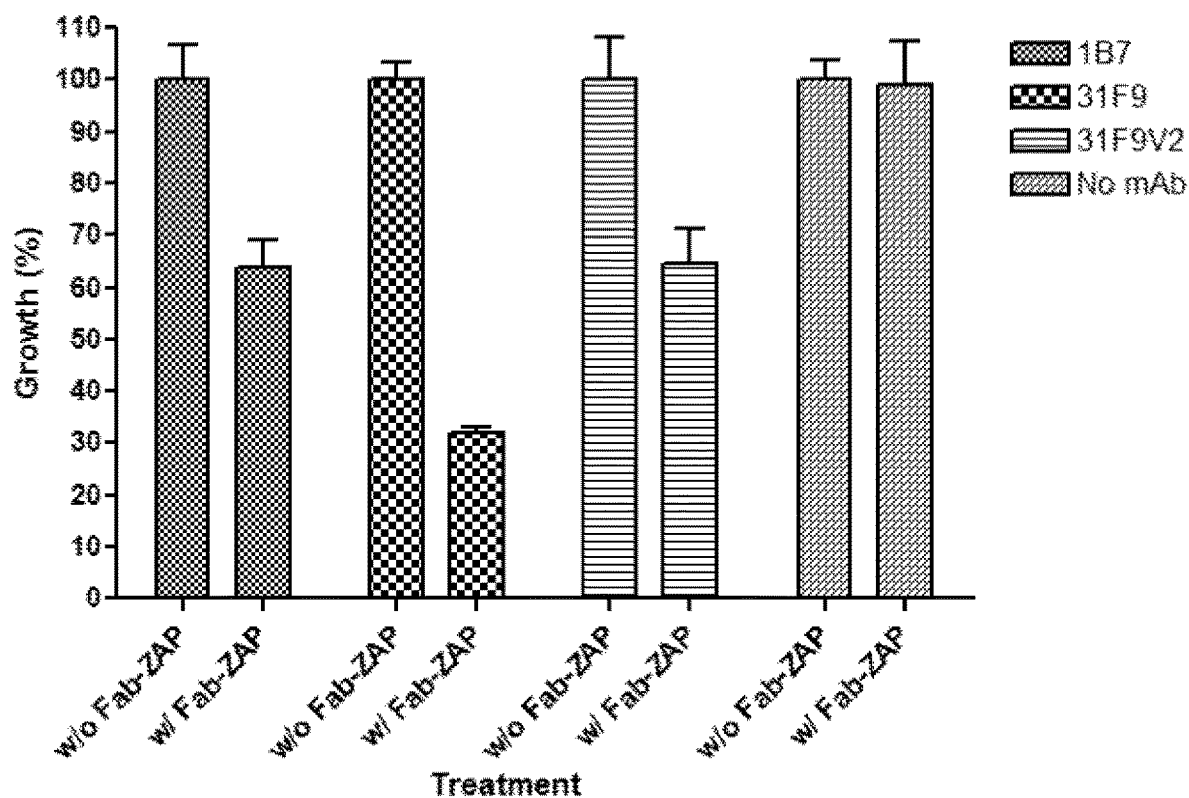
FIG. 25 shows internalization of human anti-GD2 monoclonal antibodies into H524 cells. H524 cells were grown in the presence of 1B7, 31F9, or 31F9V2 complexed with Hum-ZAP, a saporin-conjugated anti-human IgG. The values were measured and normalized to 100% growth in absence of Fab-ZAP.
Figure 26:
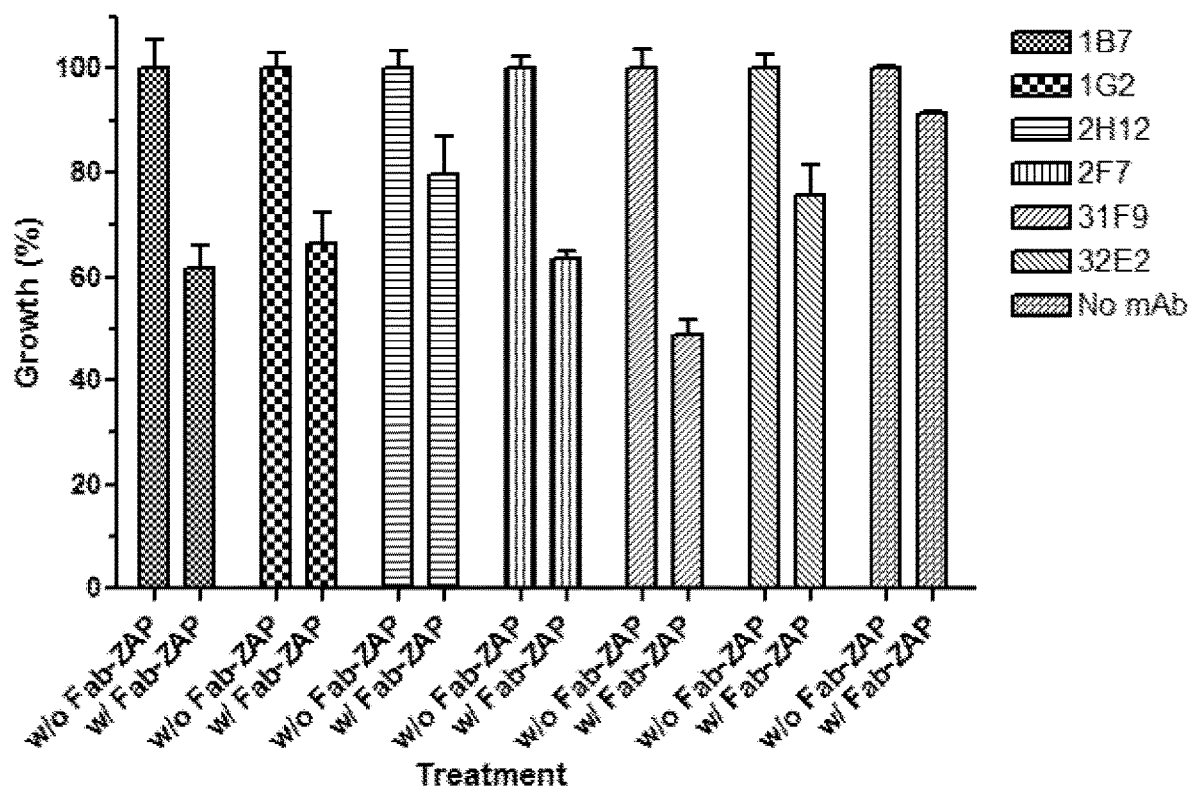
FIG. 26 shows internalization of human anti-GD2 monoclonal antibodies into Lan1-luc cells. Lan1-luc cells were grown in the presence of 1B7, 1G2, 2H12, 2F7, 31F9 or 32E2 complexed with Hum-ZAP, a saporin-conjugated anti-human IgG. The values were measured and normalized to 100% growth in absence of Fab-ZAP.

Internalization assay: Internalization of anti-GD2 antibodies were evaluated by measuring the cytotoxic activity of mAb and Hum-ZAP secondary conjugate complex against GD2 expressing cell lines, H524 and Lan1-luc. Cells that internalize the complex die, while noninternalized saporin leaves the cells unharmed. Treatment with medium only was used as control. As shown in FIG. 25, H524 cells were effectively killed in the presence of 1B7, 31F9, or 31F9V2. Similarly, the Lan1-Luc cells were effectively killed in the presence of 1B7, 1G2, 2H12, 2F7, 31F9, and 32E2 (FIG. 26).

Figure 27:
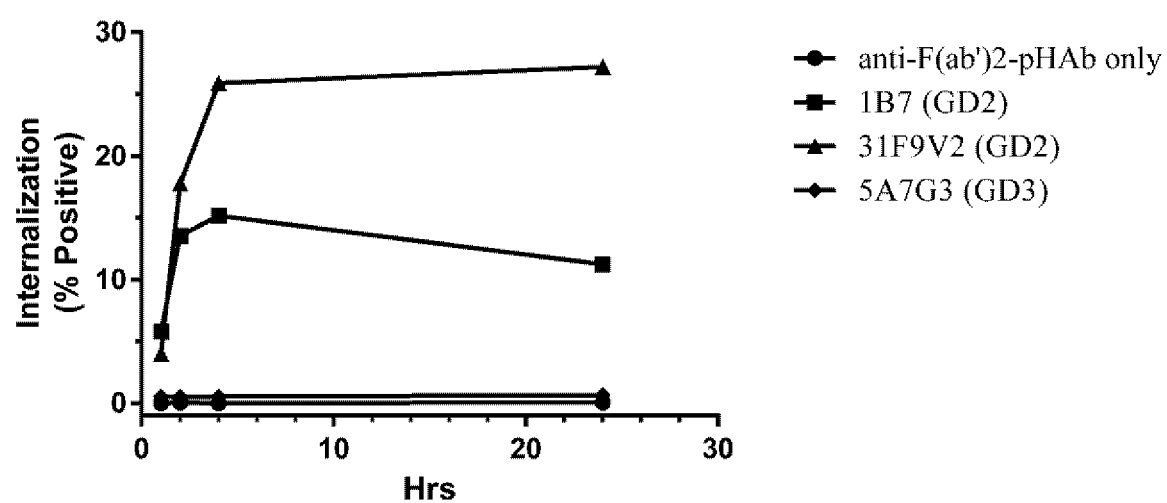
FIG. 27 shows the kinetics of internalization of anti-ganglioside antibodies into H524 (SCLC) tumor cells measured with a pH sensitive reporter by flow cytometry. Cells that internalized the antibodies into the low pH environment of endosomes display a fluorescence measured by flow cytometry.
Figure 28:
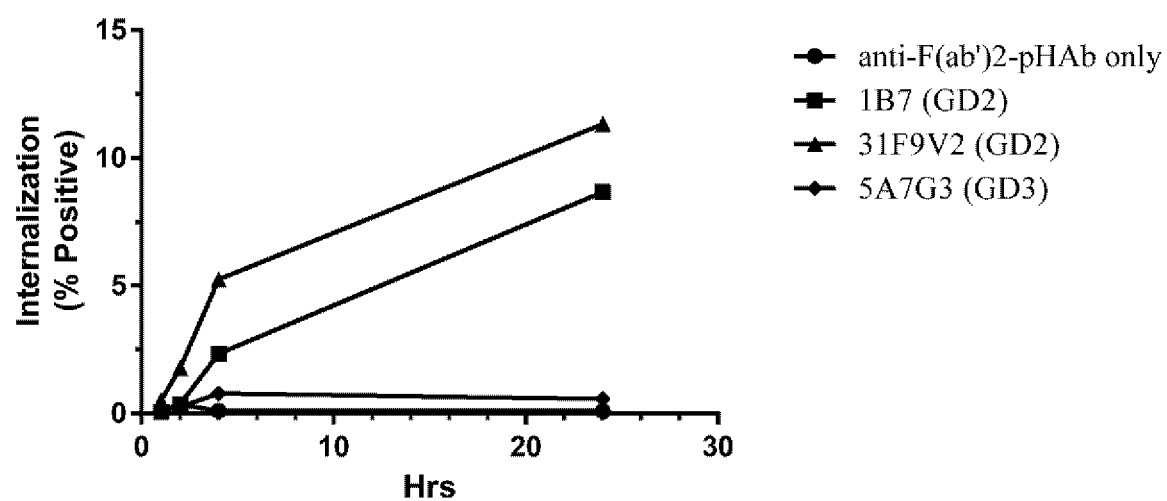
FIG. 28 shows the kinetics of internalization of anti-ganglioside antibodies into TC-71 (sarcoma) tumor cells measured with a pH sensitive reporter by flow cytometry. Cells that internalized the antibodies into the low pH environment of endosomes display a fluorescence measured by flow cytometry.

Further Internalization Assays were performed using a pH sensitive intracellular fluorescent probe, which directly measured the kinetics of internalization via a PH-sensitive fluorescent tag. FIGS. 27 and 28 demonstrate the kinetics of internatilization of 1B7 and 31F9V2 into H524 (SCLC) cells and TC-71 (Sarcoma) cells. As shown, a significant amount of anti-GD2 antibodies were internalized to both H524 (SCLC) tumor cells and TC-71 (sarcoma) tumor cells, as compared to 5A7G3 (anti-GD3) and the anti-F(ab')2-pHAb only.

Figure 29:
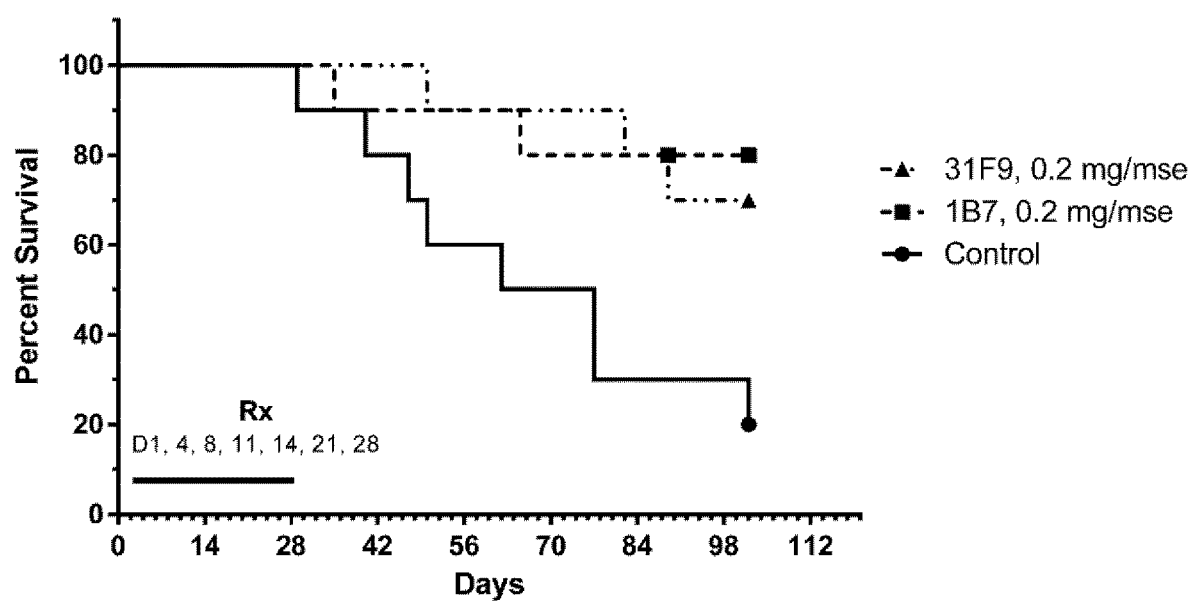
FIG. 29 shows the survival of SCID mice engrafted with human SaOS2 (osteosarcoma) xenograft and treated with anti-GD2 antibodies or control.
Figure 30:
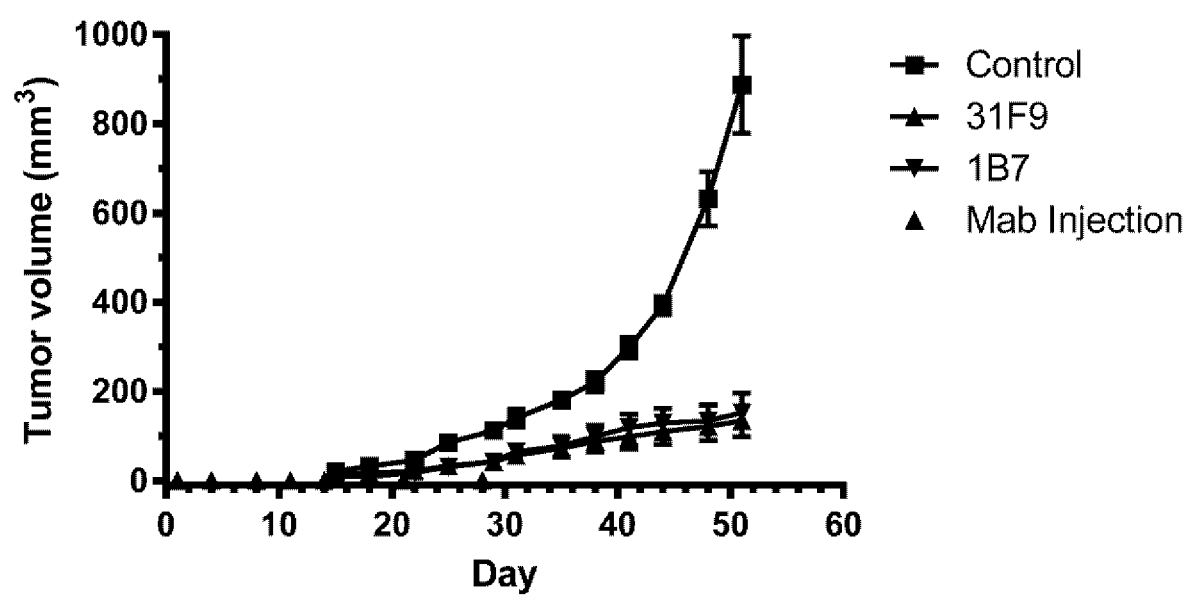
FIG. 30 shows the growth of human TC-71 (sarcoma) xenograft tumors in SCID mice and treated with anti-GD2 antibodies or control.

In vivo Models: The antitumor effects of anti-GD2 antibodies were also evaluated in in vivo models. FIG. 29 shows the results of a survival model, wherein the survival of SCID mice engrafted with human SaOS2 (osteosarcoma) xenograft was measured. As demonstrated in FIG. 29, the percent survival of engrafted mice was significantly increased by the treatment by either 31F9 or 1B7 compared to that in the control group, wherein the mice were injected with PBS only. FIG. 30 shows the results of a subcutaneous tumor model, wherein the growth of human TC-71 (sarcoma) xenograft tumors in SCID mice was measured. As demonstrated in FIG. 30, the tumor volume in the engrafted mice was significantly reduced by the treatment by either 31F9 or 1B7 compared to that in the control group, where the mice were injected with PBS only.

Accordingly, the above data demonstrate significant potential to suppress or regress established tumors and provide a survival benefit using human anti-GD2 mAb treatment.

Throughout this application various publications have been referenced. The disclosures of these publications in their entireties are hereby incorporated by reference in this application in order to more fully describe the state of the art to which this invention pertains. Although the invention has been described with reference to the examples provided above, it should be understood that various modifications can be made without departing from the spirit of the invention.

The invention claimed is:

1. An isolated antibody or antigen binding fragment thereof that binds to GD2, said antibody or antigen binding fragment thereof comprising a variable heavy chain (VH) domain and a variable light chain (VL) domain;
  wherein said VH domain has VH CDR1, VH CDR2, and VH CDR3 amino acid sequences that comprise residues 26-33, residues 51-58, and residues 97-109 of SEQ ID NO: 30, respectively; and
  wherein said VL domain has VL CDR1, VL CDR2, and VL CDR3 amino acid sequences that comprise residues 27-37, residues 55-57, and residues 94-102 of SEQ ID NO: 32, respectively.

2. An isolated antibody or antigen binding fragment thereof that binds to GD2, said antibody or antigen binding fragment thereof comprising a variable heavy chain (VH) domain and a variable light chain (VL) domain, wherein said VH domain has the amino acid sequence of SEQ ID NO: 30; and said VL domain has the amino acid sequence of SEQ ID NO: 32.

3. The isolated antibody or antigen binding fragment thereof of claim 1, wherein said antibody is a human antibody.

4. The isolated antibody or antigen binding fragment thereof of claim 1, wherein said antibody or antigen binding fragment is selected from the group consisting of a Fab, a Fab', a F(ab')2, a scFV, a diabody, a triabody, and a minibody.

5. The isolated antibody or antigen binding fragment thereof of claim 1, wherein said antibody is a monoclonal antibody.

6. The isolated antibody or antigen binding fragment thereof of claim 1, wherein said antibody is an IgG or IgM isotype.

7. The isolated antibody or antigen binding fragment thereof of claim 6, wherein said IgG antibody is an IgG1 subclass.

8. A conjugate comprising an isolated antibody or antigen binding fragment thereof of claim 1 conjugated or recombinantly fused to a diagnostic agent, detectable agent or therapeutic agent.

9. The conjugate of claim 8, wherein said antibody or antigen binding fragment thereof is conjugated or recombinantly fused to a detectable agent.

10. A pharmaceutical composition comprising the antibody or antigen binding fragment thereof of claim 1 and a pharmaceutically acceptable carrier.

* * * * *

SEQUENCE LISTING

<160> NUMBER OF SEQ ID NOS: 44

<210> SEQ ID NO 1
<211> LENGTH: 360
<212> TYPE: DNA
<213> ORGANISM: Artificial Sequence
<220> FEATURE:
<223> OTHER INFORMATION: Description of Artificial Sequence: Synthetic polynucleotide

```
<220> FEATURE:
<221> NAME/KEY: CDS
<222> LOCATION: (1)..(360)

<400> SEQUENCE: 1 caa gtg cag ctg gtg gag tct ggg gct gag gtg aag aag cct ggg gcc     48
Gln Val Gln Leu Val Glu Ser Gly Ala Glu Val Lys Lys Pro Gly Ala
1               5                   10                  15 tca gtg aag gtt tcc tgc aag gct tct gga tac acc ttc act agt tat     96
Ser Val Lys Val Ser Cys Lys Ala Ser Gly Tyr Thr Phe Thr Ser Tyr
            20                  25                  30 gct ata cat tgg gtg cgc cag gcc ccc gga caa agg ctt gag tgg atg    144
Ala Ile His Trp Val Arg Gln Ala Pro Gly Gln Arg Leu Glu Trp Met
        35                  40                  45 gga tgg atc aac gct ggg aat ggt tac aga aaa tat tca cag aag ttc    192
Gly Trp Ile Asn Ala Gly Asn Gly Tyr Arg Lys Tyr Ser Gln Lys Phe
    50                  55                  60 cag ggc aga gtc acc gtt acc agg gac aca tcc gcg agc aca gcc tac    240
Gln Gly Arg Val Thr Val Thr Arg Asp Thr Ser Ala Ser Thr Ala Tyr
65                  70                  75                  80 atg gag ctg agt agt ttg aga tct gaa gac acg gct gtg tat tac tgt    288
Met Glu Leu Ser Ser Leu Arg Ser Glu Asp Thr Ala Val Tyr Tyr Cys
                85                  90                  95 gcg aga ttc gaa gga ggg atg gtg act gcc atg gac ttc tgg ggc cag    336
Ala Arg Phe Glu Gly Gly Met Val Thr Ala Met Asp Phe Trp Gly Gln
            100                 105                 110 gga acc ctg gtc acc gtc tcc tca                                    360
Gly Thr Leu Val Thr Val Ser Ser
        115                 120

<210> SEQ ID NO 2
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Gln Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ala Ile His Trp Val Arg Gln Ala Pro Gly Gln Arg Leu Glu Trp Met
        35                  40                  45

Gly Trp Ile Asn Ala Gly Asn Gly Tyr Arg Lys Tyr Ser Gln Lys Phe
    50                  55                  60

Gln Gly Arg Val Thr Val Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Phe Glu Gly Gly Met Val Thr Ala Met Asp Phe Trp Gly Gln
            100                 105                 110

Gly Thr Leu Val Thr Val Ser Ser
        115                 120

<210> SEQ ID NO 3
<211> LENGTH: 336
<212> TYPE: DNA
<213> ORGANISM: Artificial Sequence
<220> FEATURE:
```

<223> OTHER INFORMATION: Description of Artificial Sequence: Synthetic
    polynucleotide
<220> FEATURE:
<221> NAME/KEY: CDS
<222> LOCATION: (1)..(336)

<400> SEQUENCE: 3

```
gat gtt gtg atg acc cag tct cca ctc tcc ctg ccc gtc acc cct gga      48
Asp Val Val Met Thr Gln Ser Pro Leu Ser Leu Pro Val Thr Pro Gly
1               5                   10                  15 gag ccg gcc tcc atc tcc tgc agg tct agt cag agc ctc ctg cat aga      96
Glu Pro Ala Ser Ile Ser Cys Arg Ser Ser Gln Ser Leu Leu His Arg
            20                  25                  30 aat gga tac aac tac ttg gat tgg tac ctg cag aag cca ggg cag tct     144
Asn Gly Tyr Asn Tyr Leu Asp Trp Tyr Leu Gln Lys Pro Gly Gln Ser
        35                  40                  45 cca cag ctc ctg atc tat ttg ggt tct aat cgg gcc tcc ggg gtc cct     192
Pro Gln Leu Leu Ile Tyr Leu Gly Ser Asn Arg Ala Ser Gly Val Pro
    50                  55                  60 gac agg ttc agt ggc agt gga tca ggc aca gat ttt aca ctg aaa atc     240
Asp Arg Phe Ser Gly Ser Gly Ser Gly Thr Asp Phe Thr Leu Lys Ile
65                  70                  75                  80 agc aga gtg gag gct gag gat gtt ggg gtt tat tac tgc atg caa gct     288
Ser Arg Val Glu Ala Glu Asp Val Gly Val Tyr Tyr Cys Met Gln Ala
                85                  90                  95 cta caa act ccc ttc act ttc ggc cct ggg acc aaa gtg gat atc aaa     336
Leu Gln Thr Pro Phe Thr Phe Gly Pro Gly Thr Lys Val Asp Ile Lys
            100                 105                 110
```

<210> SEQ ID NO 4
<211> LENGTH: 112
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 4

```
Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Arg
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Phe Thr Phe Gly Pro Gly Thr Lys Val Asp Ile Lys
            100                 105                 110
```

<210> SEQ ID NO 5
<211> LENGTH: 360
<212> TYPE: DNA
<213> ORGANISM: Artificial Sequence
<220> FEATURE:
<223> OTHER INFORMATION: Description of Artificial Sequence: Synthetic
    polynucleotide
<220> FEATURE:
<221> NAME/KEY: CDS
<222> LOCATION: (1)..(360)

<400> SEQUENCE: 5

```
gag gtg cag ctg ttg gag tct ggg gct gag gtg aag aag cct ggg gcc        48
Glu Val Gln Leu Leu Glu Ser Gly Ala Glu Val Lys Lys Pro Gly Ala
1               5                   10                  15 tca gtg aag gtt tcc tgc aag gct tct gga tac acc ttc act agc tat        96
Ser Val Lys Val Ser Cys Lys Ala Ser Gly Tyr Thr Phe Thr Ser Tyr
            20                  25                  30 gct ata cat tgg gtg cgc cag gcc ccc gga caa agg ctt gag tgg atg       144
Ala Ile His Trp Val Arg Gln Ala Pro Gly Gln Arg Leu Glu Trp Met
        35                  40                  45 gga tgg atc aac gct ggg aat ggt tac aga aaa tat tca cag aaa ttc       192
Gly Trp Ile Asn Ala Gly Asn Gly Tyr Arg Lys Tyr Ser Gln Lys Phe
    50                  55                  60 cag ggc aga gtc acc gtt acc agg gac aca tcc gcg agc aca gcc tac       240
Gln Gly Arg Val Thr Val Thr Arg Asp Thr Ser Ala Ser Thr Ala Tyr
65                  70                  75                  80 atg gag ttg agc agc ctg aga tct gaa gac acg gct gtg tat tac tgt       288
Met Glu Leu Ser Ser Leu Arg Ser Glu Asp Thr Ala Val Tyr Tyr Cys
                85                  90                  95 gcg aga ttc gaa gga ggg atg gtg act gcc atg gac tac tgg ggc cag       336
Ala Arg Phe Glu Gly Gly Met Val Thr Ala Met Asp Tyr Trp Gly Gln
            100                 105                 110 gga acc ctg gtc acc gtc tcc tca                                        360
Gly Thr Leu Val Thr Val Ser Ser
        115                 120
```

<210> SEQ ID NO 6
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

```
Glu Val Gln Leu Leu Glu Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ala Ile His Trp Val Arg Gln Ala Pro Gly Gln Arg Leu Glu Trp Met
        35                  40                  45

Gly Trp Ile Asn Ala Gly Asn Gly Tyr Arg Lys Tyr Ser Gln Lys Phe
    50                  55                  60

Gln Gly Arg Val Thr Val Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Phe Glu Gly Gly Met Val Thr Ala Met Asp Tyr Trp Gly Gln
            100                 105                 110

Gly Thr Leu Val Thr Val Ser Ser
        115                 120
```

<210> SEQ ID NO 7
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:

<221> NAME/KEY: CDS
<222> LOCATION: (1)..(336)

<400> SEQUENCE: 7

```
gac atc cag gtg acc cag tct cca ctc tcc ctg ccc gtc acc cct gga        48
Asp Ile Gln Val Thr Gln Ser Pro Leu Ser Leu Pro Val Thr Pro Gly
1               5                  10                  15 gag ccg gcc tcc atc tcc tgc agg tct agt cag agc ctc ctg cat agt        96
Glu Pro Ala Ser Ile Ser Cys Arg Ser Ser Gln Ser Leu Leu His Ser
            20                  25                  30 aat gga tac aac tat ttg gat tgg tac ctg cag aag cca ggg cag tct       144
Asn Gly Tyr Asn Tyr Leu Asp Trp Tyr Leu Gln Lys Pro Gly Gln Ser
        35                  40                  45 cca cag ctc ctg atc tat ttg ggt tct aat cgg gcc tcc ggg gtc cct       192
Pro Gln Leu Leu Ile Tyr Leu Gly Ser Asn Arg Ala Ser Gly Val Pro
    50                  55                  60 gac agg ttc agt ggc agt gga tca ggc aca gat ttt aca ctg aaa atc       240
Asp Arg Phe Ser Gly Ser Gly Ser Gly Thr Asp Phe Thr Leu Lys Ile
65                  70                  75                  80 agc aga gtg gag gct gag gat gtt ggg gtt tat tac tgc atg caa gct       288
Ser Arg Val Glu Ala Glu Asp Val Gly Val Tyr Tyr Cys Met Gln Ala
                85                  90                  95 cta caa act ccc ttc act ttc ggc cct ggg atc aaa gtg gat atc aaa       336
Leu Gln Thr Pro Phe Thr Phe Gly Pro Gly Ile Lys Val Asp Ile Lys
            100                 105                 110
```

<210> SEQ ID NO 8
<211> LENGTH: 112
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 8

```
Asp Ile Gln Val Thr Gln Ser Pro Leu Ser Leu Pro Val Thr Pro Gly
1               5                  10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Phe Thr Phe Gly Pro Gly Ile Lys Val Asp Ile Lys
            100                 105                 110
```

<210> SEQ ID NO 9
<211> LENGTH: 357
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: CDS
<222> LOCATION: (1)..(357)

<400> SEQUENCE: 9

```
caa gtg cag ctg gtg gag tct ggg gct gag gtg aag aag cct ggg gcc      48
Gln Val Gln Leu Val Glu Ser Gly Ala Glu Val Lys Lys Pro Gly Ala
1               5                   10                  15 tca gtg aag atg tcc tgc agg gca tct gga tac acc ttc acc agg tac      96
Ser Val Lys Met Ser Cys Arg Ala Ser Gly Tyr Thr Phe Thr Arg Tyr
            20                  25                  30 tat atg cac tgg gtg cga cag gcc cct gga caa ggg ctt gag tgg atg     144
Tyr Met His Trp Val Arg Gln Ala Pro Gly Gln Gly Leu Glu Trp Met
        35                  40                  45 gga ata atc aac cct agt gct ggt agc aca agc tac gca cag aag ttc     192
Gly Ile Ile Asn Pro Ser Ala Gly Ser Thr Ser Tyr Ala Gln Lys Phe
    50                  55                  60 cag gac aga gtc acc atg acc agg gac acg tcc agg agc aca gtc tac     240
Gln Asp Arg Val Thr Met Thr Arg Asp Thr Ser Arg Ser Thr Val Tyr
65                  70                  75                  80 atg gag ctg agc agc ctg aga tct gag gac acg gcc gtg tat tac tgt     288
Met Glu Leu Ser Ser Leu Arg Ser Glu Asp Thr Ala Val Tyr Tyr Cys
                85                  90                  95 gcg aga agg gtg gta gtt ggg ggc ccg ttt gac ttc tgg ggc cag gga     336
Ala Arg Arg Val Val Val Gly Gly Pro Phe Asp Phe Trp Gly Gln Gly
            100                 105                 110 acc ctg gtc acc gtc tcc tca                                         357
Thr Leu Val Thr Val Ser Ser
        115
```

<210> SEQ ID NO 10
<211> LENGTH: 119
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 10

```
Gln Val Gln Leu Val Glu Ser Gly Ala Glu Val Lys Lys Pro Gly Ala
1               5                   10                  15

Ser Val Lys Met Ser Cys Arg Ala Ser Gly Tyr Thr Phe Thr Arg Tyr
            20                  25                  30

Tyr Met His Trp Val Arg Gln Ala Pro Gly Gln Gly Leu Glu Trp Met
        35                  40                  45

Gly Ile Ile Asn Pro Ser Ala Gly Ser Thr Ser Tyr Ala Gln Lys Phe
    50                  55                  60

Gln Asp Arg Val Thr Met Thr Arg Asp Thr Ser Arg Ser Thr Val Tyr
65                  70                  75                  80

Met Glu Leu Ser Ser Leu Arg Ser Glu Asp Thr Ala Val Tyr Tyr Cys
                85                  90                  95

Ala Arg Arg Val Val Val Gly Gly Pro Phe Asp Phe Trp Gly Gln Gly
            100                 105                 110

Thr Leu Val Thr Val Ser Ser
        115
```

<210> SEQ ID NO 11
<211> LENGTH: 339
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: CDS
<222> LOCATION: (1)..(339)

```
<400> SEQUENCE: 11 gac atc cag atg acc cag tct cca gac tcc ctg gct gtg tct ctg ggc      48
Asp Ile Gln Met Thr Gln Ser Pro Asp Ser Leu Ala Val Ser Leu Gly
1               5                   10                  15 gag agg gcc acc atc aac tgc aag tcc agc cag agt gtt tta tac agc      96
Glu Arg Ala Thr Ile Asn Cys Lys Ser Ser Gln Ser Val Leu Tyr Ser
            20                  25                  30 ccc aac aaa aag aac tac tta gct tgg tac cag cag aaa cca gga cag     144
Pro Asn Lys Lys Asn Tyr Leu Ala Trp Tyr Gln Gln Lys Pro Gly Gln
        35                  40                  45 cct cct agt ctg ctc ttt tac tgg gca tct acc cgg gaa tcc ggg gtc     192
Pro Pro Ser Leu Leu Phe Tyr Trp Ala Ser Thr Arg Glu Ser Gly Val
    50                  55                  60 cct gac cga ttc agt ggc agc ggg tct ggg aca gac ttc act ctc acc     240
Pro Asp Arg Phe Ser Gly Ser Gly Ser Gly Thr Asp Phe Thr Leu Thr
65                  70                  75                  80 atc agc agc ctg cag gct gaa gat gtg gca gtt tat tac tgt cag caa     288
Ile Ser Ser Leu Gln Ala Glu Asp Val Ala Val Tyr Tyr Cys Gln Gln
                85                  90                  95 tat tat agt act cct ccg acg ttc ggc caa ggg acc aag gtg gaa atc     336
Tyr Tyr Ser Thr Pro Pro Thr Phe Gly Gln Gly Thr Lys Val Glu Ile
                100                 105                 110 aaa                                                                  339
Lys

<210> SEQ ID NO 12
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Asp Ile Gln Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Pro Asn Lys Lys Asn Tyr Leu Ala Trp Tyr Gln Gln Lys Pro Gly Gln
        35                  40                  45

Pro Pro Ser Leu Leu Phe Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Pro Thr Phe Gly Gln Gly Thr Lys Val Glu Ile
                100                 105                 110

Lys

<210> SEQ ID NO 13
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(357)
```

<400> SEQUENCE: 13

```
cag gtg cag ctg gtg gaa tct ggg gct gag gtg aag aag cct ggg gcc      48
Gln Val Gln Leu Val Glu Ser Gly Ala Glu Val Lys Lys Pro Gly Ala
1               5                   10                  15 tca gtg agg gtt tcc tgc aag gca tct gga tac agg ttc atc agc tac      96
Ser Val Arg Val Ser Cys Lys Ala Ser Gly Tyr Arg Phe Ile Ser Tyr
                20                  25                  30 tat atg cac tgg gtg cga cag gcc cct gga caa ggg ctt gag tgg atg     144
Tyr Met His Trp Val Arg Gln Ala Pro Gly Gln Gly Leu Glu Trp Met
            35                  40                  45 gga ata atc aac cct agt ggt ggt agc aca agc tac gca cag aag ttc     192
Gly Ile Ile Asn Pro Ser Gly Gly Ser Thr Ser Tyr Ala Gln Lys Phe
        50                  55                  60 cag ggc aga gtc acc atg acc agg gac acg tcc acg agc aca atc tac     240
Gln Gly Arg Val Thr Met Thr Arg Asp Thr Ser Thr Ser Thr Ile Tyr
65                  70                  75                  80 atg gag ctg agc agc ctg aga tct gag gac acg gcc gtg tat tac tgt     288
Met Glu Leu Ser Ser Leu Arg Ser Glu Asp Thr Ala Val Tyr Tyr Cys
                85                  90                  95 gcg cgt cgc aat att gtc acg ggt cca ttt gac tat tgg ggc cag gga     336
Ala Arg Arg Asn Ile Val Thr Gly Pro Phe Asp Tyr Trp Gly Gln Gly
                100                 105                 110 acc ctg gtc acc gtc tcc tca                                         357
Thr Leu Val Thr Val Ser Ser
        115
```

<210> SEQ ID NO 14
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

```
Gln Val Gln Leu Val Glu Ser Gly Ala Glu Val Lys Lys Pro Gly Ala
1               5                   10                  15

Ser Val Arg Val Ser Cys Lys Ala Ser Gly Tyr Arg Phe Ile Ser Tyr
                20                  25                  30

Tyr Met His Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe
        50                  55                  60

Gln Gly Arg Val Thr Met Thr Arg Asp Thr Ser Thr Ser Thr Ile Tyr
65                  70                  75                  80

Met Glu Leu Ser Ser Leu Arg Ser Glu Asp Thr Ala Val Tyr Tyr Cys
                85                  90                  95

Ala Arg Arg Asn Ile Val Thr Gly Pro Phe Asp Tyr Trp Gly Gln Gly
                100                 105                 110

Thr Leu Val Thr Val Ser Ser
        115
```

<210> SEQ ID NO 15
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS

<222> LOCATION: (1)..(339)

<400> SEQUENCE: 15

```
gat gtt gtg atg act cag act cca gac tcc ctg gct gtg tct ctg ggc      48
Asp Val Val Met Thr Gln Thr Pro Asp Ser Leu Ala Val Ser Leu Gly
1               5                   10                  15 gag agg gcc acc atc aac tgc aag tcc agc cag agt gtt tta tac atc      96
Glu Arg Ala Thr Ile Asn Cys Lys Ser Ser Gln Ser Val Leu Tyr Ile
            20                  25                  30 tcc aac aat aag aac tac tta gct tgg tac cag cag aaa cca gga cag     144
Ser Asn Asn Lys Asn Tyr Leu Ala Trp Tyr Gln Gln Lys Pro Gly Gln
        35                  40                  45 cct cct aag ctg ctc att tac tgg gca tct acc cgg gaa tcc ggg gtc     192
Pro Pro Lys Leu Leu Ile Tyr Trp Ala Ser Thr Arg Glu Ser Gly Val
    50                  55                  60 cct gac cga ttc agt ggc agc ggg tct ggg aca gat ttc act ctc acc     240
Pro Asp Arg Phe Ser Gly Ser Gly Ser Gly Thr Asp Phe Thr Leu Thr
65                  70                  75                  80 atc agc agc ctg cag gct gag gat gtg gca gtt tat tac tgt cag cac     288
Ile Ser Ser Leu Gln Ala Glu Asp Val Ala Val Tyr Tyr Cys Gln His
                85                  90                  95 tat tat agt act cct ccc act ttt ggc cag ggg acc aag ctg gag atc     336
Tyr Tyr Ser Thr Pro Pro Thr Phe Gly Gln Gly Thr Lys Leu Glu Ile
            100                 105                 110 aaa                                                                  339
Lys
```

<210> SEQ ID NO 16
<211> LENGTH: 113
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 16

```
Asp Val Val Met Thr Gln Thr Pro Asp Ser Leu Ala Val Ser Leu Gly
1               5                   10                  15

Glu Arg Ala Thr Ile Asn Cys Lys Ser Ser Gln Ser Val Leu Tyr Ile
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln His
                85                  90                  95

Tyr Tyr Ser Thr Pro Pro Thr Phe Gly Gln Gly Thr Lys Leu Glu Ile
            100                 105                 110

Lys
```

<210> SEQ ID NO 17
<211> LENGTH: 357
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: CDS

<222> LOCATION: (1)..(357)

<400> SEQUENCE: 17

| | | | | | | | | | | | | | | | | |
|---|---|---|---|---|---|---|---|---|---|---|---|---|---|---|---|---|
| cag | gtg | cag | ctg | gtg | gaa | tct | ggg | gct | gag | gtg | aag | aag | cct | ggg | gcc | 48 |
| Gln | Val | Gln | Leu | Val | Glu | Ser | Gly | Ala | Glu | Val | Lys | Lys | Pro | Gly | Ala | |
| 1 | | | | 5 | | | | | 10 | | | | | 15 | | |
| tca | gtg | aag | gtt | tcc | tgc | aag | gca | tct | gga | tac | acc | ttc | gcc | agg | tac | 96 |
| Ser | Val | Lys | Val | Ser | Cys | Lys | Ala | Ser | Gly | Tyr | Thr | Phe | Ala | Arg | Tyr | |
| | | 20 | | | | | 25 | | | | | 30 | | | | |
| tat | atg | cac | tgg | gtg | cga | cag | gcc | cct | ggc | caa | ggg | cct | gag | tgg | atg | 144 |
| Tyr | Met | His | Trp | Val | Arg | Gln | Ala | Pro | Gly | Gln | Gly | Pro | Glu | Trp | Met | |
| | | 35 | | | | | 40 | | | | | 45 | | | | |
| ggc | ata | atc | aac | cct | agt | ggt | gga | agc | aca | agt | tac | gca | cag | aag | ttc | 192 |
| Gly | Ile | Ile | Asn | Pro | Ser | Gly | Gly | Ser | Thr | Ser | Tyr | Ala | Gln | Lys | Phe | |
| | 50 | | | | | 55 | | | | | 60 | | | | | |
| cag | ggc | aga | gtc | acc | gtg | acc | agg | gac | acg | tcc | acg | agc | aca | gtc | tac | 240 |
| Gln | Gly | Arg | Val | Thr | Val | Thr | Arg | Asp | Thr | Ser | Thr | Ser | Thr | Val | Tyr | |
| 65 | | | | | 70 | | | | | 75 | | | | | 80 | |
| atg | gag | ctg | agc | agc | ctg | aga | tct | gag | gac | acg | gcc | gtg | tat | tac | tgt | 288 |
| Met | Glu | Leu | Ser | Ser | Leu | Arg | Ser | Glu | Asp | Thr | Ala | Val | Tyr | Tyr | Cys | |
| | | | | 85 | | | | | 90 | | | | | 95 | | |
| gcg | agg | agg | gtg | gta | ctt | ggg | ggc | ccg | ttt | gac | tac | tgg | ggc | cag | gga | 336 |
| Ala | Arg | Arg | Val | Val | Leu | Gly | Gly | Pro | Phe | Asp | Tyr | Trp | Gly | Gln | Gly | |
| | | | 100 | | | | | 105 | | | | | 110 | | | |
| acc | ctg | gtc | acc | gtc | tcc | tca | | | | | | | | | | 357 |
| Thr | Leu | Val | Thr | Val | Ser | Ser | | | | | | | | | | |
| | | | 115 | | | | | | | | | | | | | |

<210> SEQ ID NO 18
<211> LENGTH: 119
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 18

Gln Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Ala Arg Tyr
            20                  25                  30

Tyr Met His Trp Val Arg Gln Ala Pro Gly Gln Gly Pro Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Val Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Arg Val Val Leu Gly Gly Pro Phe Asp Tyr Trp Gly Gln Gly
            100                 105                 110

Thr Leu Val Thr Val Ser Ser
        115

<210> SEQ ID NO 19
<211> LENGTH: 339
<212> TYPE: DNA
<213> ORGANISM: Artificial Sequence
<220> FEATURE:
<223> OTHER INFORMATION: Description of Artificial Sequence: Synthetic polynucleotide

```
<220> FEATURE:
<221> NAME/KEY: CDS
<222> LOCATION: (1)..(339)

<400> SEQUENCE: 19 gac atc cgg gtg acc cag tct cca gac tcc ctg gct gtg tct ctg ggc      48
Asp Ile Arg Val Thr Gln Ser Pro Asp Ser Leu Ala Val Ser Leu Gly
1               5                   10                  15 gag agg gcc acc atc aac tgc aag tcc agc cag agt gtt tta tac agc      96
Glu Arg Ala Thr Ile Asn Cys Lys Ser Ser Gln Ser Val Leu Tyr Ser
                20                  25                  30 tcc aac aat aag aac tac tta gct tgg tac cag cag aaa cca gga cag     144
Ser Asn Asn Lys Asn Tyr Leu Ala Trp Tyr Gln Gln Lys Pro Gly Gln
            35                  40                  45 cct cct aag ctg ctc att tac tgg gca tct acc cgg gaa tcc ggg gtc     192
Pro Pro Lys Leu Leu Ile Tyr Trp Ala Ser Thr Arg Glu Ser Gly Val
        50                  55                  60 cct gac cga ttc agt ggc agc ggg tct ggg aca gat ttc act ctc acc     240
Pro Asp Arg Phe Ser Gly Ser Gly Ser Gly Thr Asp Phe Thr Leu Thr
65                  70                  75                  80 atc agc agc ctg cag gct gaa gat gtg gca gtt tat tac tgt cag caa     288
Ile Ser Ser Leu Gln Ala Glu Asp Val Ala Val Tyr Tyr Cys Gln Gln
                85                  90                  95 tat tat agt act cct ccg acg ttc ggc caa ggg acc aag gtg gaa atc     336
Tyr Tyr Ser Thr Pro Pro Thr Phe Gly Gln Gly Thr Lys Val Glu Ile
                100                 105                 110 aaa                                                                  339
Lys

<210> SEQ ID NO 20
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Asp Ile Arg Val Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
                20                  25                  30

Ser Asn Asn Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
        50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Pro Thr Phe Gly Gln Gly Thr Lys Val Glu Ile
                100                 105                 110

Lys

<210> SEQ ID NO 21
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide
```

```
<220> FEATURE:
<221> NAME/KEY: CDS
<222> LOCATION: (1)..(357)

<400> SEQUENCE: 21 gaa gtg cag ctg ttg gag tct ggg gct gag gtg aag aag cct ggg gcc    48
Glu Val Gln Leu Leu Glu Ser Gly Ala Glu Val Lys Lys Pro Gly Ala
1               5                   10                  15 tca gtg aag gtt tcc tgc aag gca tct gga tac acc ttc acc aga tac    96
Ser Val Lys Val Ser Cys Lys Ala Ser Gly Tyr Thr Phe Thr Arg Tyr
            20                  25                  30 tat atg cac tgg gtg cga cag gcc cct gga caa ggg ctt gag tgg atg   144
Tyr Met His Trp Val Arg Gln Ala Pro Gly Gln Gly Leu Glu Trp Met
        35                  40                  45 gga ata atc aac cct agt agt ggt agc aca agc tac gca cag aag ttc   192
Gly Ile Ile Asn Pro Ser Ser Gly Ser Thr Ser Tyr Ala Gln Lys Phe
    50                  55                  60 cag ggc aga gtc acc atg acc agg gac acg tcc acg agc aca gtc tac   240
Gln Gly Arg Val Thr Met Thr Arg Asp Thr Ser Thr Ser Thr Val Tyr
65                  70                  75                  80 atg gag ctg agc agc ctg aga tct gag gac atg gcc gta tat tac tgt   288
Met Glu Leu Ser Ser Leu Arg Ser Glu Asp Met Ala Val Tyr Tyr Cys
                85                  90                  95 gcg agg agg gtg gta gtt ggg ggc ccg ttt gac tac tgg ggc cag gga   336
Ala Arg Arg Val Val Val Gly Gly Pro Phe Asp Tyr Trp Gly Gln Gly
            100                 105                 110 acc ctg gtc acc gtc tcc tca                                       357
Thr Leu Val Thr Val Ser Ser
        115

<210> SEQ ID NO 22
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Glu Val Gln Leu Leu Glu Ser Gly Ala Glu Val Lys Lys Pro Gly Ala
1               5                   10                  15

Ser Val Lys Val Ser Cys Lys Ala Ser Gly Tyr Thr Phe Thr Arg Tyr
            20                  25                  30

Tyr Met His Trp Val Arg Gln Ala Pro Gly Gln Gly Leu Glu Trp Met
        35                  40                  45

Gly Ile Ile Asn Pro Ser Ser Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Met Ala Val Tyr Tyr Cys
                85                  90                  95

Ala Arg Arg Val Val Val Gly Gly Pro Phe Asp Tyr Trp Gly Gln Gly
            100                 105                 110

Thr Leu Val Thr Val Ser Ser
        115

<210> SEQ ID NO 23
<211> LENGTH: 339
<212> TYPE: DNA
<213> ORGANISM: Artificial Sequence
<220> FEATURE:
```

<223> OTHER INFORMATION: Description of Artificial Sequence: Synthetic
      polynucleotide
<220> FEATURE:
<221> NAME/KEY: CDS
<222> LOCATION: (1)..(339)

<400> SEQUENCE: 23

```
gac atc cag ttg acc cag tct cca gac tcc ctg gct gtg tct ctg ggc      48
Asp Ile Gln Leu Thr Gln Ser Pro Asp Ser Leu Ala Val Ser Leu Gly
1               5                  10                  15 gag agg gcc acc atc aac tgc aag tcc agc cag agt att tta tac agc      96
Glu Arg Ala Thr Ile Asn Cys Lys Ser Ser Gln Ser Ile Leu Tyr Ser
            20                  25                  30 tcc aac aat aag aac tac tta gct tgg tac cag cag aaa cca gga cag     144
Ser Asn Asn Lys Asn Tyr Leu Ala Trp Tyr Gln Gln Lys Pro Gly Gln
        35                  40                  45 cct cct aag ctg ctc att tac tgg gca tct acc cgg gaa tcc ggg gtc     192
Pro Pro Lys Leu Leu Ile Tyr Trp Ala Ser Thr Arg Glu Ser Gly Val
    50                  55                  60 cct gac cga ttc agt ggc agc ggg tct ggg aca gat ttc act ctc acc     240
Pro Asp Arg Phe Ser Gly Ser Gly Ser Gly Thr Asp Phe Thr Leu Thr
65                  70                  75                  80 atc agc agc ctg cag gct gaa gat gtg gca gtt tat tac tgt cag caa     288
Ile Ser Ser Leu Gln Ala Glu Asp Val Ala Val Tyr Tyr Cys Gln Gln
                85                  90                  95 tat tat agt act cct ccg acg ttc ggc caa ggg acc aag gtg gaa atc     336
Tyr Tyr Ser Thr Pro Pro Thr Phe Gly Gln Gly Thr Lys Val Glu Ile
            100                 105                 110 aag                                                                  339
Lys
```

<210> SEQ ID NO 24
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

```
Asp Ile Gln Leu Thr Gln Ser Pro Asp Ser Leu Ala Val Ser Leu Gly
1               5                  10                  15

Glu Arg Ala Thr Ile Asn Cys Lys Ser Ser Gln Ser Ile Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Pro Thr Phe Gly Gln Gly Thr Lys Val Glu Ile
            100                 105                 110

Lys
```

<210> SEQ ID NO 25
<211> LENGTH: 360
<212> TYPE: DNA
<213> ORGANISM: Artificial Sequence
<220> FEATURE:

```
<223> OTHER INFORMATION: Description of Artificial Sequence: Synthetic
      polynucleotide
<220> FEATURE:
<221> NAME/KEY: CDS
<222> LOCATION: (1)..(360)

<400> SEQUENCE: 25 gaa gtg cag ctg ttg gag tct ggg gct gag gtg aag aag cct ggg gcc      48
Glu Val Gln Leu Leu Glu Ser Gly Ala Glu Val Lys Lys Pro Gly Ala
1               5                   10                  15 tca gtg aag gtt tcc tgc aag gct tct gga tac atc ttc agt aga tat      96
Ser Val Lys Val Ser Cys Lys Ala Ser Gly Tyr Ile Phe Ser Arg Tyr
            20                  25                  30 gct atc cat tgg gtg cgc cag gcc ccc gga caa ggg ctt gag tgg atg     144
Ala Ile His Trp Val Arg Gln Ala Pro Gly Gln Gly Leu Glu Trp Met
        35                  40                  45 gga tgg atc aac cct ttc aat ggt ttc aca aaa tat tca cag aag ttt     192
Gly Trp Ile Asn Pro Phe Asn Gly Phe Thr Lys Tyr Ser Gln Lys Phe
    50                  55                  60 cag ggc aga gtc gcc ctc act agg gac aga tcc gcg acc aca ggc tac     240
Gln Gly Arg Val Ala Leu Thr Arg Asp Arg Ser Ala Thr Thr Gly Tyr
65                  70                  75                  80 atg gag ttg agc agc ctg aca tct gaa gac acg gct gtg tac tac tgt     288
Met Glu Leu Ser Ser Leu Thr Ser Glu Asp Thr Ala Val Tyr Tyr Cys
                85                  90                  95 gcg agg ctg gaa tct aac aag ttt tat gct ttt gat atc tgg ggc cag     336
Ala Arg Leu Glu Ser Asn Lys Phe Tyr Ala Phe Asp Ile Trp Gly Gln
            100                 105                 110 ggg aca atg gtc acc gtc tct tca                                     360
Gly Thr Met Val Thr Val Ser Ser
        115                 120

<210> SEQ ID NO 26
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Glu Val Gln Leu Leu Glu Ser Gly Ala Glu Val Lys Lys Pro Gly Ala
1               5                   10                  15

Ser Val Lys Val Ser Cys Lys Ala Ser Gly Tyr Ile Phe Ser Arg Tyr
            20                  25                  30

Ala Ile His Trp Val Arg Gln Ala Pro Gly Gln Gly Leu Glu Trp Met
        35                  40                  45

Gly Trp Ile Asn Pro Phe Asn Gly Phe Thr Lys Tyr Ser Gln Lys Phe
    50                  55                  60

Gln Gly Arg Val Ala Leu Thr Arg Asp Arg Ser Ala Thr Thr Gly Tyr
65                  70                  75                  80

Met Glu Leu Ser Ser Leu Thr Ser Glu Asp Thr Ala Val Tyr Tyr Cys
                85                  90                  95

Ala Arg Leu Glu Ser Asn Lys Phe Tyr Ala Phe Asp Ile Trp Gly Gln
            100                 105                 110

Gly Thr Met Val Thr Val Ser Ser
        115                 120

<210> SEQ ID NO 27
<211> LENGTH: 336
<212> TYPE: DNA
```

<213> ORGANISM: Artificial Sequence
<220> FEATURE:
<223> OTHER INFORMATION: Description of Artificial Sequence: Synthetic polynucleotide
<220> FEATURE:
<221> NAME/KEY: CDS
<222> LOCATION: (1)..(336)

<400> SEQUENCE: 27

```
gaa att gta atg aca cag tct cca ctc tcc ctg ccc gtc acc cct gga        48
Glu Ile Val Met Thr Gln Ser Pro Leu Ser Leu Pro Val Thr Pro Gly
1               5                   10                  15 gag ccg gcc tcc atc tcc tgc acg tct agt cag agc ctc ctg cat agt        96
Glu Pro Ala Ser Ile Ser Cys Thr Ser Ser Gln Ser Leu Leu His Ser
                20                  25                  30 aat gga tat aac tat ttg gat tgg tac ttg cag aag cca ggg cag tct       144
Asn Gly Tyr Asn Tyr Leu Asp Trp Tyr Leu Gln Lys Pro Gly Gln Ser
            35                  40                  45 cca cag ctc ctg atc tat ttg ggt tct aat cgg gcc tcc ggg gtc cct       192
Pro Gln Leu Leu Ile Tyr Leu Gly Ser Asn Arg Ala Ser Gly Val Pro
        50                  55                  60 gac agg ttc agt ggc agt gga tca ggc aca gat ttt aca ctg aaa atc       240
Asp Arg Phe Ser Gly Ser Gly Ser Gly Thr Asp Phe Thr Leu Lys Ile
65                  70                  75                  80 agc aca gtg gag gct gag gat gtt ggg gtt tat tac tgc atg caa gct       288
Ser Thr Val Glu Ala Glu Asp Val Gly Val Tyr Tyr Cys Met Gln Ala
                85                  90                  95 cta caa act ccg tgg acg ttt ggc caa ggg acc aag gtg gaa atc aaa       336
Leu Gln Thr Pro Trp Thr Phe Gly Gln Gly Thr Lys Val Glu Ile Lys
                100                 105                 110
```

<210> SEQ ID NO 28
<211> LENGTH: 112
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 28

```
Glu Ile Val Met Thr Gln Ser Pro Leu Ser Leu Pro Val Thr Pro Gly
1               5                   10                  15

Glu Pro Ala Ser Ile Ser Cys Thr Ser Ser Gln Ser Leu Leu His Ser
                20                  25                  30

Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
        50                  55                  60

Asp Arg Phe Ser Gly Ser Gly Ser Gly Thr Asp Phe Thr Leu Lys Ile
65                  70                  75                  80

Ser Thr Val Glu Ala Glu Asp Val Gly Val Tyr Tyr Cys Met Gln Ala
                85                  90                  95

Leu Gln Thr Pro Trp Thr Phe Gly Gln Gly Thr Lys Val Glu Ile Lys
                100                 105                 110
```

<210> SEQ ID NO 29
<211> LENGTH: 360
<212> TYPE: DNA
<213> ORGANISM: Artificial Sequence
<220> FEATURE:
<223> OTHER INFORMATION: Description of Artificial Sequence: Synthetic polynucleotide
<220> FEATURE:

<220> FEATURE:
<221> NAME/KEY: CDS
<222> LOCATION: (1)..(360)

<400> SEQUENCE: 29

```
caa gtg cag ctg ttg gag tct ggg gct gag gtg aag aag cct ggg gcc    48
Gln Val Gln Leu Leu Glu Ser Gly Ala Glu Val Lys Lys Pro Gly Ala
1               5                   10                  15 tca gtg aag gtt tcc tgc aag gct tct gga tac acc ttc act agc tat    96
Ser Val Lys Val Ser Cys Lys Ala Ser Gly Tyr Thr Phe Thr Ser Tyr
            20                  25                  30 gct atg cat tgg gtg cgc cag gcc ccc gga caa agg ctt gag tgg atg   144
Ala Met His Trp Val Arg Gln Ala Pro Gly Gln Arg Leu Glu Trp Met
        35                  40                  45 gga tgg atc aac gct ggc aat ggt aac aca ata tat tca cag aag ttc   192
Gly Trp Ile Asn Ala Gly Asn Gly Asn Thr Ile Tyr Ser Gln Lys Phe
    50                  55                  60 cag gcc aga gtc acc att acc agg gac acg tcc gcg agc aca gcc tac   240
Gln Ala Arg Val Thr Ile Thr Arg Asp Thr Ser Ala Ser Thr Ala Tyr
65                  70                  75                  80 atg gag ctg agc agc ctg aga tct gaa gac acg gct gtg tat tac tgt   288
Met Glu Leu Ser Ser Leu Arg Ser Glu Asp Thr Ala Val Tyr Tyr Cys
                85                  90                  95 gcg aga tgg gta gga ggg gtg gcc tcg tac ttt gac tac tgg ggc cag   336
Ala Arg Trp Val Gly Gly Val Ala Ser Tyr Phe Asp Tyr Trp Gly Gln
            100                 105                 110 ggg acc ctg gtc acc gtc tcc tca                                   360
Gly Thr Leu Val Thr Val Ser Ser
        115                 120
```

<210> SEQ ID NO 30
<211> LENGTH: 120
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 30

```
Gln Val Gln Leu Leu Glu Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ala Met His Trp Val Arg Gln Ala Pro Gly Gln Arg Leu Glu Trp Met
        35                  40                  45

Gly Trp Ile Asn Ala Gly Asn Gly Asn Thr Ile Tyr Ser Gln Lys Phe
    50                  55                  60

Gln Ala Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Val Gly Gly Val Ala Ser Tyr Phe Asp Tyr Trp Gly Gln
            100                 105                 110

Gly Thr Leu Val Thr Val Ser Ser
        115                 120
```

<210> SEQ ID NO 31
<211> LENGTH: 336
<212> TYPE: DNA
<213> ORGANISM: Artificial Sequence
<220> FEATURE:
<223> OTHER INFORMATION: Description of Artificial Sequence: Synthetic

```
                polynucleotide
<220> FEATURE:
<221> NAME/KEY: CDS
<222> LOCATION: (1)..(336)

<400> SEQUENCE: 31 gaa att gta ttg aca cag tct cca ctc tcc ctg tcc gtc acc cct gga      48
Glu Ile Val Leu Thr Gln Ser Pro Leu Ser Leu Ser Val Thr Pro Gly
1               5                  10                  15 gag ccg gcc tcc atc tcc tgc agg tct agt cag agc ctc ctg cat aga      96
Glu Pro Ala Ser Ile Ser Cys Arg Ser Ser Gln Ser Leu Leu His Arg
            20                  25                  30 aat gga tac aat tat ttt gat tgg tac ctg cag cag cca ggg cag tct     144
Asn Gly Tyr Asn Tyr Phe Asp Trp Tyr Leu Gln Gln Pro Gly Gln Ser
        35                  40                  45 cca cag ctc ctg atc tat ttg ggt tct aat cgg gcc tcc ggg gtc cct     192
Pro Gln Leu Leu Ile Tyr Leu Gly Ser Asn Arg Ala Ser Gly Val Pro
    50                  55                  60 gac agg ttc agt ggc agt gga tca ggc aca gat ttt aca ctg aaa atc     240
Asp Arg Phe Ser Gly Ser Gly Ser Gly Thr Asp Phe Thr Leu Lys Ile
65                  70                  75                  80 agc aga gtg gag gct gag gat gtt ggg gtt tat tac tgc atg caa gct     288
Ser Arg Val Glu Ala Glu Asp Val Gly Val Tyr Tyr Cys Met Gln Ala
                85                  90                  95 cta caa act ccg tac act ttt ggc cag ggg acc aag ctg gag atc aaa     336
Leu Gln Thr Pro Tyr Thr Phe Gly Gln Gly Thr Lys Leu Glu Ile Lys
            100                 105                 110

<210> SEQ ID NO 32
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Glu Ile Val Leu Thr Gln Ser Pro Leu Ser Leu Ser Val Thr Pro Gly
1               5                  10                  15

Glu Pro Ala Ser Ile Ser Cys Arg Ser Ser Gln Ser Leu Leu His Arg
            20                  25                  30

Asn Gly Tyr Asn Tyr Phe Asp Trp Tyr Leu Gln Gln Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Tyr Thr Phe Gly Gln Gly Thr Lys Leu Glu Ile Lys
            100                 105                 110

<210> SEQ ID NO 33
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(363)
```

<400> SEQUENCE: 33

```
caa gtg cag ctg ttg gag tct ggg gct gag gtg aag aag cct ggg gcc     48
Gln Val Gln Leu Leu Glu Ser Gly Ala Glu Val Lys Lys Pro Gly Ala
1               5                   10                  15 tca gtg aag gtc tcc tgc gag gct tct gga tac acc ttc acc agt tct     96
Ser Val Lys Val Ser Cys Glu Ala Ser Gly Tyr Thr Phe Thr Ser Ser
            20                  25                  30 gat atc aac tgg gtg cga cag gcc act gga caa ggg ctt gag tgg atg    144
Asp Ile Asn Trp Val Arg Gln Ala Thr Gly Gln Gly Leu Glu Trp Met
        35                  40                  45 gga tgg atg aac cct aat agt ggt aac aca ggc tat gca cag aag ttc    192
Gly Trp Met Asn Pro Asn Ser Gly Asn Thr Gly Tyr Ala Gln Lys Phe
    50                  55                  60 cag ggc aga gtc acc atg acc agg aac acc tcc ata agc aca gcc tac    240
Gln Gly Arg Val Thr Met Thr Arg Asn Thr Ser Ile Ser Thr Ala Tyr
65                  70                  75                  80 atg gag ctg agc agc ctg aga tct gag gac acg gcc gtg tat tac tgt    288
Met Glu Leu Ser Ser Leu Arg Ser Glu Asp Thr Ala Val Tyr Tyr Cys
                85                  90                  95 gcg aga gaa aga ccc cgg agg cgt ggg ggt ggt ttt gat atc tgg ggc    336
Ala Arg Glu Arg Pro Arg Arg Arg Gly Gly Gly Phe Asp Ile Trp Gly
            100                 105                 110 caa ggg aca atg gtc acc gtc tct tca                                363
Gln Gly Thr Met Val Thr Val Ser Ser
        115                 120
```

<210> SEQ ID NO 34
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

```
Gln Val Gln Leu Leu Glu Ser Gly Ala Glu Val Lys Lys Pro Gly Ala
1               5                   10                  15

Ser Val Lys Val Ser Cys Glu Ala Ser Gly Tyr Thr Phe Thr Ser Ser
            20                  25                  30

Asp Ile Asn Trp Val Arg Gln Ala Thr Gly Gln Gly Leu Glu Trp Met
        35                  40                  45

Gly Trp Met Asn Pro Asn Ser Gly Asn Thr Gly Tyr Ala Gln Lys Phe
    50                  55                  60

Gln Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Arg Pro Arg Arg Arg Gly Gly Gly Phe Asp Ile Trp Gly
            100                 105                 110

Gln Gly Thr Met Val Thr Val Ser Ser
        115                 120
```

<210> SEQ ID NO 35
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS

<222> LOCATION: (1)..(363)

<400> SEQUENCE: 35

```
cag gta cag ctg cag cag tct ggg gct gag gtg aag aag cct ggg gcc      48
Gln Val Gln Leu Gln Gln Ser Gly Ala Glu Val Lys Lys Pro Gly Ala
1               5                   10                  15 tca gtg aag gtc tcc tgc gag gct tct gga tac acc ttc acc agt tct      96
Ser Val Lys Val Ser Cys Glu Ala Ser Gly Tyr Thr Phe Thr Ser Ser
            20                  25                  30 gat atc aac tgg gtg cga cag gcc act gga caa ggg ctt gag tgg atg     144
Asp Ile Asn Trp Val Arg Gln Ala Thr Gly Gln Gly Leu Glu Trp Met
        35                  40                  45 gga tgg atg aac cct aaa agt ggt aac aca ggc tat gca cag aag ttc     192
Gly Trp Met Asn Pro Lys Ser Gly Asn Thr Gly Tyr Ala Gln Lys Phe
    50                  55                  60 cag ggc aga gtc acc atg acc agg aac acc tcc ata agc aca gcc tac     240
Gln Gly Arg Val Thr Met Thr Arg Asn Thr Ser Ile Ser Thr Ala Tyr
65                  70                  75                  80 atg gag ctg agc agc ctg aga tct gag gac acg gcc gtg tat tac tgt     288
Met Glu Leu Ser Ser Leu Arg Ser Glu Asp Thr Ala Val Tyr Tyr Cys
                85                  90                  95 gcg aga gaa aga ccc cgg agg cgt ggg ggt ggt ttt gat atc tgg ggc     336
Ala Arg Glu Arg Pro Arg Arg Arg Gly Gly Gly Phe Asp Ile Trp Gly
            100                 105                 110 caa ggg aca atg gtc acc gtc tct tca                                 363
Gln Gly Thr Met Val Thr Val Ser Ser
        115                 120
```

<210> SEQ ID NO 36
<211> LENGTH: 121
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 36

```
Gln Val Gln Leu Gln Gln Ser Gly Ala Glu Val Lys Lys Pro Gly Ala
1               5                   10                  15

Ser Val Lys Val Ser Cys Glu Ala Ser Gly Tyr Thr Phe Thr Ser Ser
            20                  25                  30

Asp Ile Asn Trp Val Arg Gln Ala Thr Gly Gln Gly Leu Glu Trp Met
        35                  40                  45

Gly Trp Met Asn Pro Lys Ser Gly Asn Thr Gly Tyr Ala Gln Lys Phe
    50                  55                  60

Gln Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Arg Pro Arg Arg Arg Gly Gly Gly Phe Asp Ile Trp Gly
            100                 105                 110

Gln Gly Thr Met Val Thr Val Ser Ser
        115                 120
```

<210> SEQ ID NO 37
<211> LENGTH: 321
<212> TYPE: DNA
<213> ORGANISM: Artificial Sequence
<220> FEATURE:
<223> OTHER INFORMATION: Description of Artificial Sequence: Synthetic polynucleotide

```
<220> FEATURE:
<221> NAME/KEY: CDS
<222> LOCATION: (1)..(321)

<400> SEQUENCE: 37 gac atc cgg atg acc cag tct cca tcc tcc ctg tct gca tct gta gga      48
Asp Ile Arg Met Thr Gln Ser Pro Ser Ser Leu Ser Ala Ser Val Gly
1               5                   10                  15 gac aga gtc acc atc act tgc cgg gcg agt cag ggc att agc aat tat      96
Asp Arg Val Thr Ile Thr Cys Arg Ala Ser Gln Gly Ile Ser Asn Tyr
            20                  25                  30 tta gcc tgg tat cag cag aaa cca ggg aaa gtt cct aag ttc ctg atc     144
Leu Ala Trp Tyr Gln Gln Lys Pro Gly Lys Val Pro Lys Phe Leu Ile
        35                  40                  45 tat gct gca tcc act ttg caa tca ggg gtc cca tct cgg ttc agt ggc     192
Tyr Ala Ala Ser Thr Leu Gln Ser Gly Val Pro Ser Arg Phe Ser Gly
    50                  55                  60 agt gga tct ggg aca gat ttc act ctc acc atc agc agc ctg cag cct     240
Ser Gly Ser Gly Thr Asp Phe Thr Leu Thr Ile Ser Ser Leu Gln Pro
65                  70                  75                  80 gaa gat gtt gca act tat tac tgt cag aag tat aac agt gcc ccg tgg     288
Glu Asp Val Ala Thr Tyr Tyr Cys Gln Lys Tyr Asn Ser Ala Pro Trp
                85                  90                  95 acg ttc ggc caa ggg acc aag gtg gaa atc aaa                         321
Thr Phe Gly Gln Gly Thr Lys Val Glu Ile Lys
            100                 105

<210> SEQ ID NO 38
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Asp Ile Arg Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Val Pro Lys Phe Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asn Ser Ala Pro Trp
                85                  90                  95

Thr Phe Gly Gln Gly Thr Lys Val Glu Ile Lys
            100                 105

<210> SEQ ID NO 39
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(357)

<400> SEQUENCE: 39
```

```
caa gtg cag ctg gtg gag tct ggg gct gag gtg aag aag cct ggg gcc      48
Gln Val Gln Leu Val Glu Ser Gly Ala Glu Val Lys Lys Pro Gly Ala
1               5                   10                  15 tca gtg aag gtt tcc tgc aag gca tct gga tac acc ttc acc aac tac      96
Ser Val Lys Val Ser Cys Lys Ala Ser Gly Tyr Thr Phe Thr Asn Tyr
            20                  25                  30 tat atg cac tgg gtg cga cag gcc cct gga caa ggg ctc gag tgg atg     144
Tyr Met His Trp Val Arg Gln Ala Pro Gly Gln Gly Leu Glu Trp Met
        35                  40                  45 gga ata atc aac cct agt aga ggt agc aca agc tac gca cag aag ttc     192
Gly Ile Ile Asn Pro Ser Arg Gly Ser Thr Ser Tyr Ala Gln Lys Phe
    50                  55                  60 cag ggc aga gtc acc atg acc agg gac acg tcc acg agc aca gtc tac     240
Gln Gly Arg Val Thr Met Thr Arg Asp Thr Ser Thr Ser Thr Val Tyr
65                  70                  75                  80 atg gag ctg agc agc ctg aga tct gag gac acg gcc gtg tat tac tgt     288
Met Glu Leu Ser Ser Leu Arg Ser Glu Asp Thr Ala Val Tyr Tyr Cys
                85                  90                  95 gcg cga cgc cag atg gct aca ggc ccc ttt gac tac tgg ggc cag gga     336
Ala Arg Arg Gln Met Ala Thr Gly Pro Phe Asp Tyr Trp Gly Gln Gly
                100                 105                 110 acc ctg gtc acc gtc tcc tca                                          357
Thr Leu Val Thr Val Ser Ser
        115
```

<210> SEQ ID NO 40
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

```
Gln Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met His Trp Val Arg Gln Ala Pro Gly Gln Gly Leu Glu Trp Met
        35                  40                  45

Gly Ile Ile Asn Pro Ser Arg Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Arg Gln Met Ala Thr Gly Pro Phe Asp Tyr Trp Gly Gln Gly
                100                 105                 110

Thr Leu Val Thr Val Ser Ser
        115
```

<210> SEQ ID NO 41
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(339)

<400> SEQUENCE: 41

| | | | | | | | | | | | | | | | | |
|---|---|---|---|---|---|---|---|---|---|---|---|---|---|---|---|---|
| gat | att | gtg | ctg | act | cag | tct | cca | gac | tcc | ctg | gct | gtg | tct | ctg | ggc | 48 |
| Asp | Ile | Val | Leu | Thr | Gln | Ser | Pro | Asp | Ser | Leu | Ala | Val | Ser | Leu | Gly | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| gag | agg | gcc | acc | atc | aac | tgc | aag | tcc | agc | cag | agt | gtt | tta | tac | agc | 96 |
| Glu | Arg | Ala | Thr | Ile | Asn | Cys | Lys | Ser | Ser | Gln | Ser | Val | Leu | Tyr | Ser | |
| | | | 20 | | | | | 25 | | | | | 30 | | | |

| | | | | | | | | | | | | | | | | |
|---|---|---|---|---|---|---|---|---|---|---|---|---|---|---|---|---|
| tcc | aac | aat | aag | aac | tac | tta | gct | tgg | tac | cag | cag | aaa | cca | gga | cag | 144 |
| Ser | Asn | Asn | Lys | Asn | Tyr | Leu | Ala | Trp | Tyr | Gln | Gln | Lys | Pro | Gly | Gln | |
| | | 35 | | | | | 40 | | | | | 45 | | | | |

| | | | | | | | | | | | | | | | | |
|---|---|---|---|---|---|---|---|---|---|---|---|---|---|---|---|---|
| cct | cct | aag | ctg | ctc | att | tac | tgg | gca | tct | acc | cgg | gaa | tcc | ggg | gtc | 192 |
| Pro | Pro | Lys | Leu | Leu | Ile | Tyr | Trp | Ala | Ser | Thr | Arg | Glu | Ser | Gly | Val | |
| | 50 | | | | | 55 | | | | | 60 | | | | | |

| | | | | | | | | | | | | | | | | |
|---|---|---|---|---|---|---|---|---|---|---|---|---|---|---|---|---|
| cct | gac | cga | ttc | agt | ggc | agc | ggg | tct | ggg | aca | gat | ttc | act | ctc | acc | 240 |
| Pro | Asp | Arg | Phe | Ser | Gly | Ser | Gly | Ser | Gly | Thr | Asp | Phe | Thr | Leu | Thr | |
| 65 | | | | 70 | | | | | 75 | | | | | 80 | | |

| | | | | | | | | | | | | | | | | |
|---|---|---|---|---|---|---|---|---|---|---|---|---|---|---|---|---|
| atc | agc | agc | ctg | cag | gct | gaa | gat | gtg | gca | gtt | tat | tac | tgt | cag | caa | 288 |
| Ile | Ser | Ser | Leu | Gln | Ala | Glu | Asp | Val | Ala | Val | Tyr | Tyr | Cys | Gln | Gln | |
| | | | 85 | | | | | 90 | | | | | 95 | | | |

| | | | | | | | | | | | | | | | | |
|---|---|---|---|---|---|---|---|---|---|---|---|---|---|---|---|---|
| tat | tat | agt | act | cct | ccc | act | ttt | ggc | cag | ggg | acc | aag | ctg | gag | atc | 336 |
| Tyr | Tyr | Ser | Thr | Pro | Pro | Thr | Phe | Gly | Gln | Gly | Thr | Lys | Leu | Glu | Ile | |
| | | | 100 | | | | | 105 | | | | | 110 | | | |

| | | |
|---|---|---|
| aaa | | 339 |
| Lys | | |

<210> SEQ ID NO 42
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Asp Ile Val Leu Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Pro Thr Phe Gly Gln Gly Thr Lys Leu Glu Ile
            100                 105                 110

Lys

<210> SEQ ID NO 43
<211> LENGTH: 121
<212> TYPE: PRT
<213> ORGANISM: Artificial Sequence
<220> FEATURE:
<223> OTHER INFORMATION: Description of Artificial Sequence: Synthetic
      consensus polypeptide
<220> FEATURE:
<221> NAME/KEY: MOD_RES
<222> LOCATION: (33)..(33)

```
<223> OTHER INFORMATION: Ala, Asp or Tyr
<220> FEATURE:
<221> NAME/KEY: MOD_RES
<222> LOCATION: (54)..(54)
<223> OTHER INFORMATION: Gly, Phe, Lys, Asn or Ser
<220> FEATURE:
<221> NAME/KEY: MOD_RES
<222> LOCATION: (55)..(55)
<223> OTHER INFORMATION: Asn, Ser, Gly, Arg or Ala
<220> FEATURE:
<221> NAME/KEY: MOD_RES
<222> LOCATION: (57)..(57)
<223> OTHER INFORMATION: Asn, Phe, Ser or Tyr
<220> FEATURE:
<221> NAME/KEY: MOD_RES
<222> LOCATION: (59)..(59)
<223> OTHER INFORMATION: Ile, Lys, Gly or Ser
<220> FEATURE:
<221> NAME/KEY: MOD_RES
<222> LOCATION: (76)..(76)
<223> OTHER INFORMATION: Ala, Ile, Thr or Arg
<220> FEATURE:
<221> NAME/KEY: MOD_RES
<222> LOCATION: (99)..(99)
<223> OTHER INFORMATION: Trp, Leu, Glu, Arg or Phe
<220> FEATURE:
<221> NAME/KEY: MOD_RES
<222> LOCATION: (100)..(100)
<223> OTHER INFORMATION: Val, Glu, Arg or not present
<220> FEATURE:
<221> NAME/KEY: MOD_RES
<222> LOCATION: (101)..(101)
<223> OTHER INFORMATION: May or may not be present
<220> FEATURE:
<221> NAME/KEY: MOD_RES
<222> LOCATION: (102)..(102)
<223> OTHER INFORMATION: Gly, Ser, Arg, Asn, Gln or Val
<220> FEATURE:
<221> NAME/KEY: MOD_RES
<222> LOCATION: (103)..(103)
<223> OTHER INFORMATION: Gly, Asn, Arg, Ile, Met or Val
<220> FEATURE:
<221> NAME/KEY: MOD_RES
<222> LOCATION: (107)..(107)
<223> OTHER INFORMATION: Tyr, Ala, Gly or Pro

<400> SEQUENCE: 43

Gln Val Gln Leu Leu Glu Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Xaa Met His Trp Val Arg Gln Ala Pro Gly Gln Gly Leu Glu Trp Met
        35                  40                  45

Gly Trp Ile Asn Pro Xaa Xaa Gly Xaa Thr Xaa Tyr Ala Gln Lys Phe
    50                  55                  60

Gln Gly Arg Val Thr Met Thr Arg Asp Thr Ser Xaa Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Xaa Xaa Pro Xaa Xaa Val Gly Gly Xaa Phe Asp Tyr Trp Gly
            100                 105                 110

Gln Gly Thr Leu Val Thr Val Ser Ser
        115                 120

<210> SEQ ID NO 44
<211> LENGTH: 113
<212> TYPE: PRT
<213> ORGANISM: Artificial Sequence
<220> FEATURE:
<223> OTHER INFORMATION: Description of Artificial Sequence: Synthetic
```

```
                consensus polypeptide
<220> FEATURE:
<221> NAME/KEY: MOD_RES
<222> LOCATION: (33)..(33)
<223> OTHER INFORMATION: Pro, Ser or not present
<220> FEATURE:
<221> NAME/KEY: MOD_RES
<222> LOCATION: (35)..(35)
<223> OTHER INFORMATION: Gly, Lys, Asn or not present

<400> SEQUENCE: 44

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Tyr Ser
            20                  25                  30

Xaa Asn Xaa Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Pro Thr Phe Gly Gln Gly Thr Lys Val Glu Ile
            100                 105                 110

Lys
```